US012780866B2

(12) United States Patent
Endo et al.

(10) Patent No.: US 12,780,866 B2
(45) Date of Patent: Nov. 3, 2026

(54) SYNTHESIS OF TRINUCLEOTIDE AND TETRANUCLEOTIDE CAPS FOR MRNA PRODUCTION

(71) Applicant: ModernaTX, Inc., Cambridge, MA (US)

(72) Inventors: Atsushi Endo, Belmont, MA (US); Gabor Butora, Martinsville, NJ (US); Thomas Steele, Cambridge, MA (US); Jennifer Beaudoin, Cambridge, MA (US)

(73) Assignee: ModernaTX, Inc., Cambridge, MA (US)

( * ) Notice: Subject to any disclaimer, the term of this patent is extended or adjusted under 35 U.S.C. 154(b) by 293 days.

(21) Appl. No.: 18/284,395

(22) PCT Filed: Mar. 30, 2022

(86) PCT No.: PCT/US2022/022453

§ 371 (c)(1),
(2) Date: Sep. 27, 2023

(87) PCT Pub. No.: WO2022/212442

PCT Pub. Date: Oct. 6, 2022

(65) Prior Publication Data

US 2024/0383940 A1 Nov. 21, 2024

Related U.S. Application Data

(60) Provisional application No. 63/168,799, filed on Mar. 31, 2021.

(51) Int. Cl.

| | |
|---|---|
| ***C07H 21/02*** | (2006.01) |
| ***C07F 9/24*** | (2006.01) |
| ***C07H 1/02*** | (2006.01) |
| ***C07H 19/167*** | (2006.01) |
| ***C07H 19/207*** | (2006.01) |

(52) U.S. Cl.

CPC ........... *C07H 21/02* (2013.01); *C07F 9/2408* (2013.01); *C07H 1/02* (2013.01); *C07H 19/167* (2013.01); *C07H 19/207* (2013.01)

(58) Field of Classification Search

None

See application file for complete search history.

(56) References Cited

U.S. PATENT DOCUMENTS

| | | | |
|---|---|---|---|
| 7,074,596 | B2 | 7/2006 | Darzynkiewicz et al. |
| 8,710,200 | B2 | 4/2014 | Schrum et al. |
| 8,754,062 | B2 | 6/2014 | De Fougerolles et al. |
| 8,822,663 | B2 | 9/2014 | Schrum et al. |
| 8,980,864 | B2 | 3/2015 | Hoge et al. |
| 8,999,380 | B2 | 4/2015 | Bancel et al. |
| 9,221,891 | B2 | 12/2015 | Bancel et al. |
| 9,283,287 | B2 | 3/2016 | Bancel et al. |
| 9,303,079 | B2 | 4/2016 | Bancel et al. |
| 9,464,124 | B2 | 10/2016 | Bancel et al. |
| 9,512,456 | B2 | 12/2016 | Wang et al. |
| 9,533,047 | B2 | 1/2017 | De Fougerolles et al. |
| 9,572,896 | B2 | 2/2017 | Bancel et al. |
| 9,597,380 | B2 | 3/2017 | Chakraborty et al. |
| 9,675,668 | B2 | 6/2017 | Bancel et al. |
| 9,868,691 | B2 | 1/2018 | Benenato et al. |
| 9,872,900 | B2 | 1/2018 | Ciaramella et al. |
| 10,023,626 | B2 | 7/2018 | Bolen et al. |
| 10,064,934 | B2 | 9/2018 | Ciaramella et al. |
| 10,064,935 | B2 | 9/2018 | Ciaramella et al. |
| 10,124,055 | B2 | 11/2018 | Ciaramella et al. |
| 10,207,010 | B2 | 2/2019 | Besin et al. |
| 10,232,055 | B2 | 3/2019 | Kariko et al. |
| 10,273,269 | B2 | 4/2019 | Ciaramella |
| 10,286,086 | B2 | 5/2019 | Roy et al. |
| 10,323,076 | B2 | 6/2019 | Ellsworth et al. |
| 10,385,088 | B2 | 8/2019 | Fraley et al. |
| 10,449,244 | B2 | 10/2019 | Ciaramella et al. |
| 10,465,190 | B1 | 11/2019 | Chen et al. |
| 10,493,143 | B2 | 12/2019 | Ciaramella et al. |
| 10,526,629 | B2 | 1/2020 | Rabideau et al. |
| 10,653,712 | B2 | 5/2020 | Hoge |
| 10,653,767 | B2 | 5/2020 | Ciaramella et al. |
| 10,695,419 | B2 | 6/2020 | Ciaramella et al. |
| 10,857,105 | B2 | 12/2020 | Benenato et al. |
| 10,925,958 | B2 | 2/2021 | Ciaramella |
| 11,027,025 | B2 | 6/2021 | Hoge et al. |

(Continued)

FOREIGN PATENT DOCUMENTS

| | | | |
|---|---|---|---|
| WO | WO 2005/028494 | A1 | 3/2005 |
| WO | WO 2008/157688 | A2 | 12/2008 |

(Continued)

OTHER PUBLICATIONS

International Search Report and Written Opinion for Application No. PCT/US2022/022453, mailed Jul. 4, 2022.

Cowling, Regulation of mRNA cap methylation. Biochem J. Dec. 23, 2009;425(2):295-302. doi: 10.1042/BJ20091352.

Grudzien-Nogalska et al., Phosphorothioate cap analogs stabilize mRNA and increase translational efficiency in mammalian cells. RNA. Oct. 2007;13(10):1745-55. Epub Aug. 24, 2007.

Jemielity et al., Novel "anti-reverse" cap analogs with superior translational properties. RNA. Sep. 2003;9 (9):1108-22.

Kore et al., Synthesis and biological validation of $N^7$-(4-chlorophenoxyethyl) substituted dinucleotide cap analogs for mRNA translation. Bioorg Med Chem. Aug. 1, 2013;21(15):4570-4. doi:10.1016/j.bmc.2013.05.041. Epub Jun. 1, 2013.

Rydzik et al., Synthetic dinucleotide mRNA cap analogs with tetraphosphate 5',5' bridge containing methylenebis(phosphonate) modification. Org Biomol Chem. Nov. 21, 2009;7(22):4763-76. doi: 10.1039/b911347a. Epub Sep. 7, 2009.

(Continued)

*Primary Examiner* — Patrick T Lewis

(74) *Attorney, Agent, or Firm* — Clark & Elbing LLP

(57) ABSTRACT

Provided herein are methods of making trinucleotides and tetranucleotides for use as 5' mRNA caps. The methods utilize a novel "top-down" strategy and provide for synthesis of oligonucleotides with higher yields and increased efficiency compared to traditional methods. A key step of the methods disclosed, herein can also be adapted to utilize a "one-pot" approach, resulting in an increase in the yield of the final oligonucleotide product.

20 Claims, 3 Drawing Sheets

(56) References Cited

U.S. PATENT DOCUMENTS

| | | | |
|---|---|---|---|
| 11,045,540 | B2 | 6/2021 | Ciaramella |
| 11,103,578 | B2 | 8/2021 | Ciaramella et al. |
| 11,351,242 | B1 | 6/2022 | Lori et al. |
| 11,384,352 | B2 | 7/2022 | Miracco |
| 11,406,703 | B2 | 8/2022 | Kramarczyk et al. |
| 11,464,848 | B2 | 10/2022 | Ciaramella et al. |
| 11,485,960 | B2 | 11/2022 | Dousis et al. |
| 11,497,807 | B2 | 11/2022 | Ciaramella et al. |
| 11,564,893 | B2 | 1/2023 | Smith |
| 11,576,961 | B2 | 2/2023 | Ciaramella et al. |
| 11,643,441 | B1 | 5/2023 | Ciaramella et al. |
| 11,696,946 | B2 | 7/2023 | Ciaramella |
| 11,752,206 | B2 | 9/2023 | Ciaramella et al. |
| 11,786,607 | B2 | 10/2023 | Hoge et al. |
| 11,851,694 | B1 | 12/2023 | Mauger et al. |
| 11,866,696 | B2 | 1/2024 | Issa et al. |
| 11,872,278 | B2 | 1/2024 | Ciaramella et al. |
| 11,905,525 | B2 | 2/2024 | Brito et al. |
| 11,911,453 | B2 | 2/2024 | Ciaramella et al. |
| 11,912,982 | B2 | 2/2024 | Issa et al. |
| 12,070,495 | B2 | 8/2024 | Lusso et al. |
| 2003/0135040 | A1 | 7/2003 | Eritja et al. |
| 2010/0261231 | A1 | 10/2010 | Kore et al. |
| 2013/0102034 | A1 | 4/2013 | Schrum et al. |
| 2013/0102655 | A1 | 4/2013 | Kore et al. |
| 2013/0236974 | A1 | 9/2013 | De Fougerolles |
| 2013/0245103 | A1 | 9/2013 | de Fougerolles et al. |
| 2013/0259923 | A1 | 10/2013 | Bancel et al. |
| 2014/0147432 | A1 | 5/2014 | Bancel et al. |
| 2014/0148502 | A1 | 5/2014 | Bancel et al. |
| 2014/0193482 | A1 | 7/2014 | Bancel et al. |
| 2014/0206752 | A1 | 7/2014 | Afeyan et al. |
| 2014/0378538 | A1 | 12/2014 | Bancel |
| 2015/0051268 | A1 | 2/2015 | Bancel et al. |
| 2015/0056253 | A1 | 2/2015 | Bancel et al. |
| 2015/0141499 | A1 | 5/2015 | Bancel et al. |
| 2015/0307542 | A1 | 10/2015 | Roy et al. |
| 2015/0315541 | A1 | 11/2015 | Bancel et al. |
| 2016/0024140 | A1 | 1/2016 | Issa et al. |
| 2016/0024141 | A1 | 1/2016 | Issa et al. |
| 2016/0032273 | A1 | 2/2016 | Shahrokh et al. |
| 2016/0038612 | A1 | 2/2016 | Hoge et al. |
| 2016/0194368 | A1 | 7/2016 | Hoge et al. |
| 2016/0194625 | A1 | 7/2016 | Hoge et al. |
| 2016/0243221 | A1 | 8/2016 | Hoge et al. |
| 2017/0043037 | A1 | 2/2017 | Kariko et al. |
| 2017/0130255 | A1 | 5/2017 | Wang et al. |
| 2017/0202979 | A1 | 7/2017 | Chakraborty et al. |
| 2017/0204152 | A1 | 7/2017 | Nelson et al. |
| 2018/0000953 | A1 | 1/2018 | Almarsson et al. |
| 2018/0002393 | A1 | 1/2018 | Bancel et al. |
| 2018/0237849 | A1 | 8/2018 | Thompson |
| 2018/0243225 | A1 | 8/2018 | Ciaramella |
| 2018/0256628 | A1 | 9/2018 | Hoge et al. |
| 2018/0271795 | A1 | 9/2018 | Martini et al. |
| 2018/0271970 | A1 | 9/2018 | Ciaramella et al. |
| 2018/0273977 | A1 | 9/2018 | Mousavi et al. |
| 2018/0303929 | A1 | 10/2018 | Ciaramella et al. |
| 2018/0311336 | A1 | 11/2018 | Ciaramella et al. |
| 2018/0311343 | A1 | 11/2018 | Huang et al. |
| 2018/0318409 | A1 | 11/2018 | Valiante et al. |
| 2018/0369374 | A1 | 12/2018 | Frederick et al. |
| 2018/0371047 | A1 | 12/2018 | Ticho et al. |
| 2019/0002890 | A1 | 1/2019 | Martini et al. |
| 2019/0008938 | A1 | 1/2019 | Ciaramella et al. |
| 2019/0085368 | A1 | 3/2019 | Bancel et al. |
| 2019/0125839 | A1 | 5/2019 | Frederick et al. |
| 2019/0144490 | A1 | 5/2019 | Hogrefe et al. |
| 2019/0175517 | A1 | 6/2019 | Martini et al. |
| 2019/0175727 | A1 | 6/2019 | Huang et al. |
| 2019/0192646 | A1 | 6/2019 | Cohen et al. |
| 2019/0192653 | A1 | 6/2019 | Hoge et al. |
| 2019/0275170 | A1 | 9/2019 | Benenato et al. |
| 2019/0298657 | A1 | 10/2019 | Martini et al. |
| 2019/0298658 | A1 | 10/2019 | Benenato |
| 2019/0300906 | A1 | 10/2019 | Martini et al. |
| 2019/0314292 | A1 | 10/2019 | Benenato et al. |
| 2019/0336452 | A1 | 11/2019 | Brader |
| 2019/0351040 | A1 | 11/2019 | Valiante et al. |
| 2019/0382774 | A1 | 12/2019 | Hoge et al. |
| 2019/0390181 | A1 | 12/2019 | Benenato et al. |
| 2020/0032274 | A1 | 1/2020 | Mauger et al. |
| 2020/0038499 | A1 | 2/2020 | Narayanan et al. |
| 2020/0054737 | A1 | 2/2020 | Ciaramella et al. |
| 2020/0069599 | A1 | 3/2020 | Smith et al. |
| 2020/0085916 | A1 | 3/2020 | Martini et al. |
| 2020/0109420 | A1 | 4/2020 | Brito et al. |
| 2020/0129445 | A1 | 4/2020 | Patel et al. |
| 2020/0239869 | A1 | 7/2020 | Issa et al. |
| 2020/0254086 | A1 | 8/2020 | Hoge et al. |
| 2020/0282047 | A1 | 9/2020 | Ciaramella et al. |
| 2020/0306191 | A1 | 10/2020 | Schariter et al. |
| 2020/0338004 | A1 | 10/2020 | Hansson et al. |
| 2020/0368162 | A1 | 11/2020 | Martini |
| 2021/0046173 | A1 | 2/2021 | Ciaramella et al. |
| 2021/0087135 | A1 | 3/2021 | Benenato et al. |
| 2021/0163919 | A1 | 6/2021 | Issa et al. |
| 2021/0206818 | A1 | 7/2021 | Huang et al. |
| 2021/0217484 | A1 | 7/2021 | Giessel et al. |
| 2021/0228707 | A1 | 7/2021 | Mektar et al. |
| 2021/0268086 | A1 | 9/2021 | Zhong et al. |
| 2021/0378980 | A1 | 12/2021 | Horhota et al. |
| 2022/0031631 | A1 | 2/2022 | Almarsson et al. |
| 2022/0047518 | A1 | 2/2022 | Hennessy et al. |
| 2022/0054653 | A1 | 2/2022 | Martini et al. |
| 2022/0062175 | A1 | 3/2022 | Smith et al. |
| 2022/0125899 | A1 | 4/2022 | Ashburn et al. |
| 2022/0145381 | A1 | 5/2022 | Elich et al. |
| 2022/0236253 | A1 | 7/2022 | Hopson |
| 2022/0241399 | A1 | 8/2022 | Lusso et al. |
| 2022/0347292 | A1 | 11/2022 | Panther et al. |
| 2022/0348900 | A1 | 11/2022 | Shamashkin et al. |
| 2022/0349006 | A1 | 11/2022 | Amato et al. |
| 2023/0000970 | A1 | 1/2023 | Nachbagauer et al. |
| 2023/0142529 | A1 | 5/2023 | White et al. |
| 2023/0181481 | A1 | 6/2023 | White et al. |
| 2023/0190761 | A1 | 6/2023 | Brader et al. |
| 2023/0212645 | A1 | 7/2023 | Marquardt et al. |
| 2023/0287437 | A1 | 9/2023 | Smith et al. |
| 2023/0338506 | A1 | 10/2023 | Shaw et al. |
| 2023/0346914 | A1 | 11/2023 | Stewart-Jones et al. |
| 2023/0355743 | A1 | 11/2023 | Stewart-Jones et al. |
| 2024/0100145 | A1 | 3/2024 | Bollman et al. |
| 2024/0100151 | A1 | 3/2024 | Carfi et al. |
| 2024/0139309 | A1 | 5/2024 | Carfi et al. |
| 2024/0173400 | A1 | 5/2024 | Ciaramella et al. |
| 2024/0181030 | A1 | 6/2024 | Himansu et al. |
| 2024/0207392 | A1 | 6/2024 | Chandramouli et al. |
| 2024/0209068 | A1 | 6/2024 | Deal et al. |
| 2024/0226028 | A1 | 7/2024 | Goldman et al. |
| 2024/0226277 | A1 | 7/2024 | Nachbagauer et al. |
| 2024/0229109 | A1 | 7/2024 | Rabideau et al. |
| 2024/0238211 | A1 | 7/2024 | Brader et al. |
| 2024/0263226 | A1 | 8/2024 | Schmitt |
| 2024/0285754 | A1 | 8/2024 | Stewart-Jones |
| 2024/0293534 | A1 | 9/2024 | Stewart-Jones |
| 2024/0299531 | A1 | 9/2024 | Stewart-Jones |

FOREIGN PATENT DOCUMENTS

| | | | |
|---|---|---|---|
| WO | WO 2009/149253 | A2 | 12/2009 |
| WO | WO 2011/005860 | A2 | 1/2011 |
| WO | WO 2011/028218 | A1 | 3/2011 |
| WO | WO 2013/090648 | A1 | 6/2013 |
| WO | WO 2014/144711 | A1 | 9/2014 |
| WO | WO 2014/152030 | A1 | 9/2014 |
| WO | WO 2014/159813 | A1 | 10/2014 |
| WO | WO 2015/085318 | A2 | 6/2015 |
| WO | WO 2016/164762 | A1 | 10/2016 |
| WO | WO 2016/201377 | A1 | 12/2016 |
| WO | WO 2017/011773 | A2 | 1/2017 |
| WO | WO 2017/015457 | A1 | 1/2017 |
| WO | WO 2017/066789 | A1 | 4/2017 |
| WO | WO 2017/070601 | A1 | 4/2017 |

(56) References Cited

FOREIGN PATENT DOCUMENTS

| | | | |
|---|---|---|---|
| WO | WO 2017/112865 | A1 | 6/2017 |
| WO | WO 2018/232355 | A1 | 12/2018 |
| WO | WO 2019/018765 | A1 | 1/2019 |
| WO | WO 2019/036683 | A1 | 2/2019 |
| WO | WO 2020/061367 | A1 | 3/2020 |
| WO | WO 2020/172239 | A1 | 8/2020 |
| WO | WO 2020/190750 | A1 | 9/2020 |
| WO | WO 2021/132589 | A1 | 1/2021 |
| WO | WO 2021/050864 | A1 | 3/2021 |
| WO | WO 2021/055849 | A1 | 3/2021 |
| WO | WO 2021/155274 | A1 | 8/2021 |
| WO | WO 2021/159130 | A1 | 8/2021 |
| WO | WO 2021/211343 | A1 | 10/2021 |
| WO | WO 2021/222304 | A1 | 11/2021 |
| WO | WO 2021/231963 | A1 | 11/2021 |
| WO | WO 2021/237084 | A1 | 11/2021 |
| WO | WO 2022/032154 | A2 | 2/2022 |
| WO | WO 2022/155524 | A1 | 7/2022 |
| WO | WO 2022/155530 | A1 | 8/2022 |
| WO | WO 2022/187698 | A1 | 9/2022 |
| WO | WO 2022/197624 | A1 | 9/2022 |
| WO | WO 2022/204491 | A1 | 9/2022 |
| WO | WO 2022/212191 | A1 | 10/2022 |
| WO | WO 2022/212442 | A1 | 10/2022 |
| WO | WO 2022/212711 | A1 | 10/2022 |
| WO | WO 2022/221335 | A1 | 10/2022 |
| WO | WO 2022/221336 | A1 | 10/2022 |
| WO | WO 2022/221359 | A1 | 10/2022 |
| WO | WO 2022/221440 | A1 | 10/2022 |
| WO | WO 2022/226277 | A1 | 10/2022 |
| WO | WO 2022/226318 | A1 | 10/2022 |
| WO | WO 2022/232585 | A1 | 11/2022 |
| WO | WO 2022/241103 | A1 | 11/2022 |
| WO | WO 2022/245888 | A1 | 11/2022 |
| WO | WO 2022/266010 | A1 | 12/2022 |
| WO | WO 2022/266012 | A1 | 12/2022 |
| WO | WO 2022/266389 | A1 | 12/2022 |
| WO | WO 2023/283642 | A1 | 1/2023 |
| WO | WO 2023/283645 | A1 | 1/2023 |
| WO | WO 2023/283651 | A1 | 1/2023 |
| WO | WO 2023/014649 | A1 | 2/2023 |
| WO | WO 2023/018773 | A1 | 2/2023 |
| WO | WO 2023/018923 | A1 | 2/2023 |
| WO | WO 2023/019181 | A1 | 2/2023 |
| WO | WO 2023/056401 | A1 | 4/2023 |
| WO | WO 2023/069625 | A1 | 4/2023 |
| WO | WO 2023/069895 | A1 | 4/2023 |
| WO | WO 2023/069900 | A1 | 4/2023 |
| WO | WO 2023/076358 | A1 | 5/2023 |
| WO | WO 2023/076658 | A1 | 5/2023 |
| WO | WO 2023/081311 | A1 | 5/2023 |
| WO | WO 2023/092069 | A1 | 5/2023 |
| WO | WO 2023/107999 | A2 | 6/2023 |
| WO | WO 2023/114307 | A1 | 6/2023 |
| WO | WO 2023/132885 | A1 | 7/2023 |
| WO | WO 2023/137149 | A1 | 7/2023 |
| WO | WO 2023/150256 | A1 | 8/2023 |
| WO | WO 2023/154818 | A1 | 8/2023 |
| WO | WO 2023/196914 | A1 | 10/2023 |
| WO | WO 2023/201204 | A1 | 10/2023 |
| WO | WO 2023/201294 | A1 | 10/2023 |
| WO | WO 2023/201296 | A1 | 10/2023 |
| WO | WO 2023/212696 | A1 | 11/2023 |
| WO | WO 2023/225524 | A1 | 11/2023 |
| WO | WO 2023/250119 | A1 | 12/2023 |
| WO | WO 2024/010993 | A1 | 1/2024 |
| WO | WO 2024/015890 | A1 | 1/2024 |
| WO | WO 2024/026005 | A1 | 2/2024 |
| WO | WO 2024/030369 | A1 | 2/2024 |
| WO | WO 2024/050483 | A1 | 3/2024 |
| WO | WO 2024/097874 | A1 | 5/2024 |
| WO | WO 2024/123978 | A1 | 6/2024 |
| WO | WO 2024/151811 | A1 | 7/2024 |
| WO | WO 2024/163465 | A1 | 8/2024 |
| WO | WO 2024/191860 | A2 | 9/2024 |
| WO | WO 2024/206835 | A1 | 10/2024 |
| WO | WO 2024/215721 | A1 | 10/2024 |

OTHER PUBLICATIONS

Zhou et al., New regiospecific synthesis of the “branched” tri-, penta- & hepta-ribonucleic acids which are formed as the “lariat” in the pre-mRNA processing reactions[Splicing]. Tetrahedron. Jan. 1, 1988;44(20):6471-6489. doi: 10.1016/S0040-4020(01)89837-9.

Zlatev et al., Use of a solid-supported coupling reagent for a selective phosphitylation of the primary alcohol of N2-isobutyryl-2'-deoxy or 2'-O-methyl guanosine. Tetrahedron Letters. Nov. 2006; 47 (47):8379-8382. doi: 10.1016/j.tetlet.2006.09.086. Epub Oct. 5, 2006.

SYNTHESIS OF TRINUCLEOTIDE AND TETRANUCLEOTIDE CAPS FOR MRNA PRODUCTION

RELATED APPLICATIONS

This application is a National Stage filing under 35 U.S.C. 371 of International PCT Application No. PCT/US2022/022453, filed Mar. 30, 2022, which claims priority under 35 U.S.C. § 119(e) to U.S. Provisional Application, U.S. Ser. No. 63/168,799, filed Mar. 31, 2021, each of which is incorporated herein by reference in its entirety.

BACKGROUND

Short oligonucleotides, including trinucleotides and tetranucleotides, are useful as caps in the production of mRNA. Capping of mRNA increases its stability and can also prevent its degradation by exonucleases, promote its translation, and regulate its export from the nucleus (Ramanathan, A. et al. mRNA capping: biological functions and application. *Nucleic Acids Res.* 2016, 44(16), 7511-7526). Conventional strategies for synthesizing trinucleotides and tetranucleotides typically involve a "bottom-up" approach, in which new nucleotides are added to the 5' end of the growing oligonucleotide chain. While these strategies benefit from the fact that they mirror traditional methods used for solid-phase oligonucleotide synthesis, as well as the fact that the monomeric building blocks typically comprise a standard functionalization pattern that is compatible with precedented chemistry, conventional "bottom-up" approaches also suffer from numerous drawbacks. These include issues with the compatibility of the necessary protecting groups under acidic conditions, resulting in decreased yields, and the delay of the installation of the 5'-phosphate moiety until the end of the synthesis. Accordingly, new and improved methods for the synthesis of trinucleotides and tetranucleotides are needed.

SUMMARY

The present application describes new methods for the synthesis of oligonucleotides utilizing a "top-down" approach, in which a new nucleoside/nucleotide unit is added at the 3' end of the growing oligonucleotide chain. Such an approach, as detailed herein, allows for pre-installation of all phosphorus functionalities of the oligonucleotide at the stage where the monomers are synthesized, and takes advantage of the inherent chemical reactivity difference between the 5' hydroxyl and 3' hydroxyl groups of the monomeric nucleosides/nucleotides. Furthermore, the top-down approach allows for the development of a new protecting group strategy that has increased compatibility with the acidic conditions utilized in oligonucleotide synthesis and avoids the complications and inefficiencies caused by the acid labile protecting groups that have traditionally been used. Finally, the top-down strategy described herein may also be adapted to perform a key step using a "one-pot" approach that improves the efficiency of the synthesis and significantly increases the yield of the final oligonucleotide product.

Accordingly, provided herein are methods for synthesizing a trinucleotide comprising reacting a compound, or salt thereof, of formula (4) with a compound, or salt thereof, of formula (5):

(4)

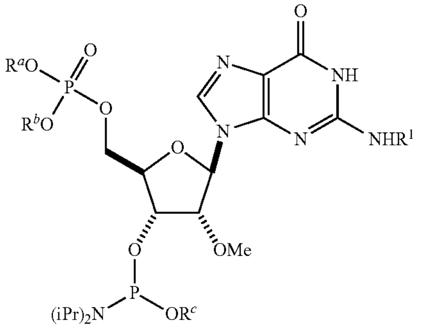

and (5)

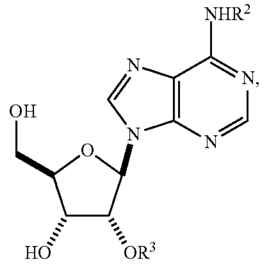

to obtain a compound of formula (6), or a salt thereof:

(6)

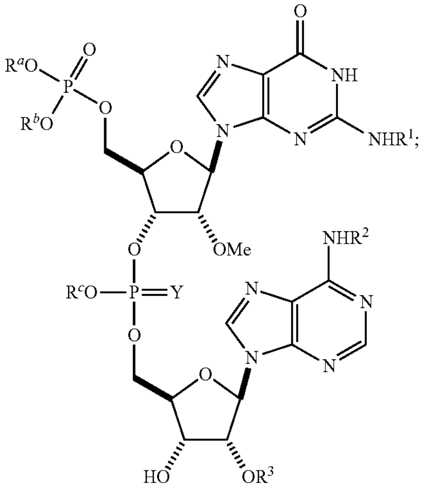

and reacting the compound of formula (6) with a compound of formula (10), or a salt thereof:

(10)

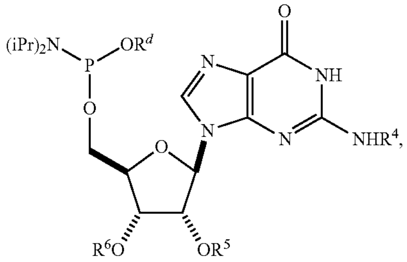

to obtain a compound of formula (11):

(11)

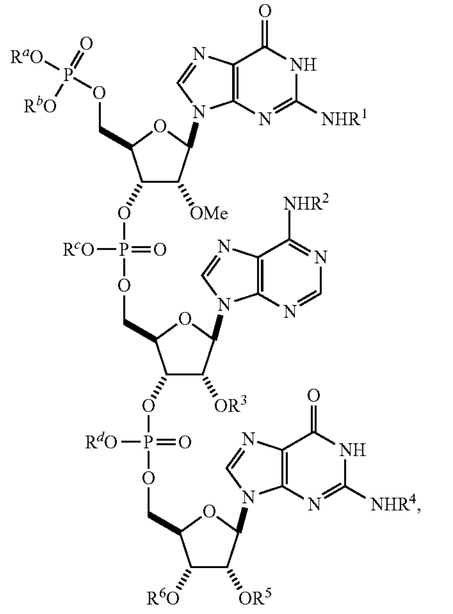

wherein $R^1$, $R^2$, $R^3$, $R^4$, $R^5$, $R^6$, $R^{aa}$, $R^{bb}$, $R^c$, and $R^{dd}$ are defined herein.

The details of certain embodiments of the disclosure are set forth in the Detailed Description of Certain Embodiments, as described below. Other features, objects, and advantages of the disclosure will be apparent from the Definitions, Examples, and Claims.

DEFINITIONS

Figure 1:
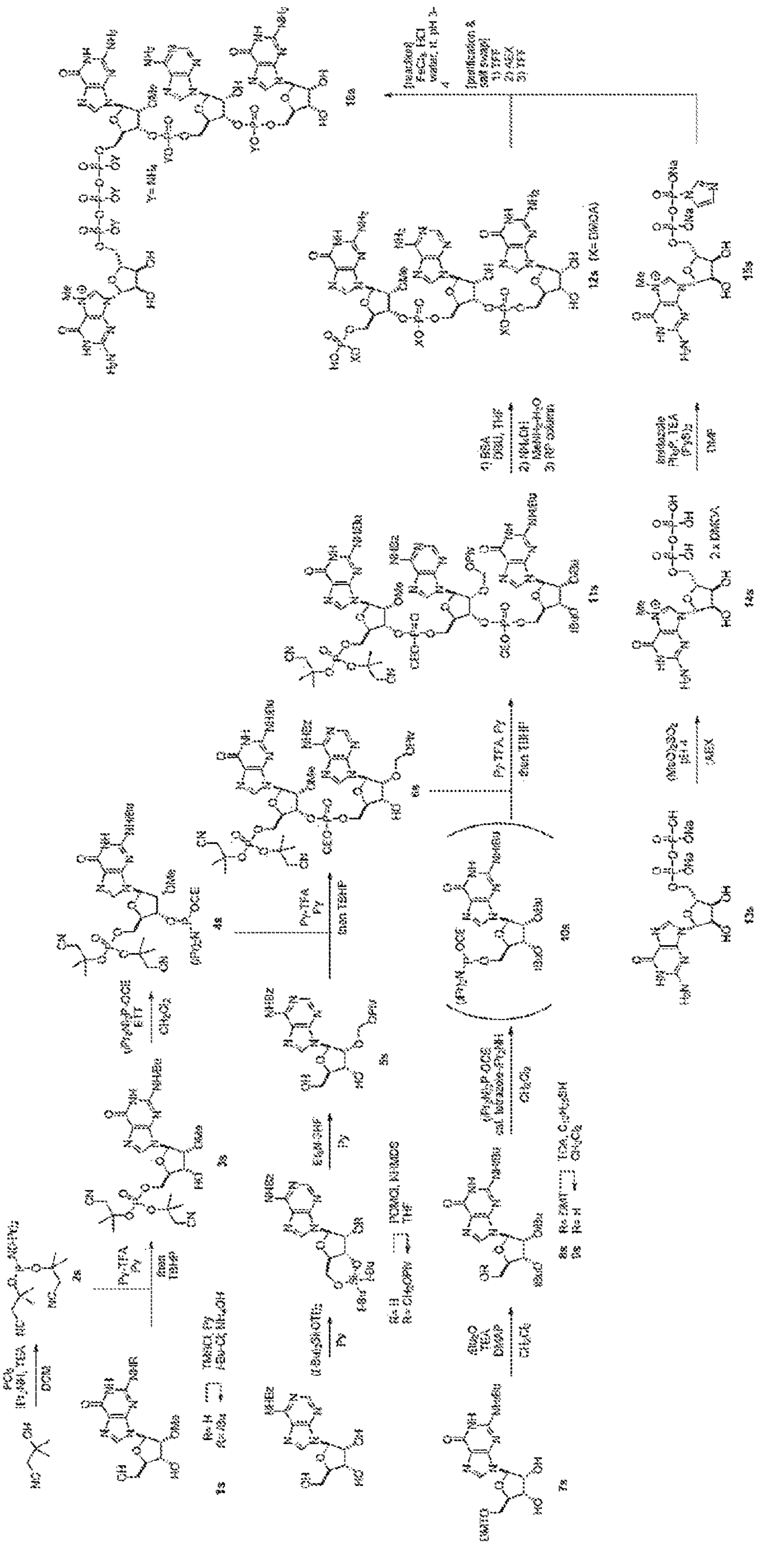
FIG. 1 provides a synthetic scheme for a stepwise process of trinucleotide assembly.
Figure 2:
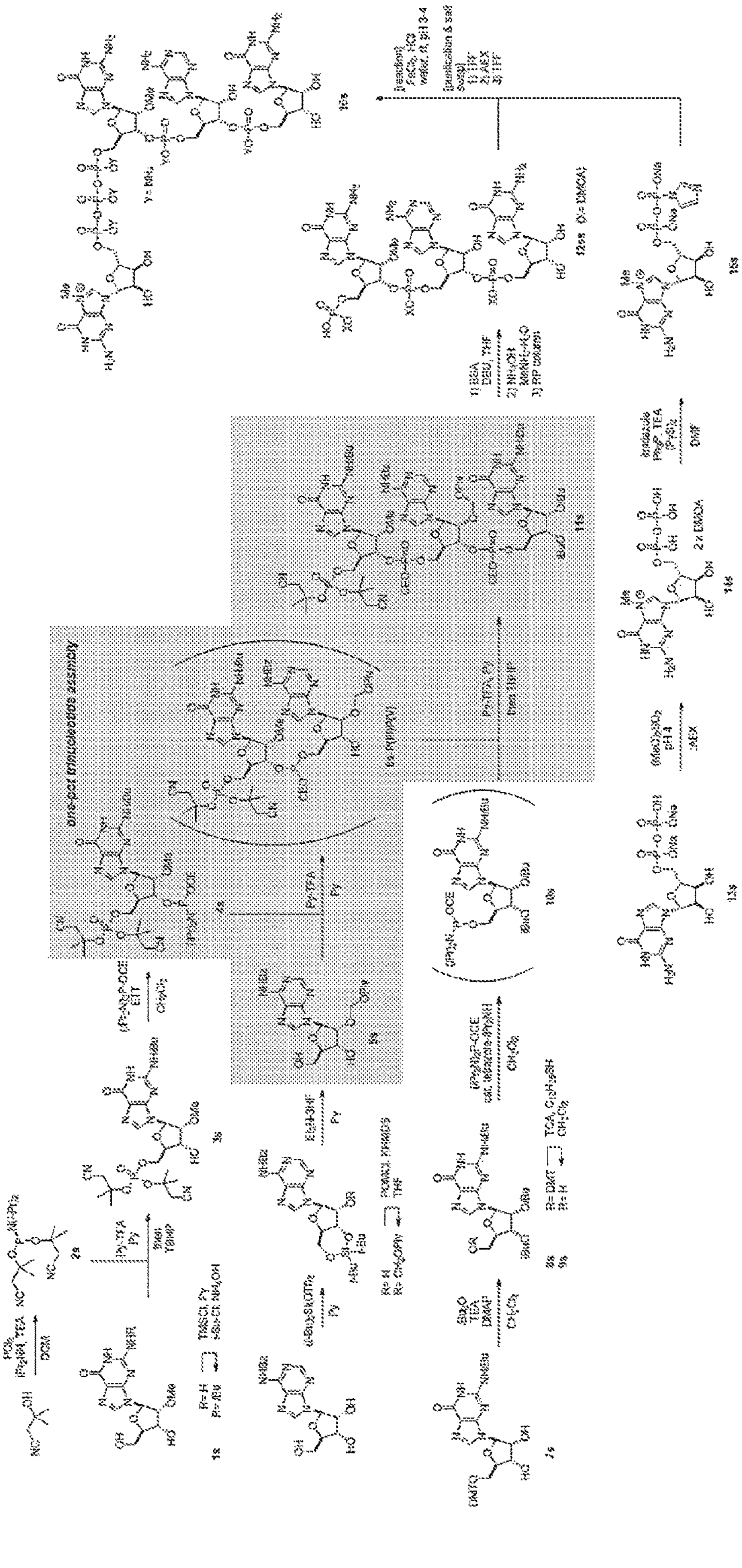
FIG. 2 provides a synthetic scheme for a one-pot process of trinucleotide assembly.
Figure 3:
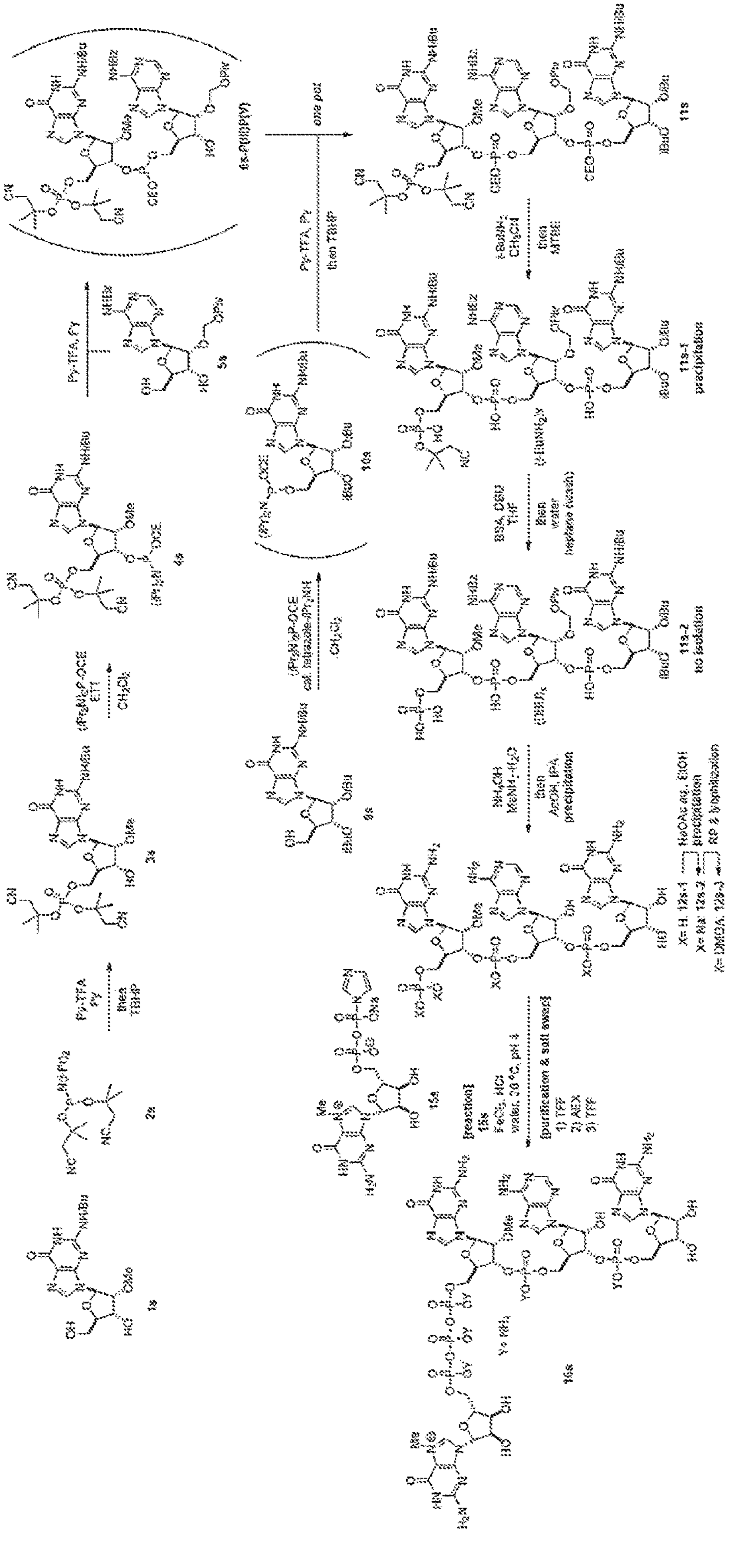
FIG. 3 provides an alternative synthetic scheme for a one-pot process for trinucleotide assembly.

Definitions of specific functional groups and chemical terms are described in more detail below. The chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Michael B. Smith, *March's Advanced Organic Chemistry*, $7^{th}$ Edition, John Wiley & Sons, Inc., New York, 2013; Richard C. Larock, *Comprehensive Organic Transformations*, John Wiley & Sons, Inc., New York, 2018; and Carruthers, *Some Modern Methods of Organic Synthesis*, $3^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, E. L. *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, IN 1972). The invention additionally encompasses compounds as individual isomers substantially free of other isomers, and alternatively, as mixtures of various isomers.

Unless otherwise provided, formulae and structures depicted herein include compounds that do not include isotopically enriched atoms, and also include compounds that include isotopically enriched atoms. For example, compounds having the present structures except for the replacement of hydrogen by deuterium or tritium, replacement of $^{19}F$ with $^{18}F$, or the replacement of a carbon by a $^{13}C$- or $^{14}C$-enriched carbon are within the scope of the disclosure. Such compounds are useful, for example, as analytical tools or probes in biological assays.

When a range of values ("range") is listed, it encompasses each value and sub-range within the range. A range is inclusive of the values at the two ends of the range unless otherwise provided. For example, "$C_{1-6}$ alkyl" encompasses $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_{1-6}$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., in-propyl, isopropyl), butyl ($C_4$) (e.g., in-butyl, tert-butyl, sec-butyl, isobutyl), pentyl ($C_5$) (e.g., n-pentyl, 3-pentanyl, amyl, neopentyl, 3-methyl-2-butanyl, tert-amyl), and hexyl (C) (e.g., i-hexyl). Additional examples of alkyl groups include i-heptyl ($C_7$), n-octyl ($C^8$), n-dodecyl ($C_{12}$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-12}$ alkyl (such as unsubstituted $C_{1-6}$ alkyl, e.g., $-CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is a substituted $C_{1-12}$ alkyl (such as substituted $C_{1-6}$ alkyl, e.g., $—CH_2F$, $—CHF_2$, $—CF_3$, $—CH_2CH_2F$, $—CH_2CHF_2$, $—CH_2CF_3$, or benzyl (Bn)).

The term "haloalkyl" is a substituted alkyl group, wherein one or more of the hydrogen atoms are independently replaced by a halogen, e.g., fluoro, bromo, chloro, or iodo. "Perhaloalkyl" is a subset of haloalkyl and refers to an alkyl group wherein all of the hydrogen atoms are independently replaced by a halogen, e.g., fluoro, bromo, chloro, or iodo.

The term "heteroalkyl" refers to an alkyl group, which further includes at least one heteroatom (e.g., 1, 2, 3, or 4 heteroatoms) selected from oxygen, nitrogen, or sulfur within (e.g., inserted between adjacent carbon atoms of) and/or placed at one or more terminal position(s) of the parent chain.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 14 ring carbon atoms ("$C_{3-14}$ carbocyclyl"). In some embodiments, a carbocyclyl group has 3 to 13 ring carbon atoms ("$C_{3-13}$ carbocyclyl"). In some embodiments, a carbocyclyl group has 3 to 12 ring carbon atoms ("$C_{1-12}$ carbocyclyl"). In some embodiments, a carbocyclyl group has 3 to 11 ring carbon atoms ("$C_{3-11}$ carbocyclyl"). In some embodiments, a carbocyclyl group has 3 to 10 ring carbon atoms ("$C_{3-10}$ carbocyclyl"). In some embodiments, a carbocyclyl group has 3 to 6 ring carbon atoms ("$C_{3-6}$ carbocyclyl"). Exemplary $C_{3-6}$ carbocyclyl groups include cyclopropyl ($C_3$), cyclopropenyl ($C_3$), cyclobutyl ($C_4$), cyclobutenyl ($C_4$), cyclopentyl ($C^5$), cyclopentenyl ($C^5$), cyclohexyl ($C^6$), cyclohexenyl ($C^6$), cyclohexadienyl ($C^6$), and the like. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "cycloalkyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{4-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl").

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits Exemplary 3-membered heterocyclyl groups containing 1 heteroatom include azirdinyl, oxiranyl, and thiiranyl. Exemplary 4-membered heterocyclyl groups containing 1 heteroatom include azetidinyl, oxetanyl, and thietanyl. Exemplary 5-membered heterocyclyl groups containing 1 heteroatom include tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include dioxolanyl, oxathiolanyl and dithiolanyl. Exemplary 5-membered heterocyclyl groups containing 3 heteroatoms include triazolinyl, oxadiazolinyl, and thiadiazolinyl. Exemplary 6-membered heterocyclyl groups containing 1 heteroatom include piperidinyl, tetrahydropyranyl, dihydropyridinyl, and thianyl. Exemplary 6-membered heterocyclyl groups containing 2 heteroatoms include piperazinyl, morpholinyl, dithianyl, and dioxanyl. Exemplary 6-membered heterocyclyl groups containing 3 heteroatoms include triazinyl. The term "aryl" refers to a radical of a monocyclic or polycyclic (e.g., bicyclic or tricyclic) 4n+2 aromatic ring system (e.g., having 6, 10, or 14 n electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{6-14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

The term "heteroaryl" refers to a radical of a 5-14 membered monocyclic or polycyclic (e.g., bicyclic, tricyclic) 4n+2 aromatic ring system (e.g., having 6, 10, or 14 $\pi$ electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits.

The term "unsaturated bond" refers to a double or triple bond.

The term "unsaturated" or "partially unsaturated" refers to a moiety that includes at least one double or triple bond.

The term "saturated" or "fully saturated" refers to a moiety that does not contain a double or triple bond, e.g., the moiety only contains single bonds.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which is substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted"

or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction.

Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not limited in any manner by the exemplary substituents described herein.

Exemplary carbon atom substituents include halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$X—, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR*)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{bb}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3^+$X$^-$, —P(OR$^{cc}$)$_3^+$X$^-$, —P(R$^{cc}$)$_4$, —P(OR$^{cc}$)$_4$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-20}$ alkyl, C$_{1-20}$ perhaloalkyl, C$_{1-20}$ alkenyl, C$_{1-20}$ alkynyl, heteroC$_{1-20}$ alkyl, heteroC$_{1-20}$ alkenyl, heteroC$_{1-20}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

wherein:

each instance of R$^{aa}$ is, independently, selected from C$_{1-20}$ alkyl, C$_{1-20}$ perhaloalkyl, C$_{1-20}$ alkenyl, C$_{1-20}$ alkynyl, heteroC$_{1-20}$ alkyl, heteroC$_{1-2}$alkenyl, heteroC$_{1-20}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each of the alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{aa}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-20}$ alkyl, C$_{1-20}$ perhaloalkyl, C$_{1-20}$ alkenyl, C$_{1-20}$ alkynyl, heteroC$_{1-20}$alkyl, heteroC$_{1-20}$alkenyl, heteroC$_{1-20}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; each instance of R$^{cc}$ is, independently, selected from hydrogen, C$_{1-20}$ alkyl, C$_{1-20}$ perhaloalkyl, C$_{1-20}$ alkenyl, C$_{1-20}$ alkynyl, heteroC$_{1-20}$ alkyl, heteroC$_{1-20}$ alkenyl, heteroC$_{1-20}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$R$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-10}$ alkyl, C$_{1-10}$ perhaloalkyl, C$_{1-10}$ alkenyl, C$_{1-10}$ alkynyl, heteroC$_{1-10}$alkyl, heteroC$_{1-10}$alkenyl, heteroC$_{1-10}$alkynyl, C$_{3-10}$ carbocyclyl, 3-10 membered heterocyclyl, C$_{6-10}$ aryl, and 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents are joined to form =O or =S; wherein X$^-$ is a counterion;

each instance of R$^{ee}$ is, independently, selected from C$_{1-10}$ alkyl, C$_{1-10}$ perhaloalkyl, C$_{1-10}$ alkenyl, C$_{1-10}$ alkynyl, heteroC$_{1-10}$ alkyl, heteroC$_{1-10}$ alkenyl, heteroC$_{1-10}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; each instance of R$^{ff}$ is, independently, selected from hydrogen, C$_{1-10}$ alkyl, C$_{1-10}$ perhaloalkyl, C$_{1-10}$ alkenyl, C$_{1-10}$ alkynyl, heteroC$_{1-10}$ alkyl, heteroC$_{1-10}$ alkenyl, heteroC$_{1-10}$ alkynyl, C$_{3-10}$ carbocyclyl, 3-10 membered heterocyclyl, C$_{6-10}$ aryl, and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; each instance of $R^{gg}$ is, independently, halogen, —CN, —$NO_2$, —$N_3$, —$SO_2H$, —$SO_3H$, —OH, —$OC_{1-6}$ alkyl, —ON($C_{1-6}$ alkyl)$_2$, —N($C_{1-6}$ alkyl)$_2$, —N($C_{1-6}$ alkyl)$_3$$^+X^-$, —NH($C_{1-6}$ alkyl)$_2$$^+X^-$, —$NH_2$($C_{1-6}$ alkyl)$^+X^-$, —$NH_3^+X^-$, —N($OC_{1-6}$ alkyl)($C_{1-6}$ alkyl), —N(OH)$C_{1-6}$ alkyl), —NH(OH), —SH, —$SC_{1-6}$ alkyl, —SS($C_{1-6}$ alkyl), —C(═O)($C_{1-6}$ alkyl), —$CO_2H$, —$CO_2$($C_{1-6}$ alkyl), —OC(═O)($C_{1-6}$ alkyl), —$OCO_2$($C_{1-6}$ alkyl), —C(═O)$NH_2$, —C(═O)N($C_{1-6}$ alkyl)$_2$, —OC(═O)NH($C_{1-6}$ alkyl), —NHC(═O)($C_{1-6}$ alkyl), —N($C_{1-6}$ alkyl)C(═O)($C_{1-6}$ alkyl), —$NHCO_2$($C_{1-6}$ alkyl), —NHC(═O)N($C_{1-6}$ alkyl)$_2$, —NHC(═O)NH($C_{1-6}$ alkyl), —NHC(═O)$NH_2$, —C(═NH)O($C_{1-6}$ alkyl), —OC(═NH)($C_{1-6}$ alkyl), —OC(═NH)$OC_{1-6}$ alkyl, —C(═NH)N($C_{1-6}$ alkyl)$_2$, —C(═NH)NH($C_{1-6}$ alkyl), —C(═NH)$NH_2$, —OC(═NH)N($C_{1-6}$ alkyl)$_2$, —OC(NH)NH($C_{1-6}$ alkyl), —OC(NH)$NH_2$, —NHC(NH)N($C_{1-6}$ alkyl)$_2$, —NHC(═NH)$NH_2$, —$NHSO_2$($C_{1-6}$ alkyl), —$SO_2N$($C_{1-6}$ alkyl)$_2$, —$SO_2NH$($C_{1-6}$ alkyl), —$SO_2NH_2$, —$SO_2C_{1-6}$ alkyl, —$SO_2C_{1-6}$ alkyl, —$OSO_2C_{1-6}$ alkyl, —$SOC_{1-6}$ alkyl, —Si($C_{1-6}$ alkyl)$_3$, —OSi($C_1$-alkyl)$_3$-C(═S)N($C_{1-6}$ alkyl)$_2$, C(═S)NH($C_{1-6}$ alkyl), C(═S)$NH_2$, —C(═O)S($C_{1-6}$ alkyl), —C(═S)$SC_{1-6}$ alkyl, —SC(═S)$SC_{1-6}$ alkyl, —P(═O)($OC_{1-6}$ alkyl)$_2$, —P(═O)($C_{1-6}$ alkyl)$_2$, —OP(═O)($C_{1-6}$ alkyl)$_2$, —OP(═O)($OC_{1-6}$ alkyl)$_2$, $C_{1-10}$ alkyl, $C_{1-10}$ perhaloalkyl, $C_{1-10}$ alkenyl, $C_{1-10}$ alkynyl, hetero$C_{1-10}$ alkyl, hetero$C_{1-10}$ alkenyl, hetero$C_{1-10}$ alkynyl, $C_{3-10}$ carbocyclyl, $C_{6-10}$ aryl, 3-10 membered heterocyclyl, or 5-10 membered heteroaryl; or two geminal $R^{99}$ substituents can be joined to form ═O or ═S; and each $X^-$ is a counterion.

In certain embodiments, each carbon atom substituent is independently halogen, substituted (e.g., substituted with one or more halogen) or unsubstituted $C_{1-6}$ alkyl, —$OR^{aa}$, —$SR^{aa}$, —N($R^{bb}$)$_2$, —CN, —SCN, —$NO_2$, —C(═O)$R^{aa}$, —$CO_2R^{aa}$, —C(═O)N($R^{bb}$)$_2$, —OC(═O)$R^{aa}$, —$OCO_2R^{aa}$, —OC(═O)N($R^{bb}$)$_2$, —$NR^{bb}$C(═O)$R^{aa}$, —$NR^{bb}CO_2R^{aa}$, or —$NR^{bb}$C(═O)N($R^{bb}$)$_2$. In certain embodiments, each carbon atom substituent is independently halogen, substituted (e.g., substituted with one or more halogen) or unsubstituted $C_{1-10}$ alkyl, —$OR^{aa}$, —$SR^{aa}$, —N($R^{bb}$)$_2$, —CN, —SCN, —$NO_2$, —C(═O)$R^{aa}$, —$CO_2R^{aa}$, —C(═O)N($R^{bb}$)$_2$, —OC(═O)$R^{aa}$, —$OCO_2R^{aa}$, —OC(═O)N($R^{bb}$)$_2$, —$NR^{bb}$C(═O)$R^{aa}$, —$NR^{bb}CO_2R^{aa}$, or —NRC(═O)N($R^{bb}$)$_2$, wherein $R^{aa}$ is hydrogen, substituted (e.g., substituted with one or more halogen) or unsubstituted $C_{1-10}$ alkyl, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each $R^{bb}$ is independently hydrogen, substituted (e.g., substituted with one or more halogen) or unsubstituted $C_{1-10}$ alkyl, or a nitrogen protecting group (e.g., Bn, Boc, Cbz, Fmoc, trifluoroacetyl, triphenylmethyl, acetyl, or Ts). In certain embodiments, each carbon atom substituent is independently halogen, substituted (e.g., substituted with one or more halogen) or unsubstituted $C_{1-6}$ alkyl, —$OR^{aa}$, —$SR^{aa}$, —N($R^{bb}$)$_2$, —CN, —SCN, or —$NO_2$. In certain embodiments, each carbon atom substituent is independently halogen, substituted (e.g., substituted with one or more halogen moieties) or unsubstituted $C_{1-10}$ alkyl, —$OR^{aa}$, —$SR^{aa}$, —N($R^{bb}$)$_2$, —CN, —SCN, or —$NO_2$, wherein $R^{aa}$ is hydrogen, substituted (e.g., substituted with one or more halogen) or unsubstituted $C_{1-10}$ alkyl, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each $R^{bb}$ is independently hydrogen, substituted (e.g., substituted with one or more halogen) or unsubstituted $C_{1-10}$ alkyl, or a nitrogen protecting group (e.g., Bn, Boc, Cbz, Fmoc, trifluoroacetyl, triphenylmethyl, acetyl, or Ts).

In certain embodiments, the molecular weight of a carbon atom substituent is lower than 250, lower than 200, lower than 150, lower than 100, or lower than 50 g/mol. In certain embodiments, a carbon atom substituent consists of carbon, hydrogen, fluorine, chlorine, bromine, iodine, oxygen, sulfur, nitrogen, and/or silicon atoms. In certain embodiments, a carbon atom substituent consists of carbon, hydrogen, fluorine, chlorine, bromine, iodine, oxygen, sulfur, and/or nitrogen atoms. In certain embodiments, a carbon atom substituent consists of carbon, hydrogen, fluorine, chlorine, bromine, and/or iodine atoms. In certain embodiments, a carbon atom substituent consists of carbon, hydrogen, fluorine, and/or chlorine atoms.

The term "halo" or "halogen" refers to fluorine (fluoro, —F), chlorine (chloro, —Cl), bromine (bromo, —Br), or iodine (iodo, —I).

Nitrogen atoms can be substituted or unsubstituted as valency permits, and include primary, secondary, tertiary, and quaternary nitrogen atoms. Exemplary nitrogen atom substituents include hydrogen, —OH, —$OR^{aa}$, —N($R^{cc}$)$_2$, —CN, —C(═O)$R^{aa}$, —C(═O)N($R^{cc}$)$_2$, —$CO_2R$, —$SO_2R^{aa}$, —C(═$NR^{bb}$)$R^{aa}$, —C(═$NR^{cc}$)$OR^{aa}$, —C(═$NR^{cc}$)N($R^{cc}$)$_2$, —$SO_2N$($R^{cc}$)$_2$, —$SO_2R^{cc}$, —$SO_2OR^{cc}$, —$SOR^{aa}$, —C(═S)N($R^{cc}$)$_2$, —C(═O)$SR^{cc}$, —C(═S)$SR^{cc}$, —P(═O)($OR^{cc}$)$_2$, —P(═O)($R^{aa}$)$_2$, —P(═O)(N($R^{cc}$)$_2$)$_2$, $C_{1-20}$ alkyl, $C_{1-20}$ perhaloalkyl, $C_{1-20}$ alkenyl, $C_{1-20}$ alkynyl, hetero $C_{1-20}$ alkyl, hetero $C_{1-20}$alkenyl, hetero $C_{1-20}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, each nitrogen atom substituent is independently substituted (e.g., substituted with one or more halogen) or unsubstituted $C_{1-6}$ alkyl, —C(═O)$R^{aa}$, —$CO_2R$, —C(═O)N($R^{bb}$)$_2$, or a nitrogen protecting group. In certain embodiments, each nitrogen atom substituent is independently substituted (e.g., substituted with one or more halogen) or unsubstituted $C_{1-10}$ alkyl, —C(═O)$R^{aa}$, —$CO_2R^{aa}$, —C(═O)N($R^{bb}$)$_2$, or a nitrogen protecting group, wherein $R^{aa}$ is hydrogen, substituted (e.g., substituted with one or more halogen) or unsubstituted $C_{1-10}$ alkyl, or an oxygen protecting group when attached to an oxygen atom;

and each $R^{bb}$ is independently hydrogen, substituted (e.g., substituted with one or more halogen) or unsubstituted $C_{1-10}$ alkyl, or a nitrogen protecting group. In certain embodiments, each nitrogen atom substituent is independently substituted (e.g., substituted with one or more halogen) or unsubstituted $C_{1-6}$ alkyl or a nitrogen protecting group.

In certain embodiments, the substituent present on the nitrogen atom is a nitrogen protecting group (also referred to herein as an "amino protecting group"). Nitrogen protecting groups include —OH, —$OR^{aa}$, —$N(R^{cc})_2$, —$C(=O)R^{aa}$, —$C(=O)N(R^{cc})_2$, —$CO_2R^{aa}$, —$SO_2R^{aa}$, —$C(=NR^{cc})R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2R^{cc}$, —$SOR^{aa}$, —$C(=S)N(R^{cc})_2$, —$C(=O)SR^{aa}$, —$C(=S)SR^{cc}$, $C_{1-10}$ alkyl (e.g., aralkyl, heteroaralkyl), $C_{1-20}$ alkenyl, $C_{1-20}$ alkynyl, hetero $C_{1-20}$ alkyl, hetero $C_{1-20}$ alkenyl, hetero $C_{1-20}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

For example, in certain embodiments, at least one nitrogen protecting group is an amide group (e.g., a moiety that include the nitrogen atom to which the nitrogen protecting groups (e.g., —$C(=O)R^{aa}$) is directly attached). In certain such embodiments, each nitrogen protecting group, together with the nitrogen atom to which the nitrogen protecting group is attached, is independently selected from the group consisting of formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivatives, benzamide, p-phenylbenzamide, o-nitophenylacetamide, o-nitrophenoxyacetamide, acetoacetamide, (N'-dithiobenzyloxyacylamino) acetamide, 3-(p-hydroxyphenyl)propanamide, 3-(0-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivatives, o-nitrobenzamide, and o-(benzoyloxymethyl) benzamide.

In certain embodiments, at least one nitrogen protecting group is a carbamate group (e.g., a moiety that include the nitrogen atom to which the nitrogen protecting groups (e.g., —$C(=O)OR^{aa}$) is directly attached). In certain such embodiments, each nitrogen protecting group, together with the nitrogen atom to which the nitrogen protecting group is attached, is independently selected from the group consisting of methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, 5-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

In certain embodiments, at least one nitrogen protecting group is a sulfonamide group (e.g., a moiety that include the nitrogen atom to which the nitrogen protecting groups (e.g., —$S(=O)_2R^{aa}$) is directly attached). In certain such embodiments, each nitrogen protecting group, together with the nitrogen atom to which the nitrogen protecting group is attached, is independently selected from the group consisting of p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

In certain embodiments, each nitrogen protecting group, together with the nitrogen atom to which the nitrogen protecting group is attached, is independently selected from the group consisting of phenothiazinyl-(10)-acyl derivatives, N'-p-toluenesulfonylaminoacyl derivatives, N'-phenylaminothioacyl derivatives, N-benzoylphenylalanyl derivatives, N-acetylmethionine derivatives, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivatives, N-diphenylborinic acid derivatives, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys). In some embodiments, two instances of a nitrogen protecting group together with the nitrogen atoms to which the nitrogen protecting groups are attached are N,N'-isopropylidenediamine.

In certain embodiments, at least one nitrogen protecting group is Bn, Boc, Cbz, Fmoc, trifluoroacetyl, triphenylmethyl, acetyl, or Ts.

In certain embodiments, each oxygen atom substituent is independently substituted (e.g., substituted with one or more halogen) or unsubstituted $C_{1-10}$ alkyl, —C(═O)$R^{aa}$, —$CO_2R^{aa}$, —C(═O)N($R^{bb}$)$_2$, or an oxygen protecting group. In certain embodiments, each oxygen atom substituents is independently substituted (e.g., substituted with one or more halogen) or unsubstituted $C_{1-6}$ alkyl, —C(═O)$R^1$, —$CO_2R^{aa}$, —C(═O)N($R^{bb}$)$_2$, or an oxygen protecting group, wherein $R^{aa}$ is hydrogen, substituted (e.g., substituted with one or more halogen) or unsubstituted $C_{1-10}$ alkyl, or an oxygen protecting group when attached to an oxygen atom; and each $R^{bb}$ is independently hydrogen, substituted (e.g., substituted with one or more halogen) or unsubstituted $C_{1-10}$ alkyl, or a nitrogen protecting group. In certain embodiments, each oxygen atom substituent is independently substituted (e.g., substituted with one or more halogen) or unsubstituted $C_{1-6}$ alkyl or an oxygen protecting group.

In certain embodiments, the substituent present on an oxygen atom is an oxygen protecting group (also referred to herein as an "hydroxyl protecting group"). Oxygen protecting groups include —$R^{aa}$, —N($R^{bb}$)$_2$, —C(═O)S$R^{aa}$, —C(═O)$R^{aa}$, —$CO_2R^{aa}$, —C(═O)N($R^{bb}$)$_2$, —C(═N$R^{bb}$)$R^{aa}$, —C(═N$R^{bb}$)O$R^{aa}$, —C(═N$R^{bb}$)N($R^{bb}$)$_2$, —S(═O)$R^{aa}$, —$SO_2R^{aa}$, —Si($R^{aa}$)$_3$, —P($R^{cc}$)$_2$, —P($R^{cc}$)$_3^+X^-$, —P(O$R^{cc}$)$_2$, —P(O$R^{cc}$)$_3^+X^-$, —P(═O)($R^{cc}$)$_2$, —P(═O)(O$R^{cc}$)$_2$, and —P(═O)(N($R^{bb}$)$_2$)$_2$, wherein $X^-$, $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

In certain embodiments, each oxygen protecting group, together with the oxygen atom to which the oxygen protecting group is attached, is selected from the group consisting of methyl, methoxymethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl (PMB), 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, pp'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 4,4'-Dimethoxy-3'"-[N-(imidazolylmethyl)]trityl Ether (IDTr-OR), 4,4'-Dimethoxy-3'"-[N-(imidazolylethyl)carbamoyl]trityl Ether (IETr-OR), 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate (MTMEC-OR), 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, at least one oxygen protecting group is silyl, TBDPS, TBDMS, TIPS, TES, TMS, MOM, THP, t-Bu, Bn, allyl, acetyl, pivaloyl, or benzoyl.

In certain embodiments, the molecular weight of a substituent is lower than 250, lower than 200, lower than 150, lower than 100, or lower than 50 g/mol. In certain embodiments, a substituent consists of carbon, hydrogen, fluorine, chlorine, bromine, iodine, oxygen, sulfur, nitrogen, and/or silicon atoms. In certain embodiments, a substituent consists of carbon, hydrogen, fluorine, chlorine, bromine, iodine, oxygen, sulfur, and/or nitrogen atoms. In certain embodiments, a substituent consists of carbon, hydrogen, fluorine, chlorine, bromine, and/or iodine atoms. In certain embodiments, a substituent consists of carbon, hydrogen, fluorine, and/or chlorine atoms. In certain embodiments, a substituent comprises 0, 1, 2, or 3 hydrogen bond donors. In certain embodiments, a substituent comprises 0, 1, 2, or 3 hydrogen bond acceptors.

A "counterion" or "anionic counterion" is a negatively charged group associated with a positively charged group in order to maintain electronic neutrality. An anionic counterion may be monovalent (e.g., including one formal negative charge). An anionic counterion may also be multivalent (e.g., including more than one formal negative charge), such as divalent or trivalent.

Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbFb^-$, $B[3,5^-(CF_3)_2C_6H_3]_4]^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^-$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

Use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" refers to any group that is defined for a particular variable that is not hydrogen.

These and other exemplary substituents are described in more detail in the Detailed Description, Examples, and Claims. The invention is not limited in any manner by the above exemplary listing of substituents.

As used herein, the term "salt" refers to any and all salts and encompasses pharmaceutically acceptable salts. Salts include ionic compounds that result from the neutralization reaction of an acid and a base. A salt is composed of one or more cations (positively charged ions) and one or more anions (negative ions) so that the salt is electrically neutral (without a net charge). Salts of the compounds of this invention include those derived from inorganic and organic acids and bases. Examples of acid addition salts are salts of an amino group formed with inorganic acids, such as hydrochloric acid, hydrobromic acid, phosphoric acid, sulfuric acid, and perchloric acid, or with organic acids, such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate, hippurate, and the like. Salts derived from appropriate bases include alkali metal, alkaline earth metal, ammonium and $N'(C_{1-4}\ alkyl)_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

As used herein, the term "work up" refers to any single step or series of multiple steps relating to isolating and/or purifying one or more products of a chemical reaction (e.g., from any remaining starting material, other reagents, solvents, or byproducts of the chemical reaction). Working up a reaction may include removing solvents by, for example, evaporation or lyophilization. Working up a reaction may also include performing liquid-liquid extraction, for example, by separating the reaction mixture into organic and aqueous layers. In some embodiments, working up a reaction includes quenching the reaction to deactivate any unreacted reagents. Working up a reaction may also include cooling a reaction mixture to induce precipitation of solids from the mixture, which may be collected or removed by, for example, filtration, decantation, or centrifugation. Working up a reaction can also include purifying one or more products of the reaction by chromatography. Other methods may also be used to purify one or more reaction products, including, but not limited to, distillation and recrystallization.

Other processes for working up a reaction are known in the art, and a person of ordinary skill in the art would readily be capable of determining other appropriate methods that could be employed in working up a particular reaction.

As used herein, the term "about X," or "approximately X," where X is a number or percentage, refers to a number or percentage that is between 99.5% and 100.5%, between 99% and 101%, between 98% and 102%, between 97% and 103%, between 96% and 104%, between 95% and 105%, between 92% and 108%, or between 90% and 110%, inclusive, of X.

DETAILED DESCRIPTION OF CERTAIN EMBODIMENTS

The aspects described herein are not limited to specific embodiments, systems, compositions, methods, or configurations, and as such can, of course, vary. The terminology used herein is for the purpose of describing particular aspects only and, unless specifically defined herein, is not intended to be limiting.

Methods for Synthesizing a Trinucleotide

In one aspect, provided herein are methods for synthesizing a trinucleotide comprising reacting a compound, or salt thereof, of formula (4) with a compound, or salt thereof, of formula (5) to obtain a compound, or salt thereof, of formula (6):

(4)

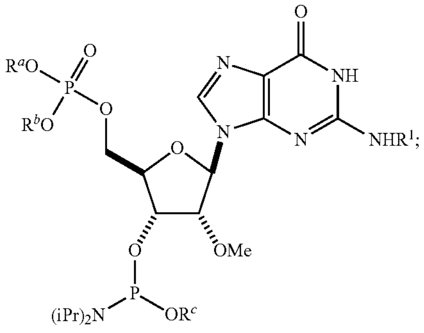

(5)

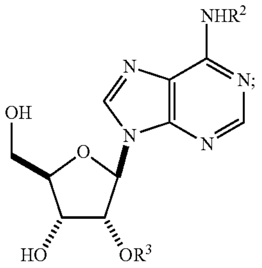

and

-continued (6)

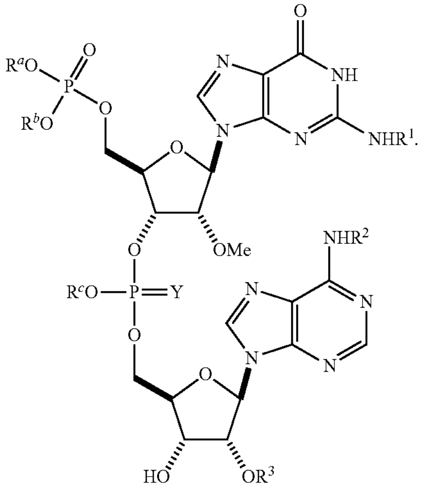

In certain embodiments, the compound, of formula (6) may then be reacted with a compound, or salt thereof, of formula (10) to obtain a compound, or salt thereof, or formula (11):

(10)

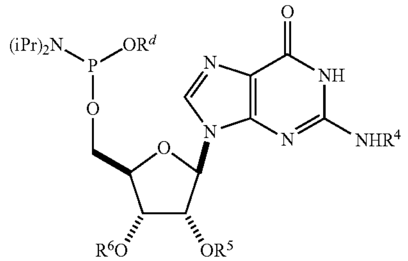

and (11)

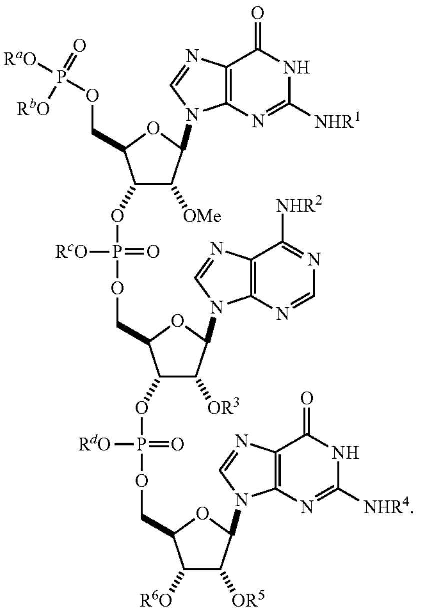

In the compounds disclosed herein, $R^1$ may be a nitrogen protecting group (e.g., any nitrogen protecting group disclosed herein). In some embodiments, $R^1$ is an acyl nitrogen protecting group (e.g., an acyl group compatible with acidic conditions that can be removed by base treatment). In certain embodiments, $R^1$ is an alkyl group, such as an iso-butyl group.

The moieties $R^a$, $R^b$, and $R^c$ in the compounds disclosed herein may each independently be an oxygen protecting group. In certain embodiments, $R^a$ is a 2-cyanoethyl group. In certain embodiments, $R^b$ is a 2-cyanoethyl group. In certain embodiments, $R^c$ is a 2-cyanoethyl group. All three of $R^a$, $R^b$, and $R^c$ may be 2-cyanoethyl groups. In some embodiments, $R^1$ is iso-butyl and $R^a$, $R^b$, and $R^c$ are all 2-cyanoethyl groups. For example, the compound of formula (4) may be a compound having the following structure:

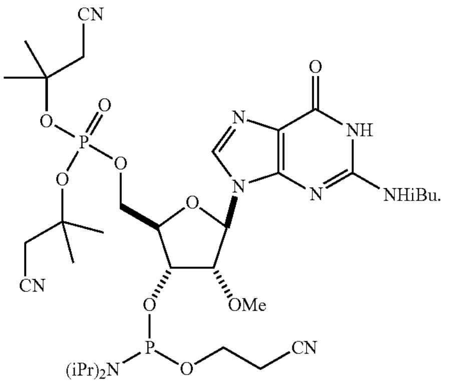

The moiety $R^2$ in the compounds disclosed herein may also independently be any of the nitrogen protecting groups disclosed herein. In some embodiments, $R^2$ is an acyl nitrogen protecting group (e.g., an acyl group compatible with acidic conditions that can be removed by base treatment). In a particular embodiment, $R^2$ is benzoyl. In some embodiments, $R^2$ is an alkyl group.

The moiety $R^3$ in the compounds disclosed herein may be any of the oxygen protecting group disclosed herein. In some embodiments, $R^3$ is an O-acyl protecting group (e.g., a pivalic acid ester). For example, the compound of formula (5) may be a compound having the following structure:

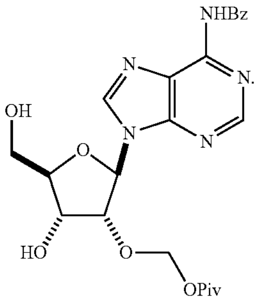

The compounds disclosed herein may also include a moiety Y. In some embodiments, Y is O. In certain embodiments, Y is absent. For example, the compound of formula (6) may be a compound of the following structure:

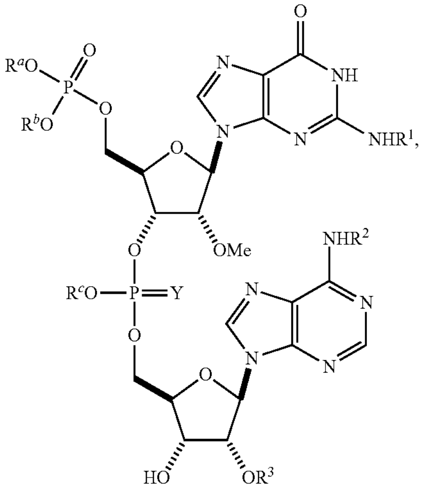

where Y is either O or absent. In certain embodiments, the compound of formula (6) is a compound having the following structure:

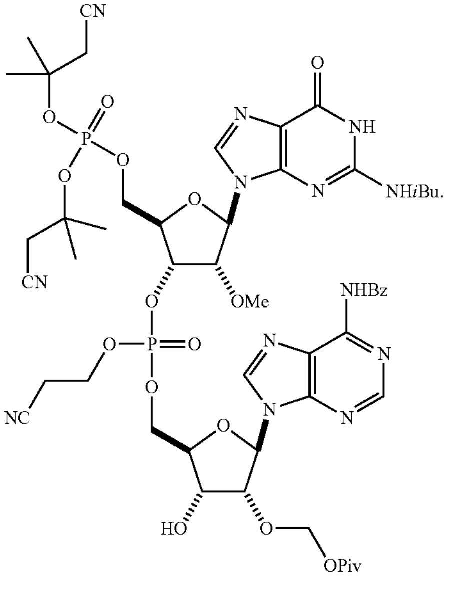

The compounds disclosed herein may include a moiety $R^4$. $R^4$ may be a nitrogen protecting group (e.g., any of the nitrogen protecting groups disclosed herein). In some embodiments, $R^4$ is an acyl nitrogen protecting group (e.g., an acyl group compatible with acidic conditions that can be removed by base treatment). In certain embodiments, $R^4$ is an alkyl group. In a particular embodiment, $R^4$ is isobutyl.

The compounds disclosed herein may also include the moieties $R^5$, $R^6$, and $R^d$. In some embodiments, $R^5$, $R^6$, and $R^d$ are each independently an oxygen protecting group. The moieties $R^5$ and $R^6$ in the compounds disclosed herein may be any of the oxygen protecting groups disclosed herein. In some embodiments, $R^5$ and $R^6$ are each independently an O-acyl protecting group. In certain embodiments, $R^5$ and $R^6$ may each independently be alkyl (e.g., iso-butyl). In certain embodiments, $R^d$ is a 2-cyanoethyl group. In some embodiments, $R^5$ and $R^6$ are each iso-butyl and $R^d$ is 2-cyanoethyl. For example, the compound of formula (10) may be a compound having the following structure:

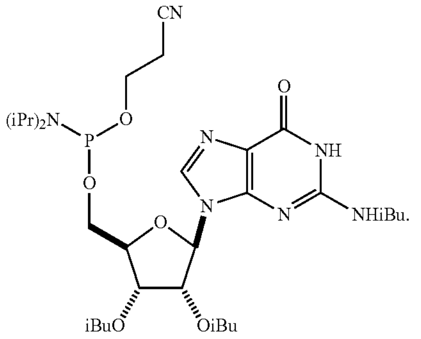

In some embodiments, the compound of Formula (11) may be of the following structure:

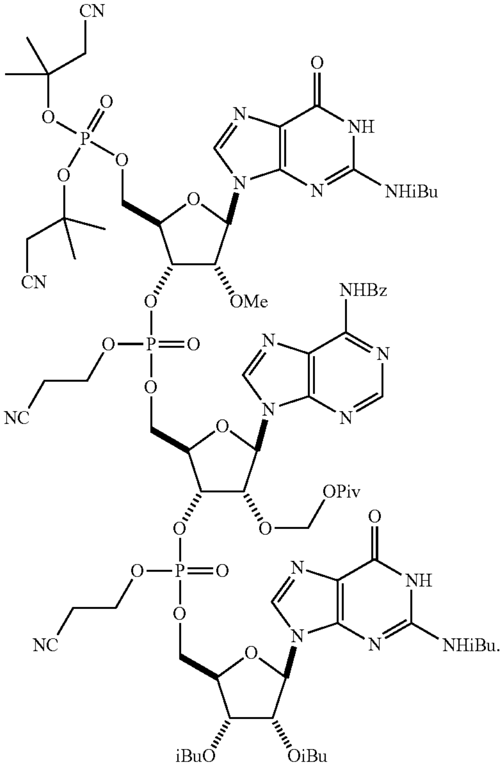

Reacting a compound of formula (4) with a compound of formula (5) to obtain a compound of formula (6) may be performed in the presence of an activator. For example, an acid activator may be used to activate a diisopropylamino group in a compound, such as the diisopropyl group in the compound of formula (4). Upon acid activation, the diisoproylamino group acts as a leaving group and is substituted by the 5'-hydroxy group of another molecule, such as the 5'-hydroxy group of the compound of formula (5). In some embodiments, the acid activator is a weak acid (e.g., an acid that partially dissociates when it is dissolved in a solvent). Exemplary acid activators that can be used in the methods described herein include, but are not limited to, pyridine trifluoroacetate, 1H-tetrazole, diisopropylammonium tetrazolide, 5-(Ethylthio)-1H-tetrazole, and 4,5-dicyanoimidazole. In some embodiments, the acid activator used in the methods described herein is pyridine trifluoroacetate. The acid activator may also be provided as a solution. In certain embodiments, the acid activator is pyridine trifluoroacetate and is provided as a solution in pyridine.

Each step of the methods disclosed herein may be performed in the presence of various solvents. For example, the reaction of a compound of formula (4) with a compound of formula (5) to obtain a compound of formula (6) may be performed in the presence of a solvent. Suitable solvents for performing this reaction include, but are not limited to, pyridine, acetonitrile, dichloromethane, tetrahydrofuran, and dimethylformamide. In some embodiments, the reaction of a compound of formula (4) and a compound of formula (5) is performed in pyridine.

Various conditions are suitable for the reaction of a compound of formula (4) with a compound of formula (5) to obtain a compound of formula (6), and one of ordinary skill in the art will readily understand that such conditions may be substituted and still be compatible using the methods disclosed herein. For example, such a reaction may be performed for varying amounts of time. The reaction may comprise a reaction time of approximately 0.5 hours, approximately 1 hour, approximately 1.5 hours, approximately 2 hours, approximately 2.5 hours, approximately 3 hours, approximately 3.5 hours, approximately 4 hours, approximately 4.5 hours, or approximately 5 hours. In some embodiments, the reaction of a compound of formula (4) and a compound of formula (5) is performed for a reaction time of approximately 2-3 hours.

Various molar ratios of the reagents to one another may also be used in the reactions of the methods disclosed herein. For example, the ratio of a compound of formula (5) and a compound of formula (4) in the reaction to obtain a compound of formula (6) may be approximately 1:0.5, approximately 1:0.6, approximately 1:0.7, approximately 1:0.8, approximately 1:0.9, approximately 1:1, approximately 1:1.1, approximately 1:1.2, approximately 1:1.3, approximately 1:1.4, approximately 1:1.5, approximately 1:1.6, approximately 1:1.7, approximately 1:1.8, approximately 1:1.9, or approximately 1:2. In some embodiments, a ratio greater than 1:2 may be used. In certain embodiments, a ratio of approximately 1:1.4 is used. The ratio of a compound of formula (5) to the acid activator may be approximately 1:1, approximately 1:1.5, approximately 1:2, approximately 1:2.5, approximately 1:3, approximately 1:3.5, approximately 1:4, approximately 1:4.5, or approximately 1:5. In certain embodiments, the ratio of the compound of formula (5) and the acid activator is approximately 1:2.

Various temperatures may also be employed in such a reaction. For example, prior to adding the acid activator, the reaction of the compound of formula (4) and the compound of formula (5) may comprise a reaction temperature of approximately −30° C., approximately −25° C., approximately −20° C., approximately −15° C., approximately −10° C., approximately −5° C., approximately 0° C., approximately 5° C., or approximately 10° C. In certain embodiments, reaction of the compound of formula (4) and the compound of formula (5) comprises a temperature of approximately −10° C. prior to adding the acid activator. In some embodiments, the temperature of the reaction prior to the addition of the acid activator and after adding the acid activator are the same. The temperature of the reaction prior to addition of the acid activator and after adding the acid activator may also be different from one another. For example, the temperature of the reaction after adding the acid activator may be in a range of approximately −30° C. to approximately 30° C., approximately −25° C. to approximately 25° C., approximately −20° C. to approximately 20° C., approximately −15° C. to approximately 15° C., approximately −10° C. to approximately 10° C., or approximately −5° C. to approximately 5° C. In some embodiments, the temperature after adding the acid activator is in the range of approximately −3° C. to approximately 5° C.

One-Pot Reaction Process

According to the methods disclosed herein, reaction of a compound of formula (4) with a compound of formula (5) may include an oxidant. In some embodiments, such a reaction does not comprise an oxidant. For example, such a reaction may not comprise an oxidant and thereby result in the production of a compound of formula (6-a):

(6-a)

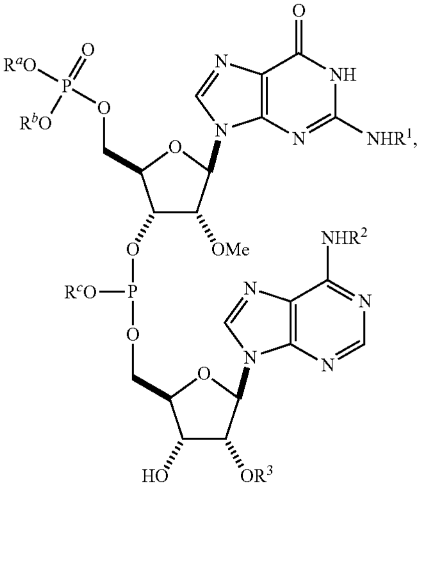

wherein $R^1$, $R^2$, $R^3$, $R^a$, $R^b$, and $R^c$ are as defined herein.

A compound of formula (6) may be isolated, or not isolated, prior to reaction with a compound of formula (10). In some embodiments, a compound of formula (6-a), produced when an oxidant is not used, is not isolated prior to reaction with a compound of formula (10). This process is referred to herein as a "one-pot" reaction (e.g., multiple steps are performed within the same reaction vessel without isolation of an intermediate). A one-pot reaction may have several advantages over a corresponding reaction sequence comprising isolation of the intermediate compound (e.g., a "stepwise" reaction). For example, a one-pot reaction may result in a decrease in the amount of time necessary to perform the methods disclosed herein (e.g., by eliminating time needed for work-up or purification of an intermediate compound that is not isolated in the one-pot method). A one-pot reaction may also mitigate the partial or complete loss of protecting groups on the intermediate that may occur under work-up or purification conditions. Such a reaction may also result in an improved overall throughput or yield relative to a corresponding stepwise process. For example, the one-pot reaction strategy utilized in some of the methods disclosed herein may result in an improvement of the reaction yield from about 30-40% to about 45%, about 50%, about 55%, about 56%, about 57%, about 58%, about 59%, about 60%, or greater than about 60%. In some embodiments, use of a one-pot reaction strategy in the methods disclosed herein results in an overall yield improvement from about 30-40% to approximately 60%.

Using the one-pot approach described herein, a compound of formula (6-a) may be directly reacted with a compound of formula (10), without isolation, to obtain a compound of formula (11-a):

(11-a)

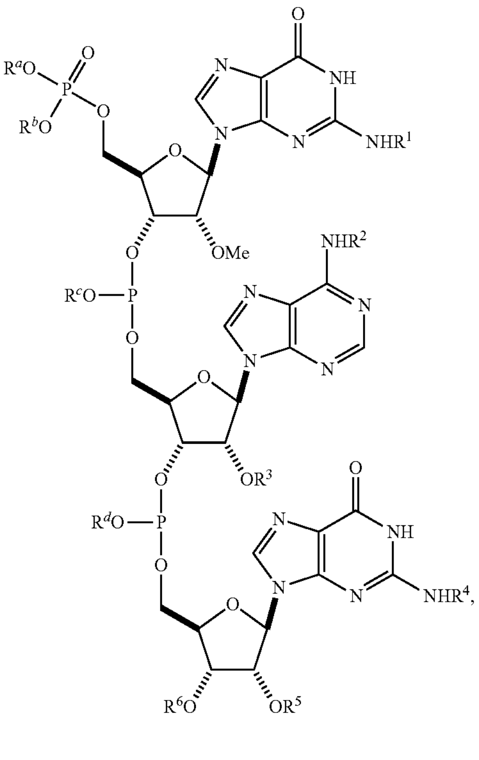

wherein $R^1$, $R^2$, $R^3$, $R^4$, $R^5$, $R^6$, $R^a$, $R^b$, $R^c$, and $R^d$ are as defined herein.

In some embodiments, the compound of formula (11-a) has the structure:

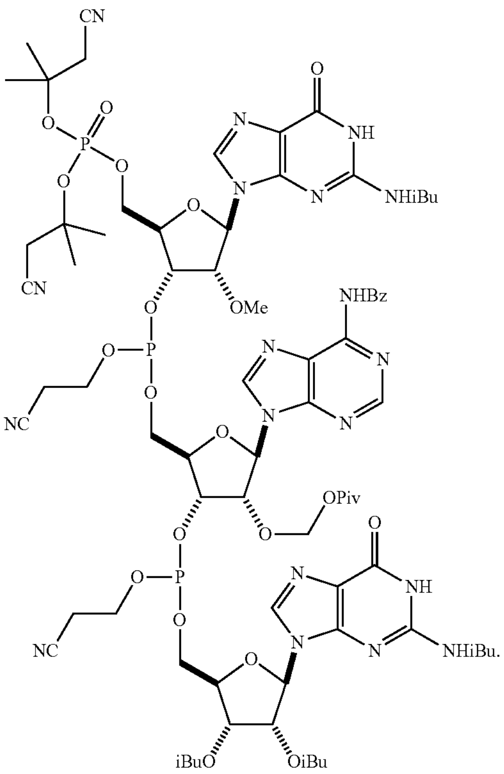

The compound of formula (11-a) may then be oxidized to obtain a compound of formula (11). Oxidation of a compound of formula (11-a) may be accomplished in the presence of an oxidant. Oxidants, also referred to as oxidizers or oxidizing agents, are substances that are capable of accepting electrons from another substance (e.g., oxidizing the other substance).

Suitable oxidants for use in the methods disclosed herein (i.e., for oxidation of P(III) to P(V)) are well known and will be readily apparent to those skilled in the art (e.g., those disclosed in Connelly, N. G. and Geiger, W. E. *Chem. Rev.* 1996, 96, 877-910). An oxidant used in the methods disclosed herein may be an inorganic oxidant. Suitable inorganic oxidants include, but are not limited to, iodine, hydrogen peroxide, oxygen gas, and ozone. Oxidants used in the methods disclosed herein may also be organic oxidants, e.g., organic peroxides. Suitable organic peroxides include, but are not limited to, hydroperoxides (e.g., peroxides with the general structure ROOH, wherein R is an organic group, such as an alkyl hydroperoxide), peroxy acids (e.g., peroxides with the general structure RC(═O)OOH, wherein R is an organic group, such as an alkyl peroxy acid), diacyl peroxides (e.g., peroxides with the general structure RC(═O)OOC(═O)R, where each R is independently an organic group, such as an alkyl diacyl peroxide or an aryl diacyl peroxide), and dialkylperoxides (e.g., peroxides with the general structure ROOR, where each R is independently an alkyl group). In some embodiments, a hydroperoxide is used in the methods disclosed herein. In some embodiments, the hydroperoxide is methyl hydroperoxide, ethyl hydroperoxide, n-propyl hydroperoxide, isopropyl hydroperoxide, n-butyl hydroperoxide, iso-butyl hydroperoxide, or tert-butyl hydroperoxide. In certain embodiments, the oxidant used in the methods disclosed herein is tert-butyl hydroperoxide.

Various conditions are suitable for the reaction of a compound of formula (6-a) with a compound of formula (10) to obtain a compound of formula (11), and one of ordinary skill in the art will readily understand that such conditions may be substituted and still be compatible with the methods disclosed herein. For example, such a reaction may be performed for varying amounts of time. Such a reaction may comprise a reaction time of approximately 0.5 hours, approximately 1 hour, approximately 1.5 hours, approximately 2 hours, approximately 2.5 hours, approximately 3 hours, approximately 3.5 hours, approximately 4 hours, approximately 4.5 hours, approximately 5 hours, approximately 5.5 hours, approximately 6 hours, or more than approximately 6 hours prior to adding the oxidant. In some embodiments, the reaction of a compound of formula (6-a) and a compound of formula (10) is performed for a reaction time of approximately 3-5 hours prior to adding the oxidant. After adding the oxidant, the reaction may comprise a reaction time of approximately 1-48 hours, approximately 2-44 hours, approximately 4-40 hours, approximately 6-36 hours, approximately 8-32 hours, approximately 10-28 hours, or approximately 12-24 hours. In certain embodiments, the reaction comprises a reaction time of approximately 12-24 hours after adding the oxidant.

Various molar ratios of the reagents to one another may also be used in the reactions of the methods disclosed herein. For example, the ratio of a compound of formula (6-a) and a compound of formula (10) in the reaction to obtain a compound of formula (6) may be approximately 1:0.5, approximately 1:0.6, approximately 1:0.7, approximately 1:0.8, approximately 1:0.9, approximately 1:1, approximately 1:1.1, approximately 1:1.2, approximately 1:1.3, approximately 1:1.4, approximately 1:1.5, approximately 1:1.6, approximately 1:1.7, approximately 1:1.8, approximately 1:1.9, or approximately 1:2. In some embodiments, a ratio greater than 1:2 may be used. In certain embodiments, a ratio of approximately 1:1.6 is used. The ratio of a compound of formula (6-a) to the acid activator may be approximately 1:1, approximately 1:1.5, approximately 1:2, approximately 1:2.5, approximately 1:3, approximately 1:3.5, approximately 1:4, approximately 1:4.5, or approximately 1:5. In certain embodiments, the ratio of the compound of formula (5) and the acid activator is approximately 1:2. The ratio of the compound of formula (6-a) to the oxidant may be approximately 1:1, approximately 1:1.5, approximately 1:2, approximately 1:2.5, approximately 1:3, approximately 1:3.5, approximately 1:4, approximately 1:4.5, or approximately 1:5. In some embodiments, a ratio of greater than 1:5 is used. In certain embodiments, the ratio of the compound of formula (6-a) and the oxidant used in the methods disclosed herein is approximately 1:3.

Various temperatures may also be employed in such a reaction. For example, the reaction of the compound of formula (6-a) and the compound of formula (10) may comprise a reaction temperature in the range of approximately −15° C. to approximately 30° C., approximately −10° C. to approximately 25° C., approximately −5° C. to approximately 20° C., or approximately 0° C. to approximately 15° C. In certain embodiments, reaction of the compound of formula (6-a) and the compound of formula (10) comprises a temperature in the range of approximately 0° C. to approximately 14° C.

Stepwise Reaction Process

Reaction of a compound of formula (4) and a compound of formula (5) to obtain a compound of formula (6) may comprise the use of an oxidant. When an oxidant is used in the reaction of a compound of formula (4) with a compound of formula (5), a compound of formula (6-b) may be produced:

(6-b)

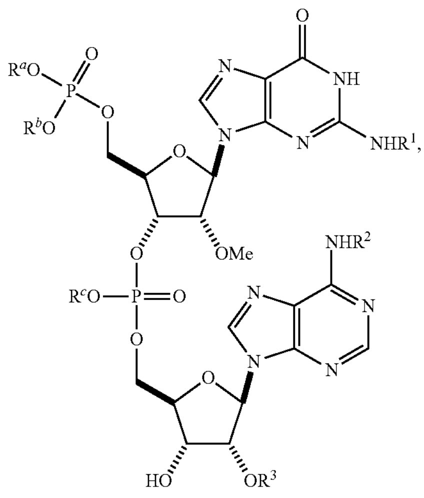

wherein $R^1$, $R^2$, $R^3$, $R^a$, $R^b$, and $R^c$ are as defined herein.

The compound of formula (6-b) may be reacted with a compound of formula (10) to obtain a compound of formula (11). The compound of formula (6-b) may be isolated prior to reaction with a compound of formula (10). The compound of formula (6-b) may also be purified prior to reaction with a compound of formula (10). Such a reaction process is referred to herein as a "stepwise" reaction process. Advantages of this process include, but are not limited to, high regio-selectivity in the coupling of compounds of formula (4) and (5), streamlined assembly of the downstream trinucleotides produced by the methods disclosed herein, and 5'-functionalization of the resulting trinucleotide at an earlier stage in the synthesis process. The yield of such a stepwise process (from the coupling of the compounds of formula (4) and (5) to the production of the compound of formula (11)) may be in the range of about 20% to about 50%, about 22% to about 48%, about 24% to about 46%, about 26% to about 44%, about 26% to about 44%, about 28% to about 42%, about 30% to about 40%, about 32% to about 38%, or about 34% to about 36%. In some embodiments, the yield of such a stepwise process in the method disclosed herein is about 30% to about 40%.

Completion of Trinucleotide Synthesis

After obtaining a compound of formula (11) using the steps described herein, the compound may be further reacted to synthesize a trinucleotide, a tetranucleotide, or a larger nucleic acid molecule. In some embodiments, the compound of formula (11) is deprotected to form a compound of formula (12), or a salt thereof:

(12)

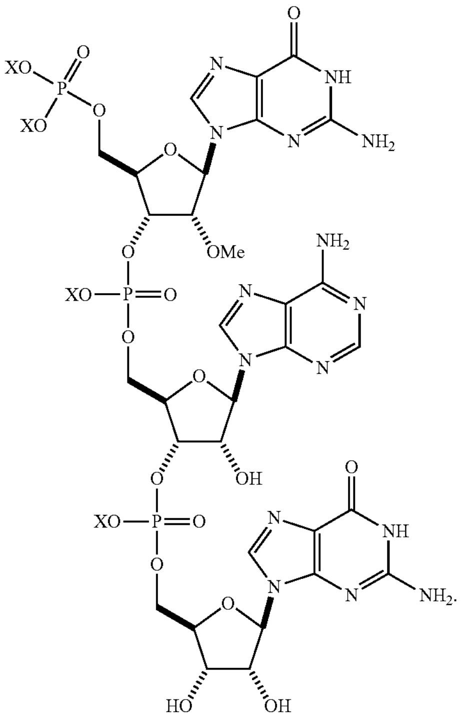

The compound of formula (12) may contain a moiety X, wherein X represents any suitable counterion of the phosphate moieties. In some embodiments, X is hydrogen, a Group 1 metal, a Group 2 metal, or a substituted or unsubstituted ammonium. In some embodiments, X is absent. In certain embodiments, X is hydrogen. In certain embodiments, X is an alkali metal or an alkaline earth metal. In certain embodiments, X is Li. In certain embodiments, X is Na. In certain embodiments, X is K. In certain embodiments, X is an ammonium ion. In certain embodiments, X is N,N-dimethyloctylammonium (DMOA).

Deprotecting the compound of formula (11) to obtain a compound of formula (12) may comprise deprotection of various moieties in the compound of formula (11) in any order, using any suitable methods known in the art. In some embodiments, deprotection of the phosphate moieties of the compound of formula (11) to obtain a compound of formula (12-a), or a salt thereof, is performed as the first deprotection step:

(12-a)

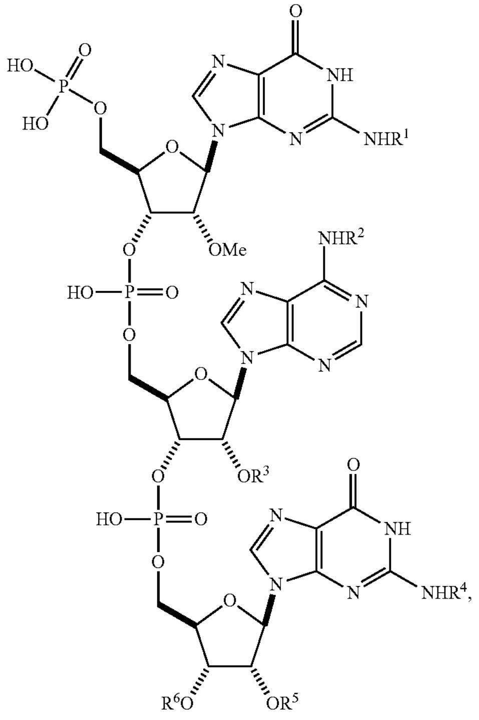

wherein $R^1$, $R^2$, $R^3$, $R^5$, and $R^6$ are as defined herein.

Following formation of the compound of formula (12-a), global deprotection of the compound of formula (12-a) may be performed to obtain the compound of formula (12), or a salt thereof. In some embodiments, deprotection of the phosphate moieties in the compound of formula (12) is carried out in the presence of N,O-Bis(trimethylsilyl)acetamide (BSA) and 1,8-diazabicyclo[5.4.0]undec-7-ene (DBU). In some embodiments, global deprotection of the compound of formula (12-a) is carried out in the presence of ammonium hydroxide and methylamine.

In some embodiments, deprotecting the compound of formula (11) comprises partially deprotecting the phosphate moieties of the compound of formula (11) to obtain a compound of formula (12-b):

(12-b)

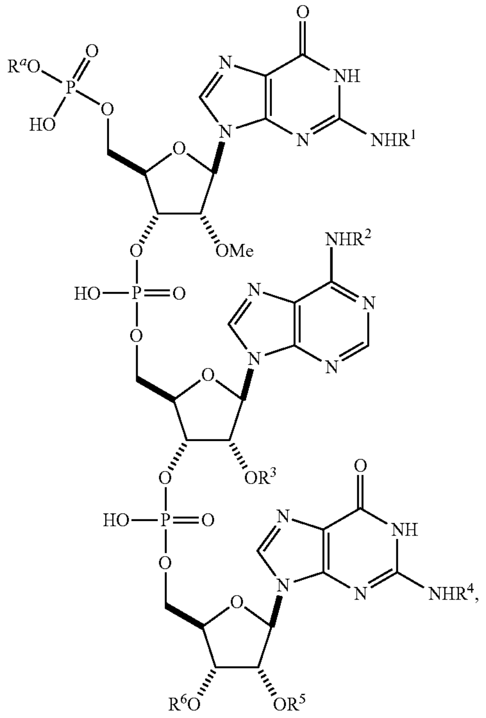

or a salt thereof, wherein $R^{aa}$, $R^1$, $R^2$, R, $R^4$, $R^5$, and $R^6$ are as defined herein; deprotecting the remaining phosphate moiety of the compound of formula (12-b) to obtain a compound of formula (12-a):

(12-a)

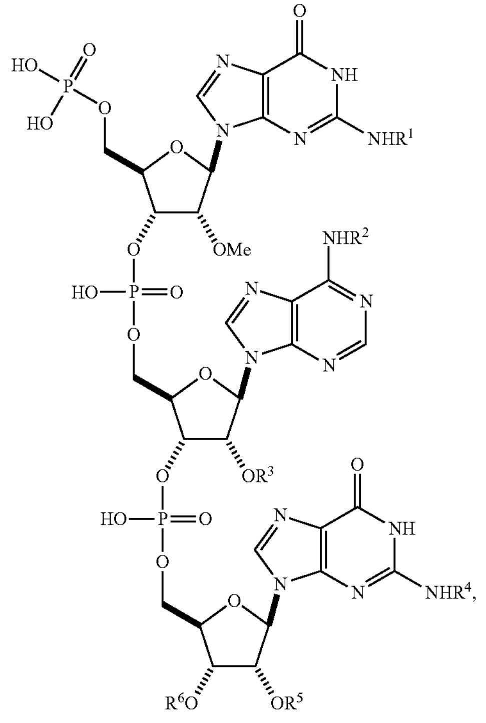

or a salt thereof, wherein $R^1$, $R^2$, $R^3$, $R^4$, $R^5$, and $R^6$ are as defined herein; and global deprotection of the compound of formula (12-a) to obtain the compound of formula (12), or a salt thereof. In some embodiments, deprotecting the phosphate moieties of the compound of formula (11) to obtain a compound of formula (12-b) is carried out in the presence of an amine. In some embodiments, the amine is a sterically hindered amine. In some embodiments, the amine is n-butylamine, sec-butylamine, isobutylamine, t-butylamine, isopropylamine, or diisopropylethylamine. In certain embodiments, the amine is t-$BuNH_2$. In some embodiments, deprotecting the remaining phosphate moiety of the compound of formula (12-b) to obtain a compound of formula (12-a) is carried out in the presence of N,O-Bis(trimethylsilyl)acetamide (BSA) and 1,8-diazabicyclo[5.4.0]undec-7-ene (DBU). In some embodiments, global deprotection of the compound of formula (12-a) to obtain the compound of formula (12) is carried out in the presence of ammonium hydroxide and methylamine. In some embodiments, the compound of formula (12-a) has the structure:

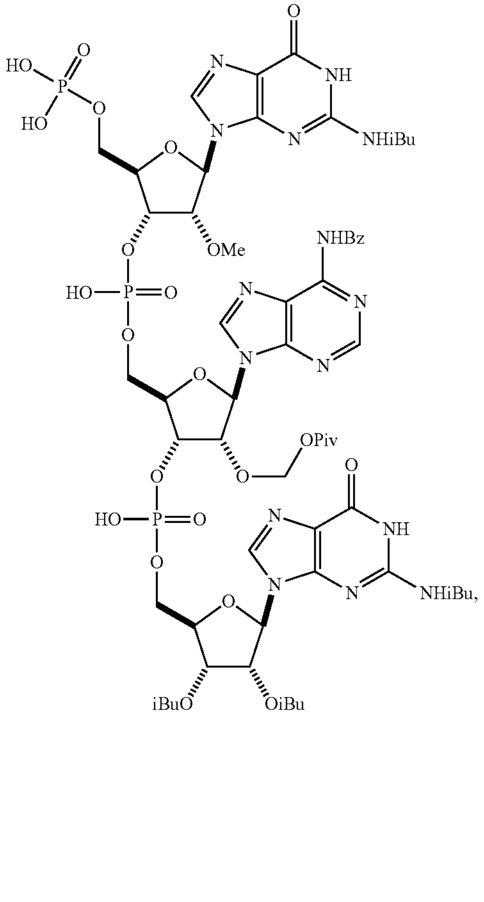

or a salt thereof.

In some embodiments, the compound of formula (12-b) has the structure:

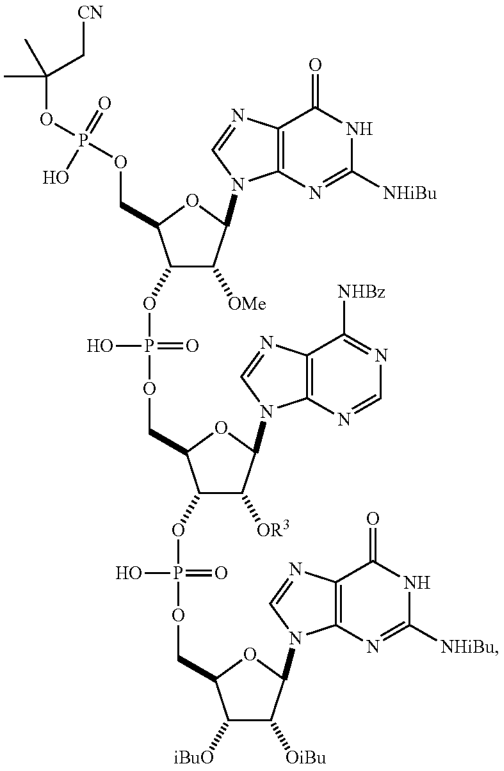

or a salt thereof.

In some embodiments, the methods disclosed herein further comprise reacting the compound of formula (12) with a compound of formula (15):

(15)

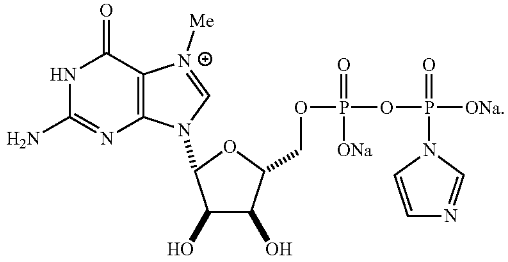

In certain embodiments, one or more of the sodium cations of the compound of formula (15) are absent or are independently replaced by another Group 1 metal cation or substituted or unsubstituted ammonium group. In certain embodiments, the compound of formula (15) further comprises an anion to achieve electronic neutrality. For example, one of the sodium cations in the compound of formula (15) may not be present, thereby resulting in electronic neutrality:

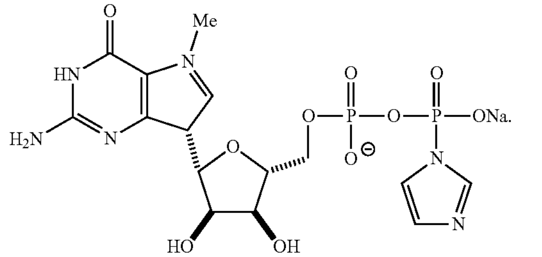

Reaction of the compounds of formula (12) and (15) may produce a compound of formula (16), or a salt thereof.

(16)

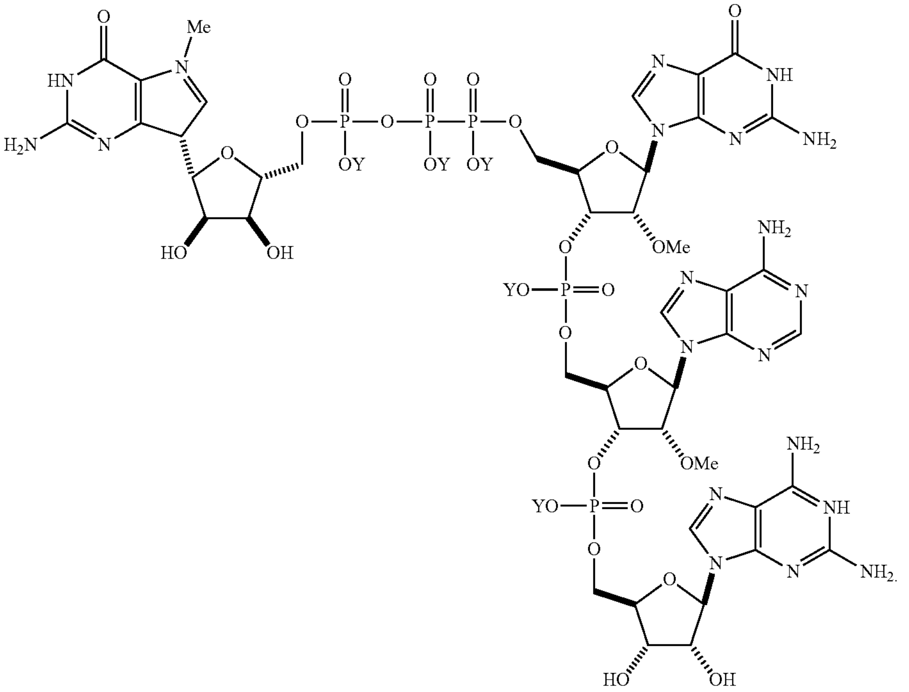

Compounds of formula (16) contain the moiety Y, representing independently defined counterions providing various salt forms of the compound. Any monovalent cation may be used independently at the positions of Y to create a salt of formula (16), including those described in the definitions section and throughout the present application. For example, suitable options for Y may include, but are not limited to, hydrogen, triethylammonium, ammonium, sodium, and potassium. In some embodiments, Y is ammonium (e.g., the compound of formula (16) is produced as an ammonium salt). In some embodiments, each instance of Y is the same. In certain embodiments, each instance of Y may be different. For example, one or more instances of Y may be ammonium, and each other instance of Y may independently be hydrogen or another suitable counterion. In certain embodiments, one or more Y is absent.

In some embodiments, prior to reacting the compound of formula (12) with the compound of formula (15), a compound of formula (12), wherein X is H, is converted to a compound of formula (12), wherein X is Na, K, or Li, and the compound of formula (12), wherein X is Na, K, or Li, is converted to a compound of formula (12), wherein X is DMOA. In certain embodiments, the compound of formula (12), wherein X is DMOA, is used in the reaction with the compound of formula (15) to obtain a compound of formula (16).

In some embodiments, reacting the compounds of formula (12) and formula (15) to produce the compound of formula (16) comprises metal salt-mediated coupling of the compound of formula (12) and the compound of formula (15) (e.g., as described in Woodman, E. K. et al. N,N'-Carbonyldiimidazole-Mediated Amide Coupling: Significant Rate Enhancement Achieved by Acid Catalysis with Imidazole-HCl. *Org. Process Res. Dev.* 2009, 13(1), 106-113). In some embodiments, the reaction of the compound of formula (12) and the compound of formula (15) is carried out in the presence of an acid and a metal or metal salt. In certain embodiments, the acid is HCl. Any suitable metal salt can be used in the reaction, including those disclosed in PCT Application Publication No. WO 2014/103704, which is incorporated herein by reference in its entirety. In some embodiments, the metal salt is $FeCl_3$, $AlCl_3$, $MnCl_2$, $MgCl_2$, $FeCl_2$, $ZnCl_2$, $NiCl_2$, $CoCl_2$, or $CaCl_2$. In certain embodiments, the metal salt is $FeCl_3$.

In some embodiments, the method further comprises purifying the tetranucleotide of formula (16) produced using the methods disclosed herein. Various methods for purifying oligonucleotides are known in the art (e.g., those disclosed in Zhang, et al. *Int. J. Mol. Sci.* Recent Methods for Purification and Structure Determination of Oligonucleotides. *Int. J. Mol. Sci.* 2016, 17(12), 2134) and can be utilized to purify the tetranucleotide of formula (16). In some embodiments, tangential flow filtration (TFF, also known as crossflow filtration) is used to purify the tetranucleotides produced by the methods disclosed herein. In TFF, the final reaction mixture containing the tetranucleotide to be purified is filtered by flowing it tangentially across the surface of a porous filter membrane. This process is continued, and over time the extra reagents pass through the filter membrane, leaving the tetranucleotide purified and concentrated. In some embodiments, the method comprises further purifying the tetranucleotide by anion-exchange chromatography (AEX), in which the tetranucleotide is passed through an ion-exchange resin containing positively charged chemical groups. Any substances in the mixture with a negative charge, such as the tetranucleotide compound of formula (16), bind to the ion-exchange resin, while other molecules pass through the resin. An AEX purification step can significantly increase the purity of the tetranucleotide compound. A person of ordinary skill in the art will readily appreciate that other methods may also be used for purification of the tetranucleotides synthesized herein.

Synthesis of Trinucleotide Building Blocks

The compounds utilized in the methods described herein may be produced by various synthetic procedures. For example, the compound of formula (4) may be formed by phosphitylation of a compound of formula (3):

(3)

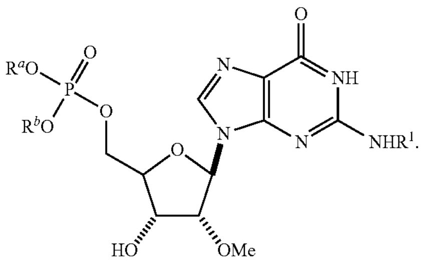

The compound of formula (3) may comprise the moieties $R^1$, $R^a$, and $R^b$. In some embodiments, $R^1$ is a nitrogen protecting group (e.g., an acyl nitrogen protecting group). In certain embodiments, $R^1$ is iso-butyl. $R^a$ and $R^b$ may each independently be an oxygen protecting group. In certain embodiments, $R^a$ is a 2-cyanoethyl group. In certain embodiments, $R^b$ is a 2-cyanoethyl group. In a compound of formula (3), therefore, $R^1$ may be iso-butyl, and $R^a$ and $R^b$ may each be 2-cyanoethyl groups. For example, the compound of formula (3) may have the structure:

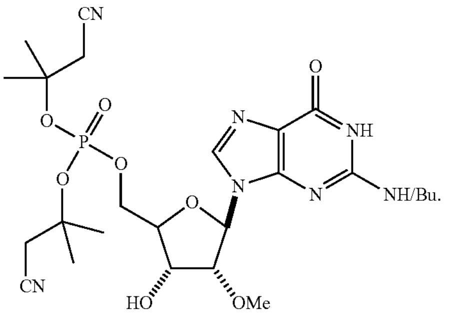

Phosphitylation of the compound of formula (3) to produce the compound of formula (4) may be carried out in the presence of, for example, 2-cyanoethyl N,N,N',N'-tetraisopropylphosphorodiamidite and 5-(Ethylthio)-1H-tetrazole (ETT). In some embodiments, the compound of formula (4) is not purified or worked up prior to reaction with the compound of formula (5).

In some embodiments, the method further comprises obtaining the compound of formula (3) by reacting a compound of formula (1) with a compound of formula (2):

(1)

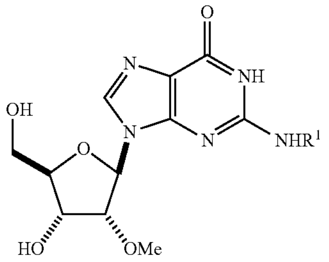

and (2)

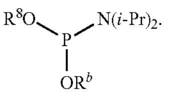

In some embodiments, the moiety $R^1$ in a compound of formula (1) is a nitrogen protecting group. For example, $R^1$ may be an acyl nitrogen protecting group. In certain embodiments, $R^1$ is iso-butyl. The moieties $R^a$ and $R^b$ in the compound of formula (2) may each independently be an oxygen protecting group. For example, $R^a$ and $R^b$ may each independently be a 2-cyanoethyl group. In some embodiments, the compound of formula (1) and the compound of formula (2) have the following structures:

(1)

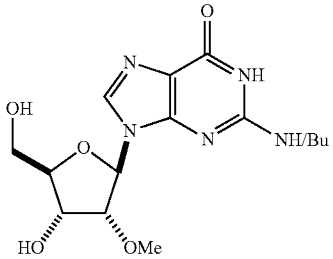

and (2)

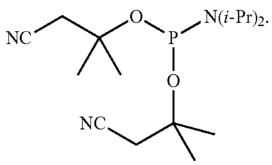

In some embodiments, reacting the compound of formula (1) and the compound of formula (2) is performed in the presence of an acid activator, such as pyridine trifluoroacetate. In some embodiments, the reaction further comprises oxidizing the product of such a reaction in the presence of an oxidant (e.g., any suitable oxidant as described herein).

In various embodiments, the compounds utilized in the methods described herein contain the moieties $R^a$, $R^b$, $R^c$, and $R^d$. Each of these moieties may independently be of the formula:

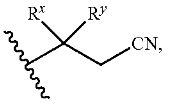

where each of $R^x$ and $R^y$ is independently H, optionally substituted cyclic or acyclic alkyl, optionally substituted cyclic or acyclic heteroalkyl, optionally substituted aryl, or optionally substituted heteroaryl. In some embodiments, $R^x$ and $R^y$ are combined to form a 3-6 membered ring (e.g., a carbocyclic or heterocyclic ring). In certain embodiments, Rx and R are independently H or $C_1$-$C_6$ alkyl. In certain embodiments, $R^x$ and $R^y$ are independently $C_1$-$C_6$ alkyl. $R^x$ and $R^y$ may also be combined to form a 3-6 membered carbocycle.

In certain embodiments, $R^x$ is methyl and $R^y$ is methyl. $R^a$ and $R^b$ may therefore each independently be of the formula:

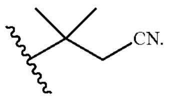 [SMILES: *C(C)(C)CC#N]

In some embodiments, $R^x$ and $R^y$ are both hydrogen. $R^c$ and $R^d$ may therefore each independently be of the formula:

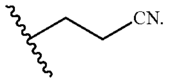

The methods disclosed herein may further comprise forming the compound of formula (5) by deprotection of the 3' and 5' hydroxyl groups of a compound of formula (5-a):

(5-a)

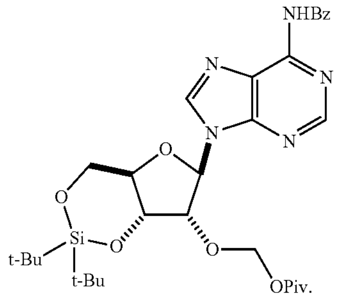

Such a deprotection may be carried out in the presence of an acid. In some embodiments, deprotection of a compound of formula (5-a) is carried out in the presence of hydrofluoric acid.

In some embodiments, the method further comprises forming the compound of formula (5-a) by protection of the 2' hydroxyl group of a compound of formula (5-b):

(5-b)

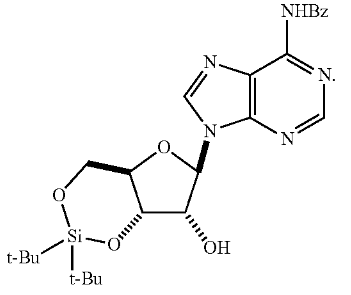

Protection of the compound of formula (5-b) may be carried in the presence of a base and a suitable oxygen protecting group precursor, for example, POMCl and KHDMS.

The methods described herein may further comprise formation of the compound of formula (5-b) by protection of the 3' and 5' hydroxyl groups in a compound of formula (5-c):

(5-c)

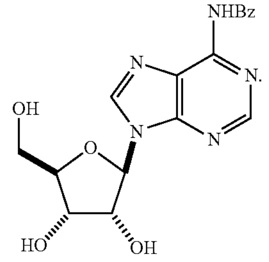

In some embodiments, protection of the 3' and 5' hydroxyl groups in a compound of formula (5-c) is carried out in the presence of t-$(Bu)_2Si(OTf)_2$.

The methods described herein may further comprise formation of the compound of formula (10) by phosphitylation of a compound of formula (9):

(9)

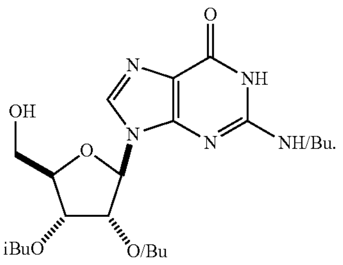

Phosphitylation of a compound of formula (9) may be carried out in the presence of 2-cyanoethyl N,N,N',N'-tetraisopropylphosphorodiamidite and diisopropylammonium tetrazolide.

In some embodiments, the method further comprises forming a compound of formula (9) by deprotecting the 5' hydroxyl group of a compound of formula (8):

(8)

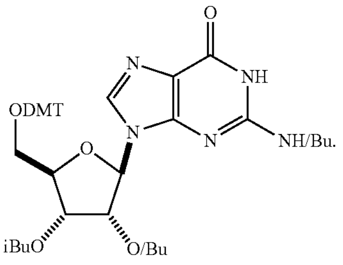

Deprotecting a compound of formula (8) may be carried out in the presence of TCA and $C_{12}H_{25}SH$.

The method may further comprise forming a compound of formula (8) by protection of the 2' and 3' hydroxyl groups of a compound of formula (7):

(7)

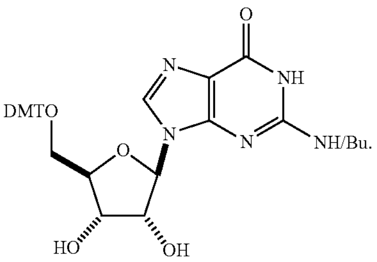

Such a reaction may be carried out in the presence of i-$Bu_2O$, triethylamine, and 4-dimethylaminopyridine.

In some embodiments, the method further comprises forming the compound of formula (15) by reaction of a compound of formula (14):

(14)

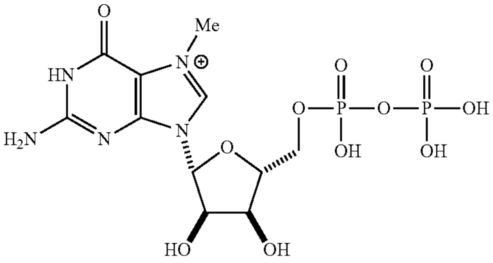

Reacting the compound of formula (14) may be carried out in the presence of imidazole, $Ph_3P$, TEA, and $(PyS)_2$.

In some embodiments, the method further comprises forming the compound of formula (14) by alkylating a compound of formula (13):

(13)

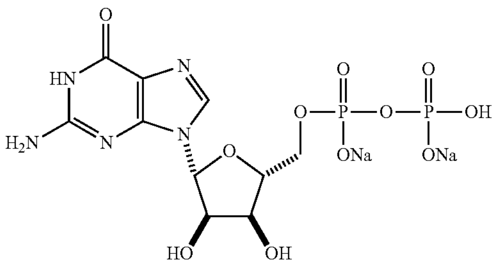

.

Alkylating the compound of formula (13) may be carried out in the presence of $(MeO)_2SO_2$. In some embodiments, the alkylation reaction further comprises reaction at a pH of approximately 3.5, approximately 3.6, approximately 3.7, approximately 3.8, approximately 3.9, approximately 4, approximately 4.1, approximately 4.2, approximately 4.3, approximately 4.4, or approximately 4.5. In certain embodiments, alkylating a compound of formula (13) is carried out at a pH of approximately 4. A compound of formula (13)

may be purified using various methods known in the art, including anion-exchange chromatography (AEX) as described herein.

In some aspects, the methods provided herein for synthesizing a trinucleotide comprise reacting a compound of formula (4) with a compound of formula (5):

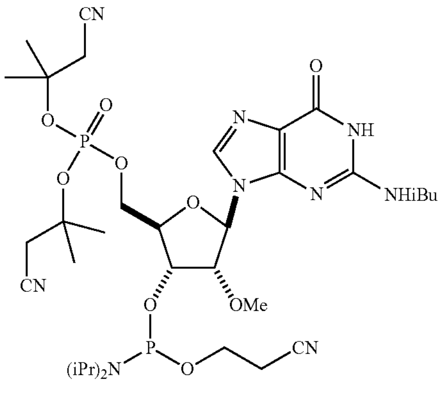

and

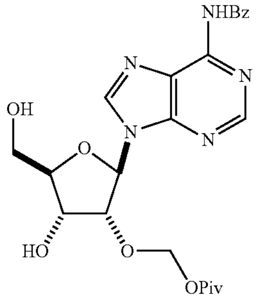

, in the presence of pyridine trifluoroacetate and pyridine to obtain a compound of formula (6):

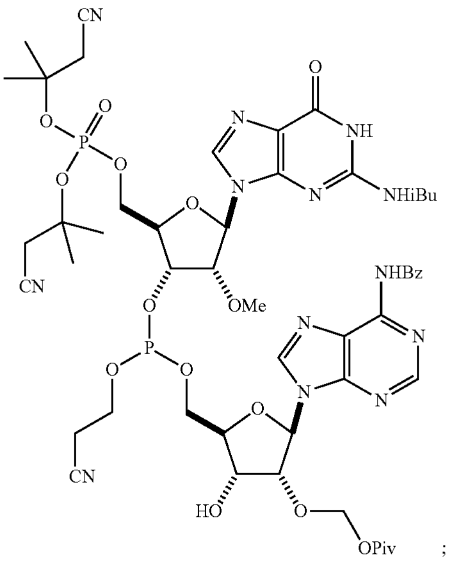

;

reacting the compound of formula (6) with a compound of formula (10):

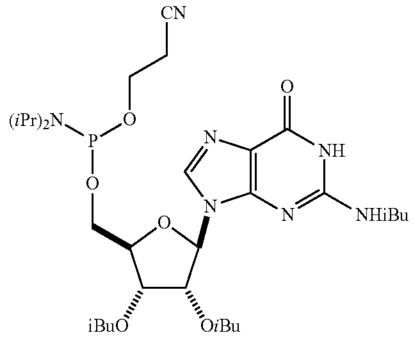

, in the presence of pyridine trifluoroacetate and pyridine; to obtain a compound of formula (11-a):

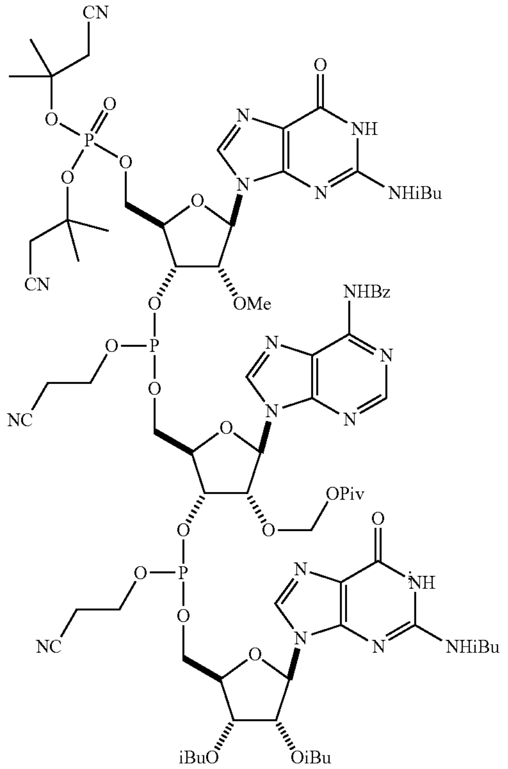

;

and reacting the compound of formula (11-a) with tert-butyl hydroperoxide to obtain a compound of formula (11):

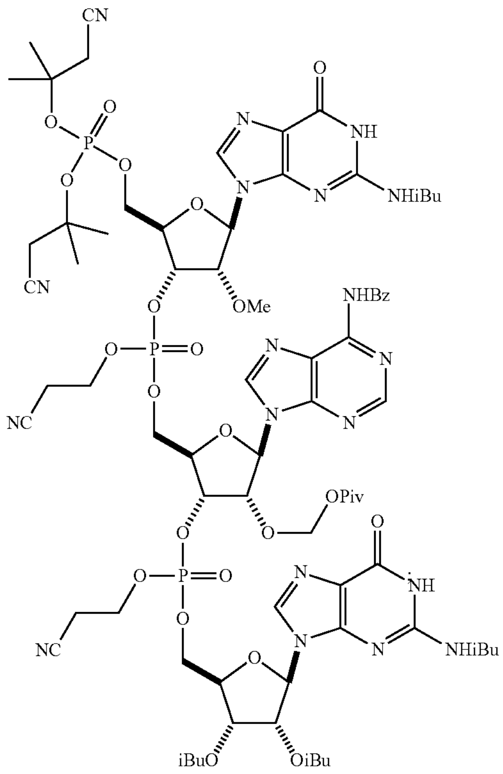

.

In some embodiments, the method further comprises partially deprotecting the phosphate moieties of the compound of formula (11) in the presence of t-$BuNH_2$ to obtain a compound of formula (12-b):

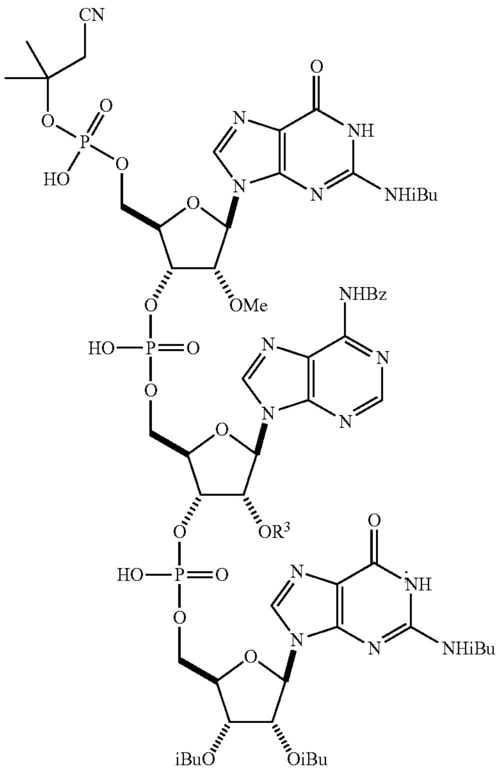
.

deprotecting the remaining phosphate moiety of the compound of formula (12-b) in the presence of N,O-Bis(trimethylsilyl)acetamide (BSA) and 1,8-diazabicyclo[5.4.0]undec-7-ene (DBU) to obtain a compound of formula (12-a):

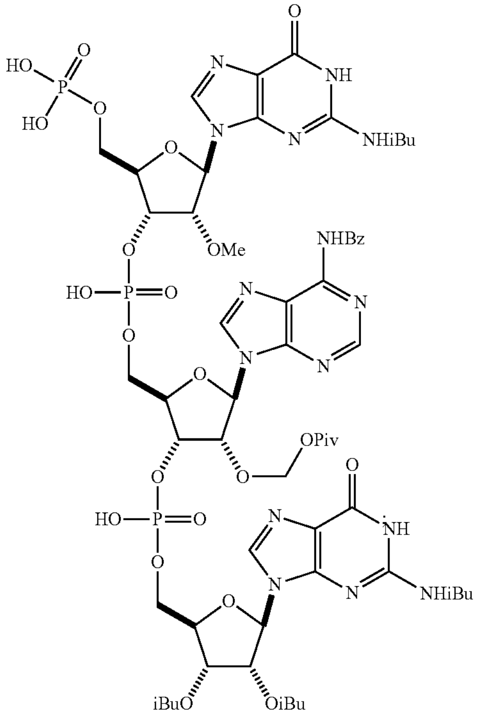
; and global deprotection of the compound of formula (12-a) in the presence of ammonium hydroxide and methylamine to obtain the compound of formula (12):

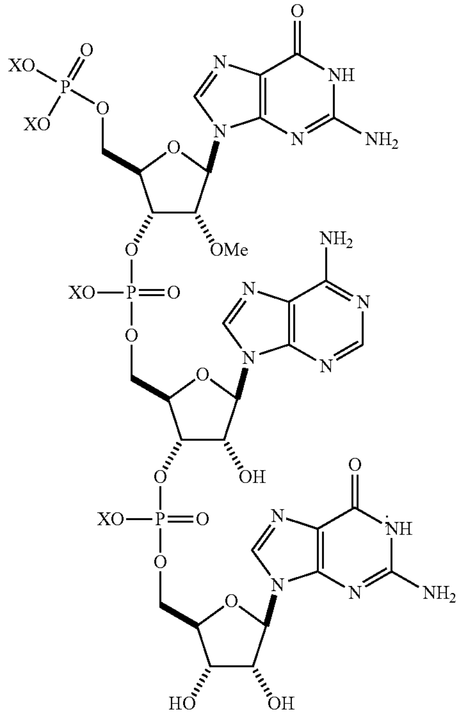
, wherein X is DMOA.

In some embodiments, the method further comprises reacting the compound of formula (12) with a compound of formula (15):

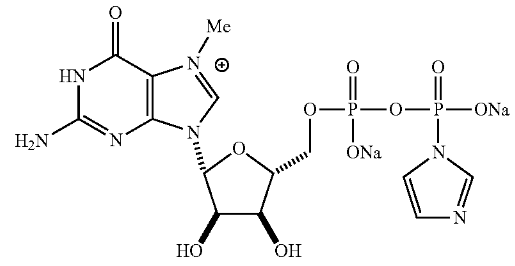

in the presence of HCl and a metal salt to obtain a compound of formula (16).

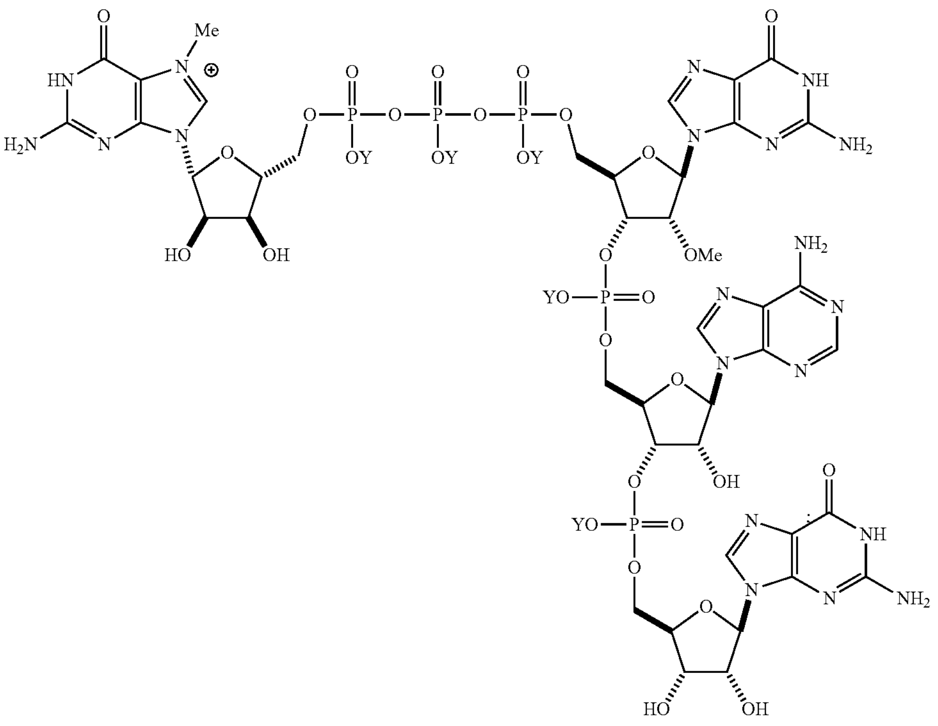
, wherein each instance of Y is independently $NH_4$ or absent.

In some embodiments, the compound of formula (4) is formed by phosphitylation of a compound of formula (3):

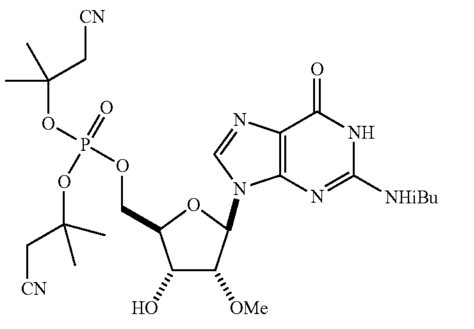

in the presence of 2-cyanoethyl N,N,N',N'-tetraisopropylphosphorodiamidite and 5-(Ethylthio)-1H-tetrazole (ETT) to obtain the compound of formula (4).

In some embodiments, the compound of formula (3) is formed by reacting a compound of formula (1) with a compound of formula (2) in the presence of pyridine trifluoroacetate and pyridine:

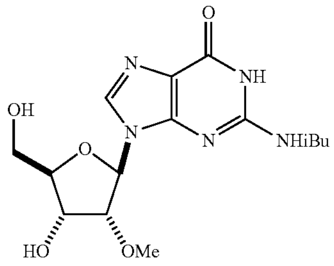

and

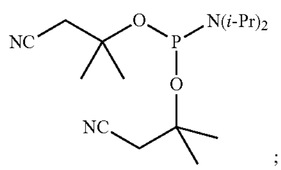
;

oxidizing the corresponding product in the presence of tert-butyl hydrogen peroxide to obtain the compound of formula (3).

Compositions of Matter

In one aspect, the present disclosure provides a compound of formula (1) having the structure:

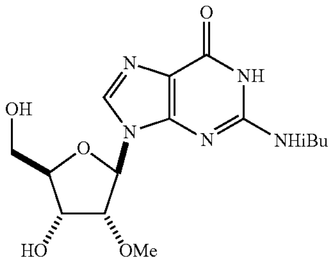

;

and salts thereof.

In another aspect, the present disclosure provides a compound of formula (2) having the structure:

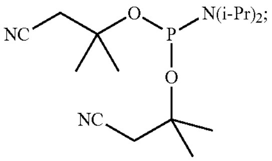

and salts thereof.

In another aspect, the present disclosure provides a compound of formula (3) having the structure:

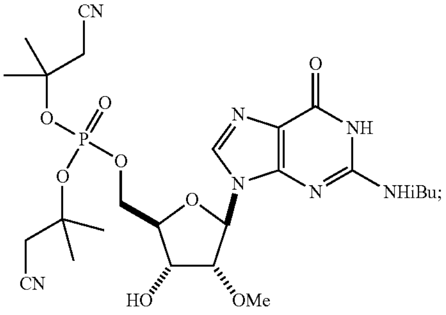

and salts thereof.

In another aspect, the present disclosure provides a compound of formula (4) having the structure:

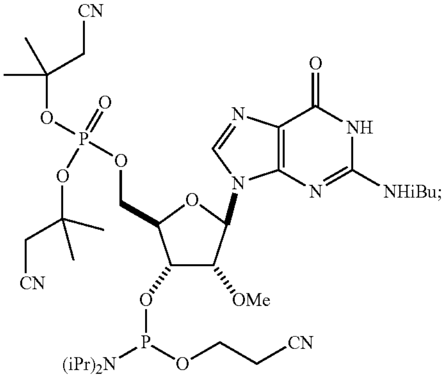

and salts thereof.

In another aspect, the present disclosure provides a compound of formula (5) having the structure:

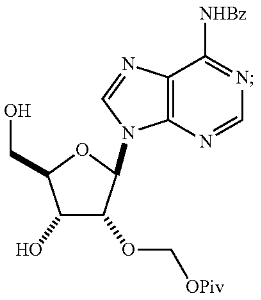

and salts thereof.

In another aspect, the present disclosure provides a compound of formula (6) having the structure:

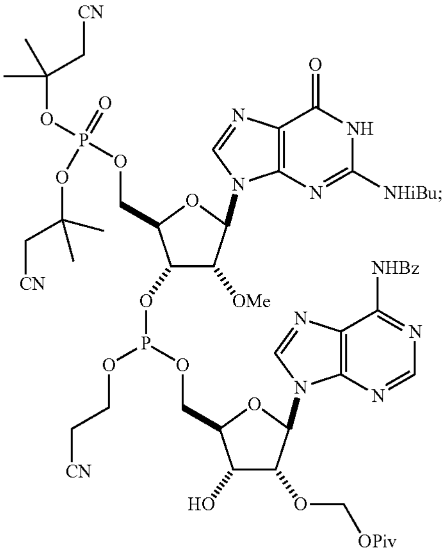

and salts thereof.

In another aspect, the present disclosure provides a compound of formula (7) having the structure:

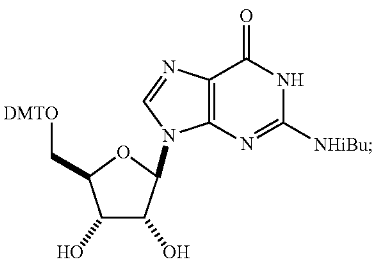

and salts thereof.

In another aspect, the present disclosure provides a compound of formula (8) having the structure:

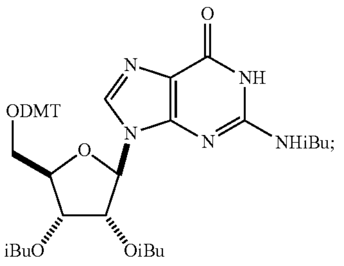

and salts thereof.

In another aspect, the present provides a compound of formula (9) having the structure:

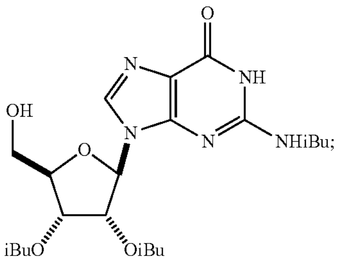

and salts thereof.

In another aspect, the present disclosure provides a compound of formula (10) having the structure:

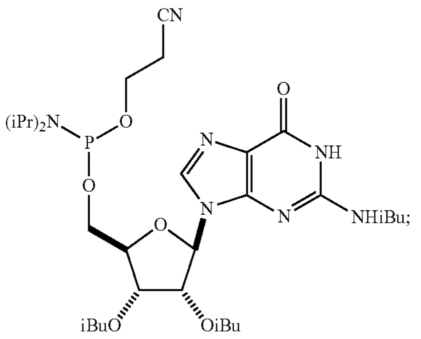

and salts thereof.

In another aspect, the present disclosure provides a compound of formula (11) having the structure:

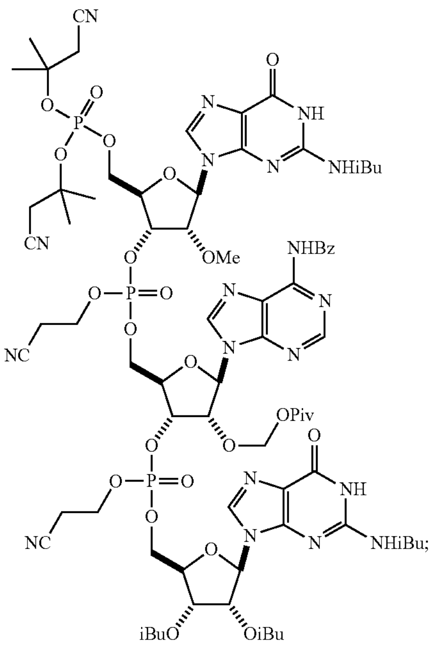

and salts thereof.

In another aspect, the present disclosure provides a compound of formula (11-a) having the structure:

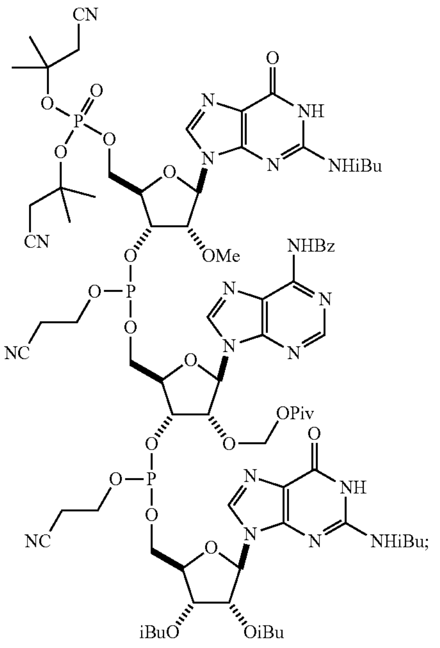

and salts thereof.

In another aspect, the present disclosure provides a compound of formula (12-a) having the structure:

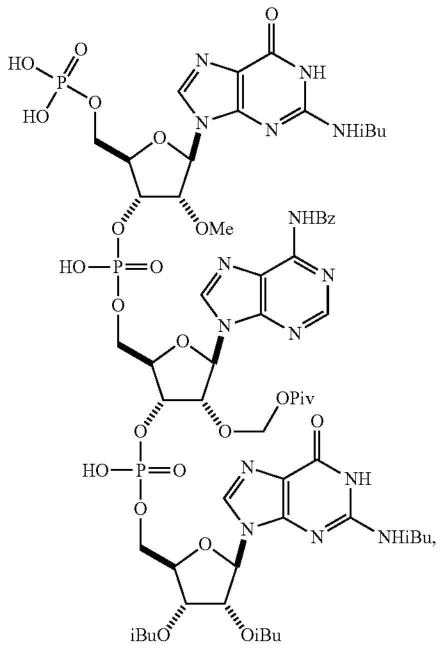

and salts thereof.

In another aspect, the present disclosure provides a compound of formula (12-b) having the structure:

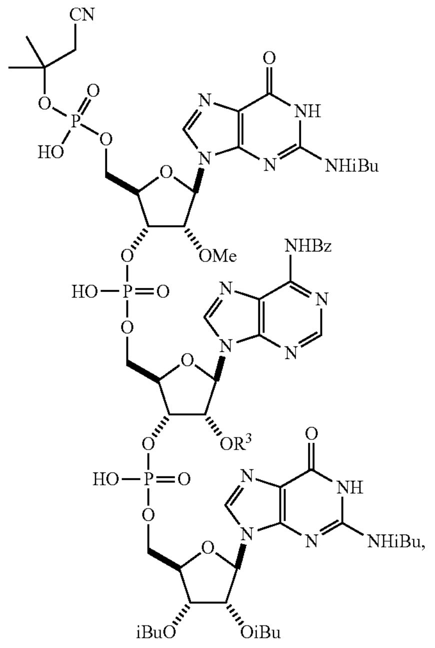

and salts thereof.

In another aspect, the present disclosure provides a compound of formula (12) having the structure:

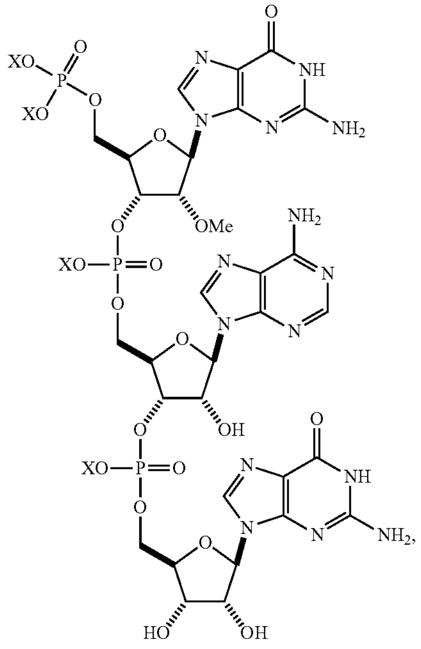

wherein X is absent, H, Na, or DMOA; and salts thereof.

In another aspect, the present disclosure provides a compound of formula (15) having the structure:

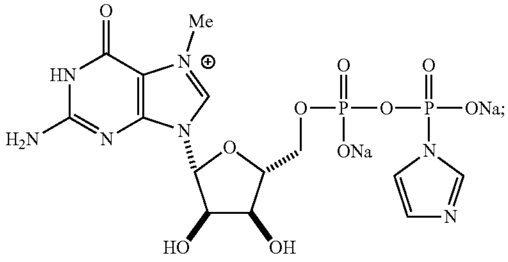

and salts thereof.

In another aspect, the present disclosure provides a compound of formula (16) having the structure:
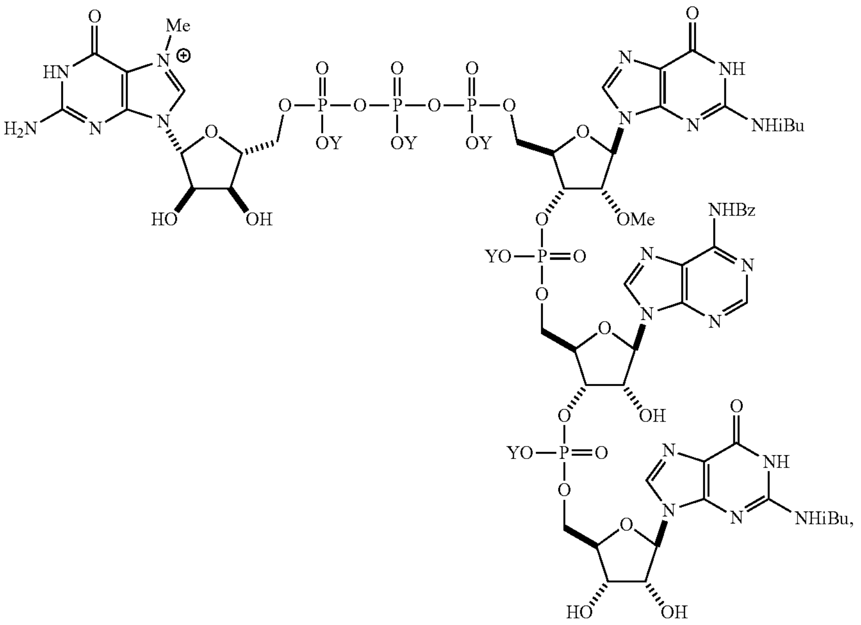
wherein each instance of Y is independently $NH_4$ or absent, and salts thereof.
EXAMPLES
Example 1: Stepwise Trinucleotide Assembly
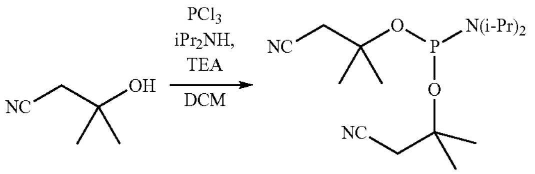
2s
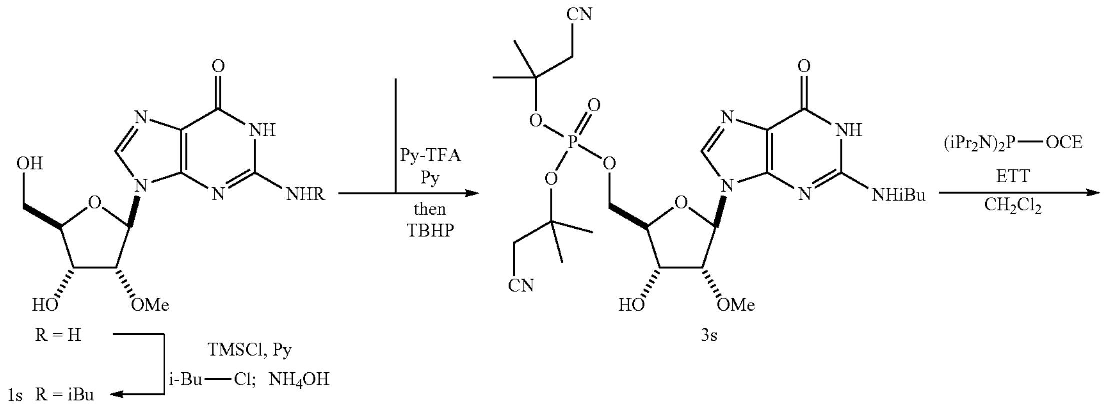
R = H
1s R = iBu
3s -continued
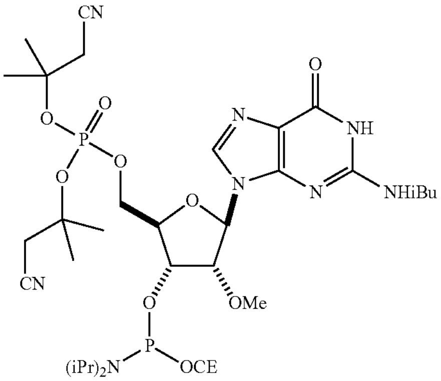
4s
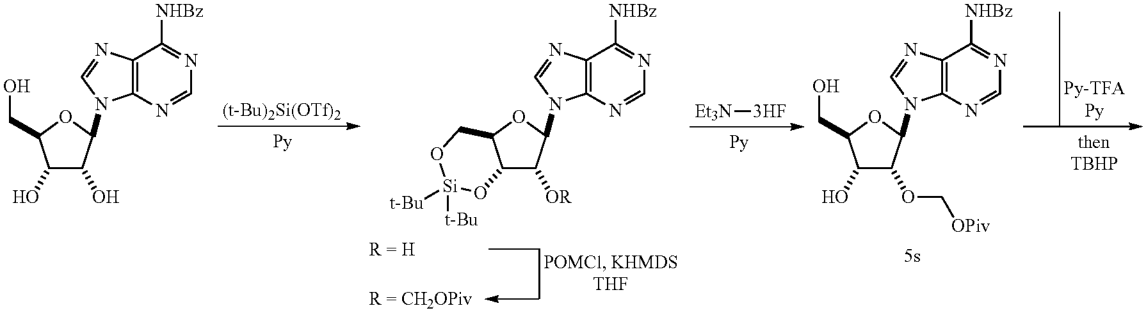
R = H
R = $CH_2OPiv$
5s
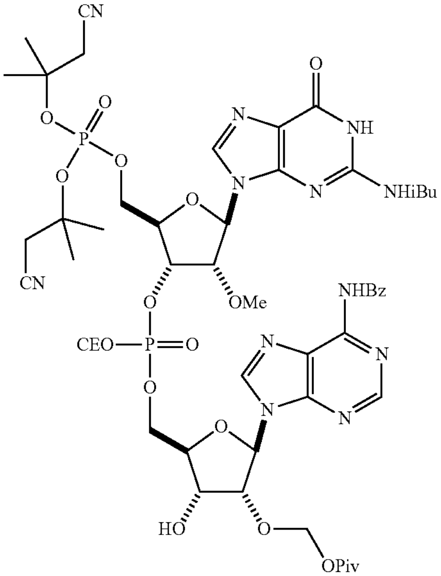
6s
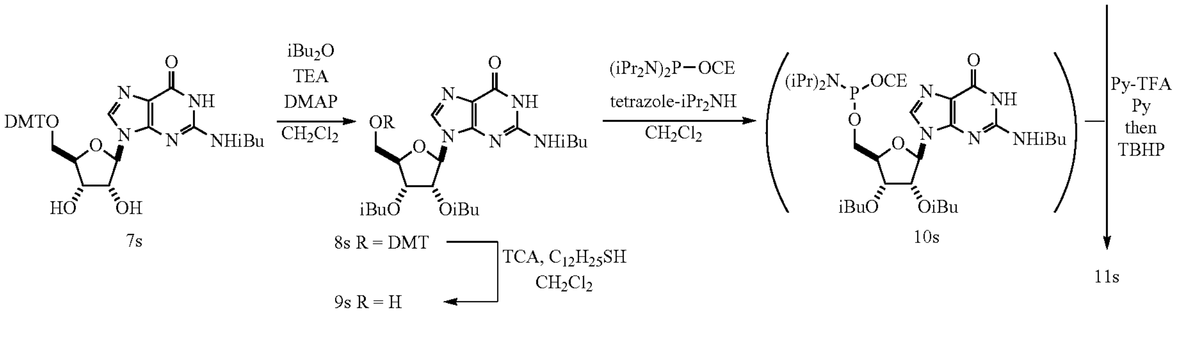
7s
8s R = DMT
9s R = H
10s
11s -continued
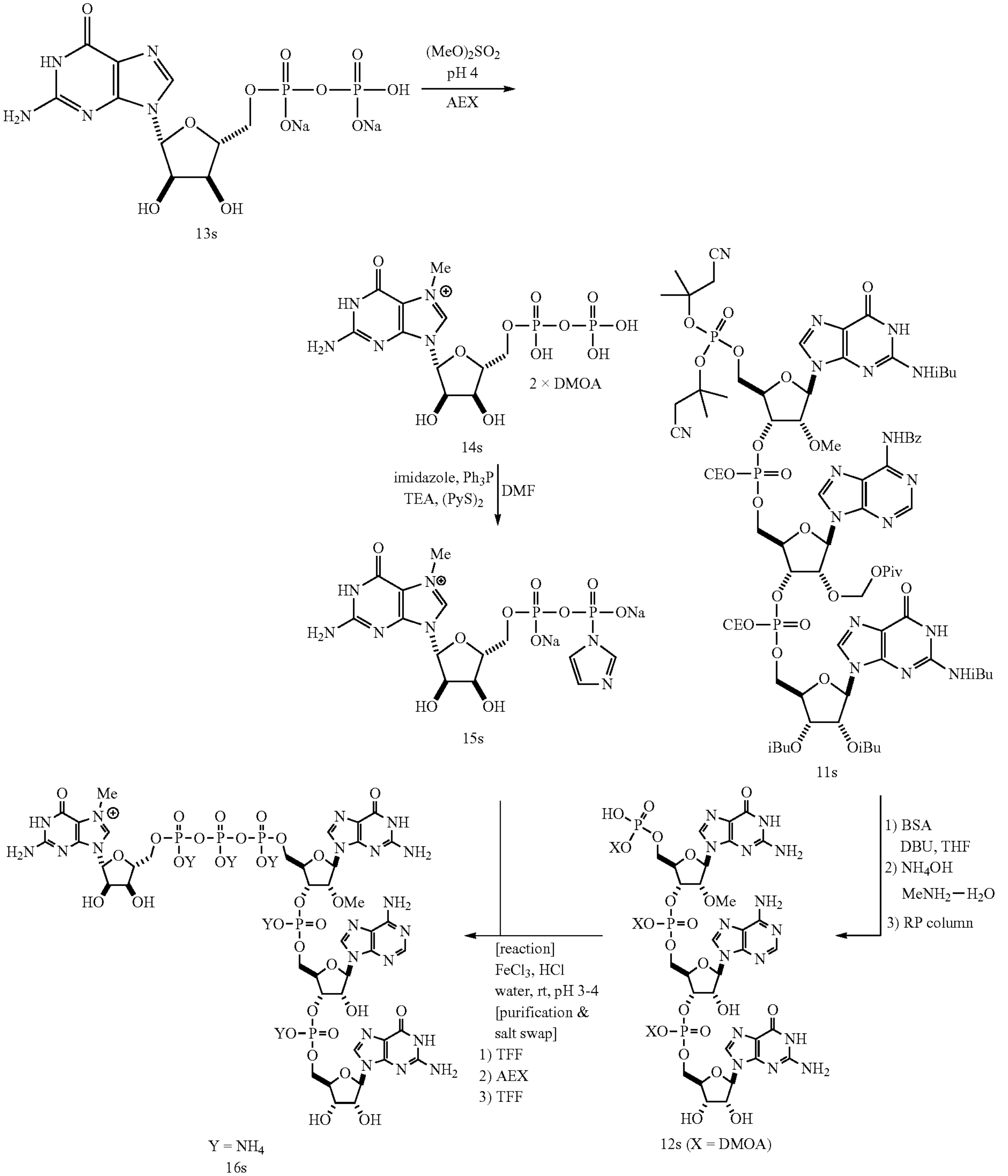
13s, 14s, 15s, 11s
Y = $NH_4$
16s
12s (X = DMOA)
Sterically-Hindered Phosphoramidite 2 s:
-continued
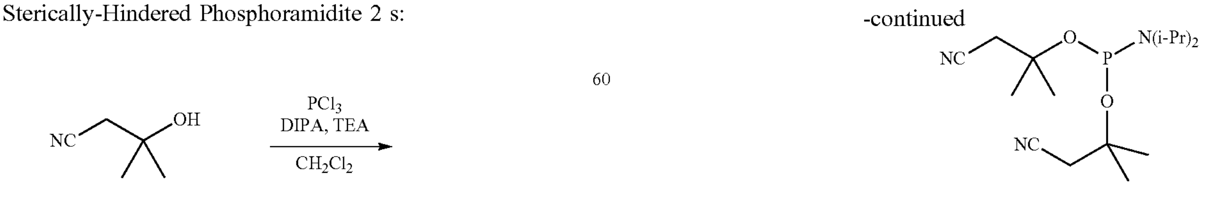
3-hydroxy-3-methylbutanenitrile
2s $PCl_3$ (20.5 g, 13 ml, 149 mmol, 1 equiv., 1 wt, 1 vol) was dissolved in $CH_2Cl_2$ (200 ml, 9.8 vols) and cooled to <−20° C. Triethylamine (TEA; 15.3 g, 21 ml, 151 mmol, 1 equiv.) was added followed by dropwise addition of diisopropylamine (DPA; 15.2 g, 21 ml, 150 mmol, 1 equiv.) over 10 minutes maintaining <−20° C. Upon complete addition, the mixture was stirred at −23 to −20° C. for 1 hour, then allowed to warm up to ambient temperature. After 6 hours, the mixture was cooled to −10° C. and TEA (30.5 g, 42 ml, 301 mmol, 2 equiv.) was added. 3-hydroxy-3-methylbutanenitrile (29.7 g, 31 ml, 300 mmol, 2 equiv.) was added and the mixture was allowed to warm up to ambient temperature. After overnight stirring, the mixture was diluted with hexanes (200 ml, 19.8 vols), filtered, and rinsed with $CH_2Cl_2$/hexanes 1:1 (100 ml, 5 vols). The filtrate was concentrated, re-diluted with hexanes/EtOAc 1:1 (200 ml, 9.8 vols) and filtered. The filtrate was concentrated and passed through a silica gel plug (75 g) with hexanes/EtOAc 20% with 0.1% TEA (1 L, 50 vols; for conditioning, sample loading, and elution). The filtrate was concentrated to give light yellow solid, which was triturated, filtered and rinsed with n-heptane (200 ml, 9.8 vols) and dried overnight to give 2 s (41.2 g, 125 mmol, 84% yield) as white crystalline solid. The recovered filtrate/rinse was concentrated, diluted with n-heptane (20 ml, 1 vol) and stored in the freezer. Yellow supernatant was removed by decantation to give additional 2 s (2.3 g, 7.0 mmol, 4.7% yield) as light yellow solid.

2'-OMe-G 5'-Phosphate 3 s:

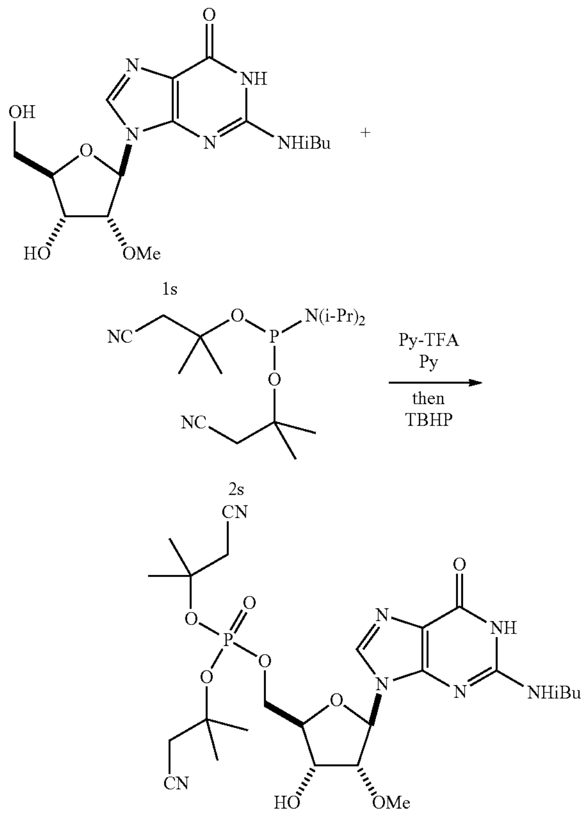

1s

2s

3s 1 s (15 g, 40.83 mmol, 1 equiv., 1 wt, 1 vol) was azeotroped with pyridine (75 ml×2, 5 vols×2), re-dissolved in pyridine (30 ml, 2 vols) and cooled to −10° C. Pyridine trifluoroacetate (Py-TFA; 15.78 g, 81.7 mmol, 2 equiv) was azeotroped with pyridine (75 ml×2, 5 vols×2) and re-dissolved in pyridine (50 ml, 3.3 vols) and consolidated into is (25 ml pyridine, 1.7 vols was used for complete rinse and transfer). 2 s (13.37 g, 40.83 mmol, 1 eq, 0.89 wt) was added as solid (−8° C.) and the mixture was warmed up to 0° C. After stirring at 0° C. for 40 min, the mixture was let warm up to ambient temperature over 1 hour, stirred for an additional 1 hour, and cooled down to 0° C. TBHP (5-6 M solution in decane; 8.9 ml, 0.59 vols, 49 mmol, 1.2 equiv.) was added and the mixture was allowed to warm up to ambient temperature. After overnight stirring, the reaction was quenched with 20 wt % aqueous sodium sulfite ($Na_2SO_3$; 12.9 g, 0.86 g, 20.4 mmol, 0.5 equiv), stirred for 10 minutes and concentrated. The resultant mixture was partitioned between $CH_2Cl_2$ (150 ml, 10 vols) and 9 wt % aqueous $NaHCO_3$ (153 g, 10 wts, 164 mmol, 4 equiv.). The organic layer was separated and set aside. The aqueous layer was extracted with $CH_2Cl_2$ (150 ml, 10 vols). All of the organic layers were combined, washed with brine (45 ml, 3 vols), dried over sodium sulfate ($Na_2SO_4$; 10 g, 0.67 wt, 70 mmol), and filtered. The filtrate was concentrated, azeotroped with toluene (75 ml, 5 vols), and subjected to silica gel column chromatography (EtOAc/IPA 10%-25% & EtOAc/acetone 30-100%) to give 3 s (18.08 g, 1.21 wt, 29.7 mmol, 72% yield) as white dry foam.

$^1$H-NMR ($CDCl_3$, 300 MHz), δ (ppm)=12.31 (s, 1H), 10.64 (s, 1H), 7.83 (s, 1H), 5.90 (d, J=5.9 Hz, 1H), 4.64 (m, 1H), 4.54 (t, J=5.5 Hz, 1H), 4.42 (m, 2H), 4.34 (m, 1H), 3.84 (d, J=4.1 Hz, 1H), 3.39 (s, 3H), 2.90 (d, J=2.8 Hz, 2H), 2.85 (m, 1H), 2.78 (d, J=4.2 Hz, 2H), 1.71 (s, 3H), 1.70 (s, 3H), 1.61 (s, 3H), 1.59 (s, 3H), 1.25 (m, 6H).

2'-OMe-G 3'-Phosphitylation:

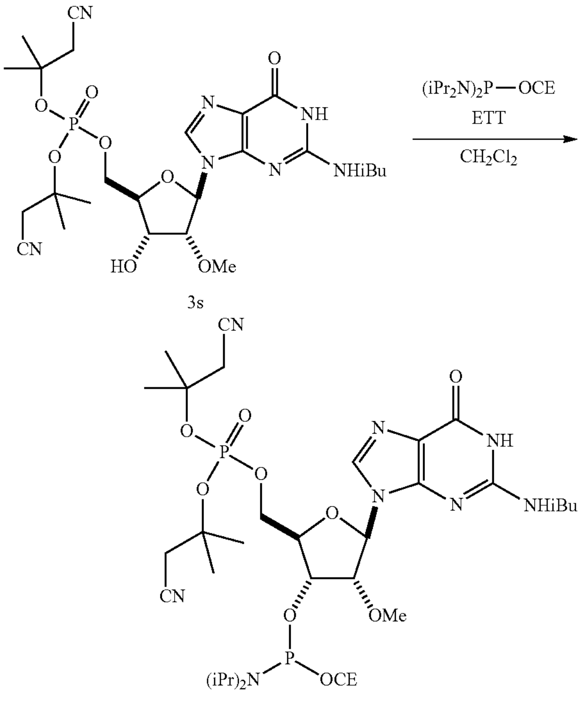

3s

4s 3 s (400 g, 656 mmol, 1 equiv., 1 wt, 1 vol) was azeotroped with acetonitrile (1.2 L×2, 3 vols×2) and transferred to a 5 L 3-neck reactor with overhead mechanical stirrer by dilution and rinse with $CH_2Cl_2$ (1.2 L, 3 vols). 2-Cyanoethyl N,N,N',N'-tetraisopropylphosphorodiamidite (218.3 g, 724 mmol, 1.10 eq) was azeotroped with acetonitrile (1.2 L, 3 vols) and added to the reactor by dilution and rinse with $CH_2Cl_2$ (1.2 L, 3 vols). The resultant mixture was cooled down to −3° C. and 5-(Ethylthio)-1H-tetrazole (ETT, 93.96 g, 722 mmol, 1.1 eq). was added. The reaction was let warm up to ambient temperature, continued overnight, and then diluted with n-heptane (1.2 L, 3 vols). The mixture was filtered to remove precipitates, and the reactor and filter cake were rinsed with 2:1 v/v $CH_2Cl_2$-heptane (0.6 L, 1.5 vol). The recovered filtrate was sequentially washed with: (1) 20 wt % aqueous $KHCO_3$ (500 g, 1.0 mol, 1.5 eq), (2) 15 wt % aqueous NaCl (800 g) (3) 23 wt % aqueous NaCl (800 g). The organic layer was concentrated, azeotroped with acetonitrile (1.2 L×2, 3 vols×2), re-dissolved in acetonitrile (800 ml, 2 vols), and rinsed/diluted with acetonitrile (200 ml, 0.5 vols) to give 4 s stock solution (1461 g, net 656.2 mmol assumed, 0.449 mmol/g) for storage at 5° C.

$^1H$-NMR ($CD_3CN$, 300 MHz), δ (ppm)=12.07 (br, 1H), 10.45 (br, 1H), 7.85 (ds, 1H), 5.87 (m, 1H), 4.67 (m, 1H), 4.60 (m, 1H), 4.4-4.5 (m, 3H), 3.91-4.11 (m, 2H), 3.65-3.81 (m, 3H), 3.52 (m, 1H), 3.37 & 3.33 (ds, 3H), 2.94 (m, 2H), 2.81 (m, 2H), 2.71-2.78 (m, 3H), 1.67 (s, 3H), 1.66 (s, 3H), 1.57 (s, 3H), 1.55 (s, 3H), 1.2-1.3 (m, 18H).

2'-OMe-G+A Coupling:

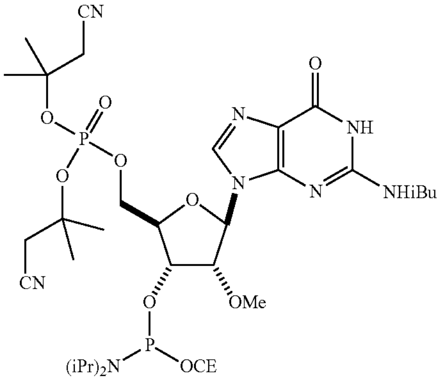

4s

+

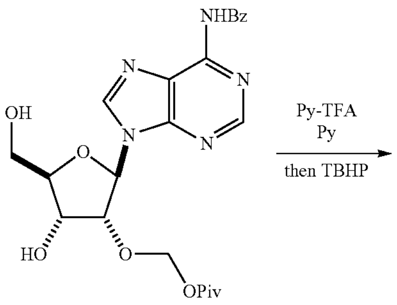

5s

-continued

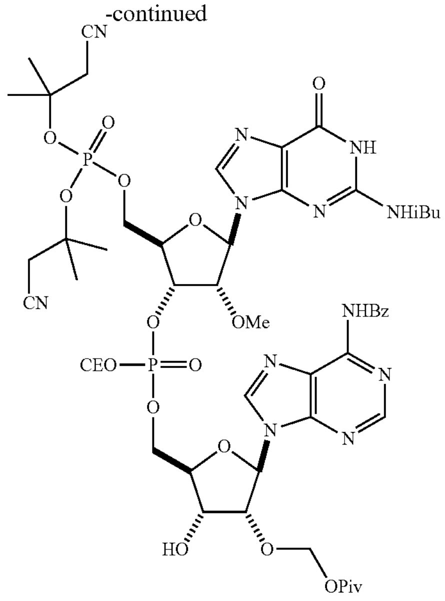

6s 5 s (170.65 g, 351.5 mmol, 1 eq, 1 wt, 1 vol) was azeotroped with pyridine (850 ml, 5 vols) to remove 550 ml pyridine. Azeotrope was repeated with pyridine (850 ml, 5 vols) to remove 750 ml pyridine (approx. 400 ml pyridine remained). In a separate flask, pyridine trifluoroacetate ("Py-TFA", 135.8 g, 703 mmol, 2.0 equiv.) was azeotroped with pyridine (850 ml, 5 vols) to remove 550 ml pyridine. Azeotrope was repeated with pyridine (850 ml, 5 vols) to remove 830 ml pyridine (approximately 320 ml pyridine remained). The resultant mixture was diluted with pyridine (360 ml) to adjust the total pyridine volume to approximately 680 ml (4 vols). 4 s stock solution (1056 g, net 492 mmol assumed, 0.466 mmol/g, 1.4 eq) was concentrated, azeotroped with 850 ml pyridine to remove 680 ml pyridine (approx. 170 ml pyridine remained). 4 s was transferred into a 12 L reactor by dilution and rinse with 322 ml pyridine. 5 s was transferred to the reactor by dilution and rinse with 300 ml pyridine. The resultant mixture was cooled to below −10° C. and Py-TFA solution was added. The mixture was slowly warmed up to 5° C. over 3 h and cooled down to 2° C. TBHP (5-6 M in decane, 96 ml, 0.5 mmol, 1.5 eq) was added and the mixture was let warm up to ambient temperature (19° C.). After 2 hours, the mixture was diluted with toluene (3.75 L, 22 vols), cooled down to 10° C., and quenched with 10 wt/o aqueous sodium sulfite ($Na_2SO_3$, 332 g, 263 mmol, 0.75 eq). The top layer was separated and set aside. The bottom layer was diluted with water (0.85 L, 5 vols) and extracted with $CH_2Cl_2$ (1.7 L, 10 vols). All the organic layers were combined and concentrated. The resultant mixture was diluted with $CH_2Cl_2$ (3.4 L, 20 vols) and sequentially washed with: (1) 10 wt/o aqueous $KHCO_3$ (704 g, 703 mmol, 2.0 eq), (2) 10 wt % aqueous NaCl (500 g), (3) 23 wt % aqueous NaCl (500 g), and concentrated. The crude mixture thus obtained was azeotroped with toluene (1.37 L, 8 vols) and subjected to silica gel plug purification ($SiO_2$, 2 kg plug×2, elution with $CH_2Cl_2$-EtOH 2.5% to 20%; RediSep Gold 330 g×1, elution with $CH_2Cl_2$-EtOH 2% to 14%). Main fractions were concentrated, consolidated with acetone, concentrated again, and azeotroped with n-heptane to give 6 s as white solid (295.5 g, 244 mmol, 69% yield).

G-Phoshitylation:

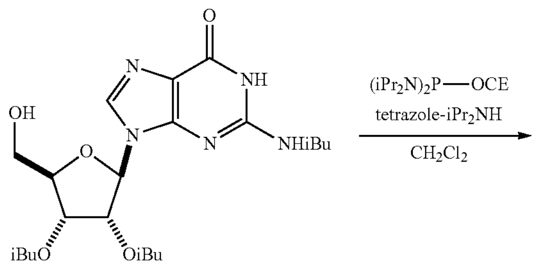

9s

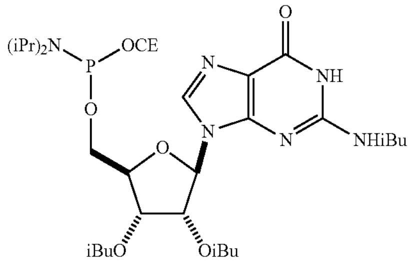

10s 9 s (56.6 g, 115 mmol, 1 equiv., 1 wt, 1 vol) was azeotroped with acetonitrile (283 ml×2, 5 vols×2) and suspended in $CH_2Cl_2$ (142 ml, 2.5 vols). 2-Cyanoethyl N,N,N',N'-tetraisopropylphosphorodiamidite (38.09 g, 126 mmol, 1.1 equiv.) was azeotroped with acetonitrile (283 ml, 5 vols) and consolidated into 9 s with $CH_2Cl_2$ (142 ml, 2.5 vols). The resultant mixture was cooled to −10° C. and diisopropylammonium tetrazolide (1.97 g, 11.5 mmol, 0.1 equiv.) was added. The reaction was allowed to warm up to ambient temperature and stirred overnight to give 10 s solution (theoretical 100% yield assumed, 11.5 mmol, 1 equiv.), which was used directly for 2'-OMe-G/A+G coupling.

2'-Ome-G/A+G Coupling:

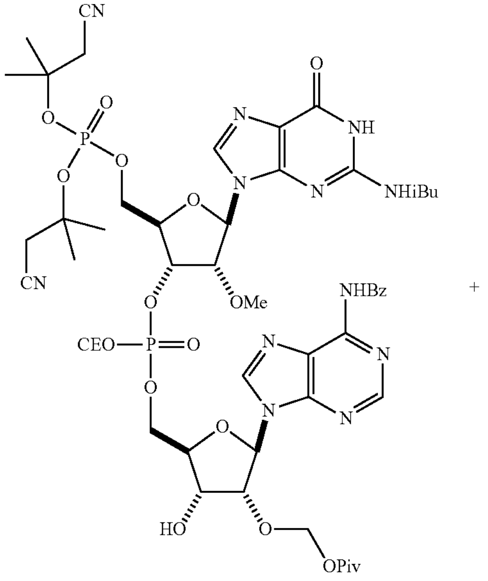

6s

-continued

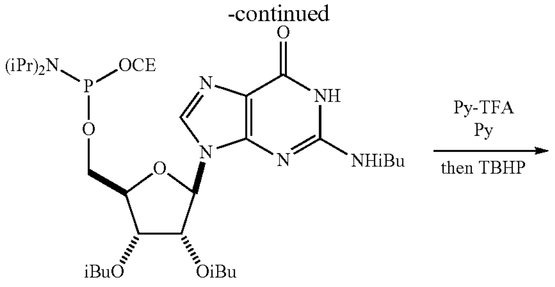

10s

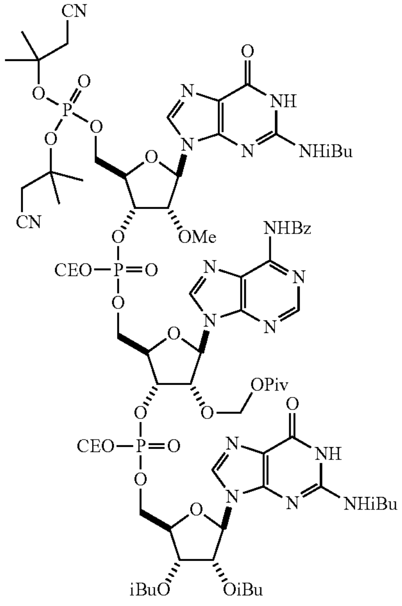

11s 6 s (92.6 g, 76.5 mmol, 1 equiv., 1 V, 1 wt) was azeotroped with pyridine (460 ml and 287 ml, 5 V and 3 vols), and then diluted with pyridine (185 ml, 2 vols) and cooled to −10° C. Pyridine trifluoroacetate (Py-TFA, 29.56 g, 153 mmol, 2 eq) was azeotroped with pyridine (185 ml×2, 2 vols×2) and diluted with pyridine (140 ml, 1.5 vols). 10 s solution (reaction mixture in 0.28 L $CH_2Cl^2$, net 115 mmol assumed, 1.5 eq) was added to 6 s solution and rinsed with $CH_2Cl_2$ (17 ml). After 5 minutes, Py-TFA solution was added at −10° C. and the mixture was allowed to warm up to ambient temperature. After overnight stirring, the mixture was cooled down to 0° C. and TBHP (5-6 M solution in decane, 20.9 ml, 0.11 mol, 1.5 eq) was added. The mixture was allowed to warm up to ambient temperature and stirred for 4-5 hours. The reaction mixture was diluted with toluene (930 ml, 10 vols), cooled to 0° C., and quenched with 10 wt % aqueous sodium sulfite ($Na_2SO_3$, 60 g, 48 mmol, 0.62 equiv.). The upper layer was separated and set aside. The bottom layer was extracted with: (1) toluene (185 ml, 2 vols) and (2) $CH_2Cl_2$ (280 ml, 3 vols). All the organic layers were combined and concentrated to give orange oil, which was diluted with $CH_2Cl_2$ (930 ml, 10 vols) and washed with 10 wt % aqueous KHCO; (150 g, 150 mmol, 2 eq). The organic layer was separated and set aside. The aqueous layer was extracted with $CH_2Cl_2$ (185 ml, 2 vols). All the organic layers were combined, washed with 12 wt % aqueous NaCl (125 ml×2), dried over sodium sulfate ($Na_2SO_4$, 93 g, 1 wt) overnight, filtered and partially concentrated to approximately 0.8 L, and subjected to silica gel plug filtration ($SiO_2$ 1 kg, elution with $CH_2Cl_2$/EtOH 2% to 40%) to give 1 is as a mixture of products with and without partial loss of 2-cyanoethyl (CE) group (yellow foam, 113 g).

Global Deprotection:

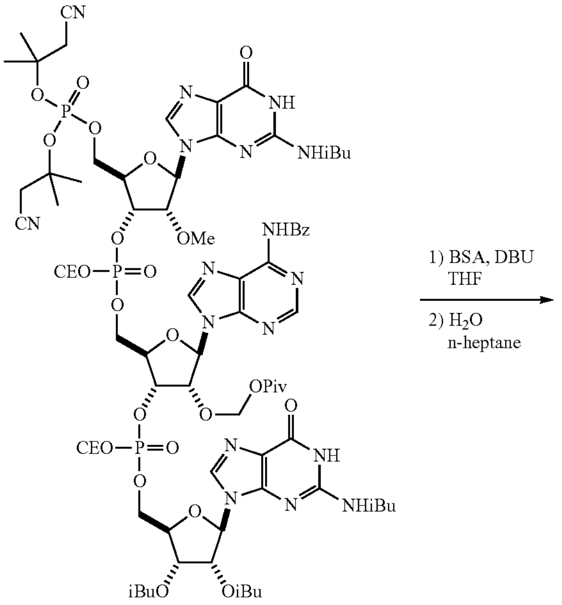

11s

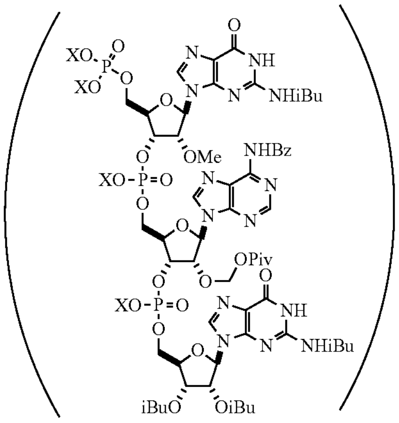

X = H or DBU-$H^+$

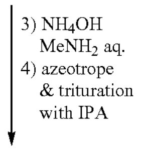

-continued

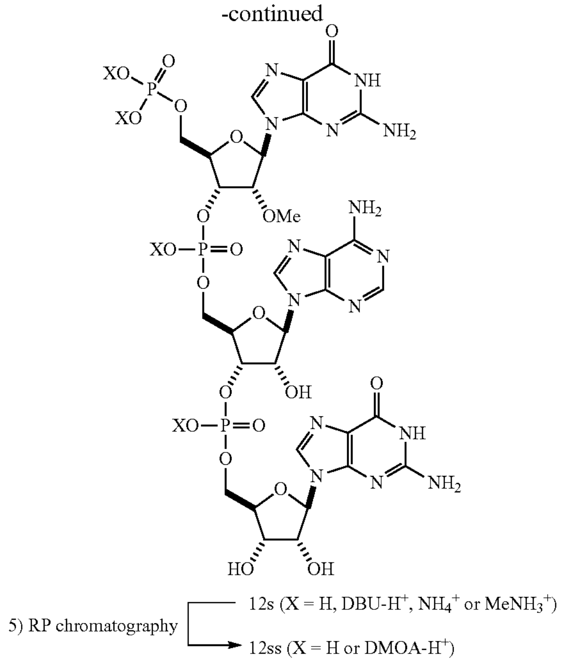

11 s (56 g, 36 mmol, 1 equiv., 1 wt, 1 vol) was azeotroped with THF (500 ml×2, 9 vols×2) and re-dissolved in THF (250 ml, 4.5 vols). N,O-Bis(trimethylsilyl)acetamide (BSA; 120 ml, 2.1 vols, 491 mmol, 15 equiv.) was added at ambient temperature. After 5 min, the mixture was cooled to −10° C. and 1,8-diazabicyclo[5.4.0]undec-7-ene (DBU; 73 ml, 1.3 vols, 0.49 mol, 15 equiv.) was added. The mixture was let warm up and stirred for 2 hours. The mixture was diluted with n-heptane (500 ml, 9 vols) and cooled to −10° C. Water (56 ml, 1 vol) was added and the resultant biphasic mixture was allowed to warm up to ambient temperature under vigorous stirring. The upper layer was removed by decantation. The trituration/decantation cycle was repeated with n-heptane (500 ml, 9 vols). To the bottom layer were added 28 wt %4 ammonium hydroxide ($NH_4OH$; 112 ml, 2 vols, 1.66 mol, 51 equiv.) and 40 wt %/o methylamine in water ($MeNH_2$; 112 ml, 2 vols, 1.3 mol, 40 equiv.). The resultant mixture was stirred at ambient temperature overnight. The mixture was diluted with IPA (500 ml, 9 vols) and concentrated. Azeotrope was repeated with IPA (500 ml×4, 9 vols×4) and the resultant oil/solid was suspended in IPA (1 L, 18 vols) and filtered. Wet filter cake was transferred back to the reactor/flask and dried under vacuum to give crude 12 s (crude salts of amine mixture; 38 g) as yellow solid.

12 s crude salts from 29.8 g scale (17 mmol) global deprotection of Is was subjected to polymer C18 reverse phase column chromatography (A: 10 mM dimethyloctylammonium bicarbonate (DMOAB) buffer, B: acetonitrile; gradient: 0-50% B) to give 12ss DMOA salt (13.0 g, 12.4 mmol, 73% yield) as a white solid.

Global Deprotection—Alternate Method for Isolation of Crude 12 s:

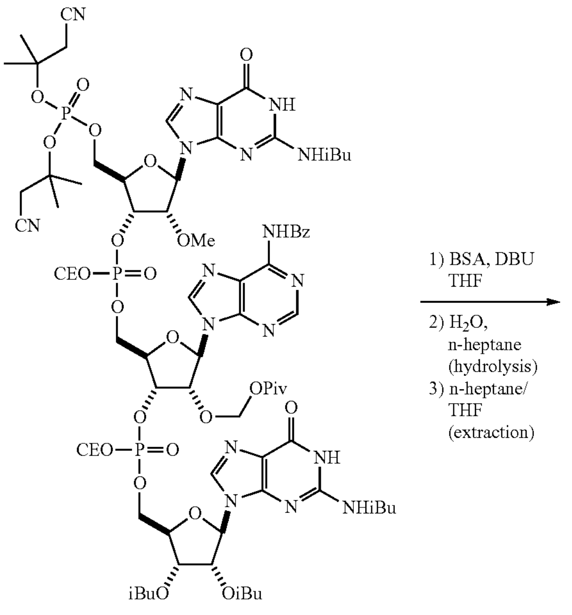

11s

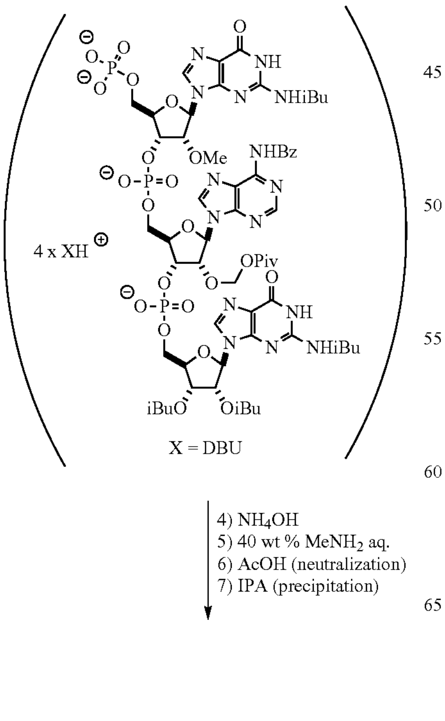

-continued

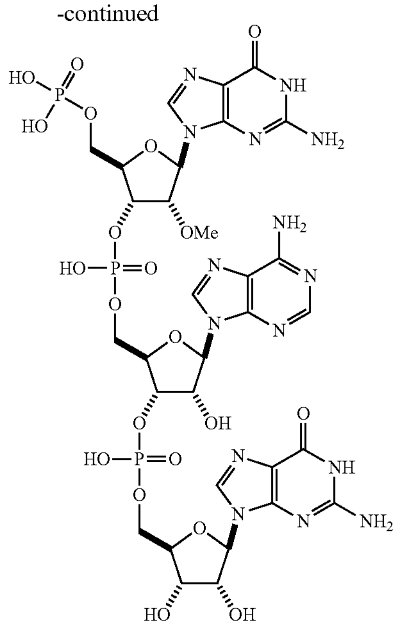

12s crude 11 s (400 g, 220 mmol, 1 equiv., 1 wt, 1 vol) was azeotroped with THF (2000 ml, 5 vols), transferred to a 12 L reactor with anhydrous THF (the total THF volume was adjusted at 4 vols) and cooled down to 12° C. N,O-Bis (trimethylsilyl)acetamide (BSA; 645 ml, 1.61 vols, 2.64 mmol, 12 equiv.) was added while maintaining an internal temperature (T-internal) of ≤18° C. The mixture was cooled down to 0° C. and 1,8-diazabicyclo[5.4.0]undec-7-ene (DBU; 395 ml, 0.988 vols, 2.64 mol, 12 equiv.) was added while maintaining an internal temperature of ≤3° C. Upon complete addition, the mixture was stirred at 0-5° C. for 1 hour and cooled down to −5° C. The mixture was diluted with n-heptane (3200 ml, 8 vols) and re-cooled to −3° C. Water (300 ml, 0.75 vol) was added while controlling exotherm (T-internal 518° C.) to give a biphasic mixture. The upper layer was removed, and the bottom layer was washed with heptane/THF (2:1; 2400 ml×2, 6 vols×2). To the aqueous bottom layer was added 28 wt % ammonium hydroxide ($NH_4OH$; 600 ml, 1.5 vols, 8.9 mol, 40 equiv.). After overnight stirring, 40 wt % methylamine in water ($MeNH_2$; 600 ml, 1.5 vols, 6.9 mol, 32 equiv.) was added and stirring was continued for an additional ≥6 hours. The mixture was cooled down to −5° C. and neutralized by dropwise addition of acetic acid (1000 ml, 2.5 vols, 15.5 mol, 80 equiv.) while maintaining T-internal below 15° C. Upon complete addition, the mixture was diluted with 2-propanol (6400 ml, 16 vols) and the yellow suspension thus formed was subjected to centrifuge at 3000 rpm for 10 min. The yellow supernatant was removed by decantation. Off-white pasty solid at the bottom was rinsed by repeated cycles of trituration, centrifuge and decantation with: (1) 2-propanol/water (4:1, 2000 ml, 5 vols) and (2) 2-propanol (2000 ml, 5 vols). The final wet solid was dried in a vacuum oven at 35° C. to give crude 12 s as an off-white solid (230.4 g, 219 mmol, 0.576 wt).

$^1$H-NMR (DMSO-$d_6$, 300 MHz) δ (ppm)=10.67 (bs, 2H), 8.42 (s, 1H), 8.08 (s, 1H), 7.95 (s, 1H), 7.87 (s, 1H), 7.23 (bs, 2H), 6.63 (bs, 2H), 6.56 (bs, 2H), 5.86 (d, J=7.9 Hz, 1H), 5.79 (d, J=7.3 Hz, 1H), 5.64 (d, J=6.5 Hz, 1H), 4.80 (m, 2H), 4.63 (m, 1H), 4.49 (m, 1H), 4.34 (m, 1H), 4.16-4.28 (m, 3H), 3.75-4.05 (m, 7H), 3.21 (s, 3H), 2.82 (m, 6H), 2.60 (s, 18H), 1.50 (m, 6H), 1.12 (s, 30H), 0.75 (m, 9H).

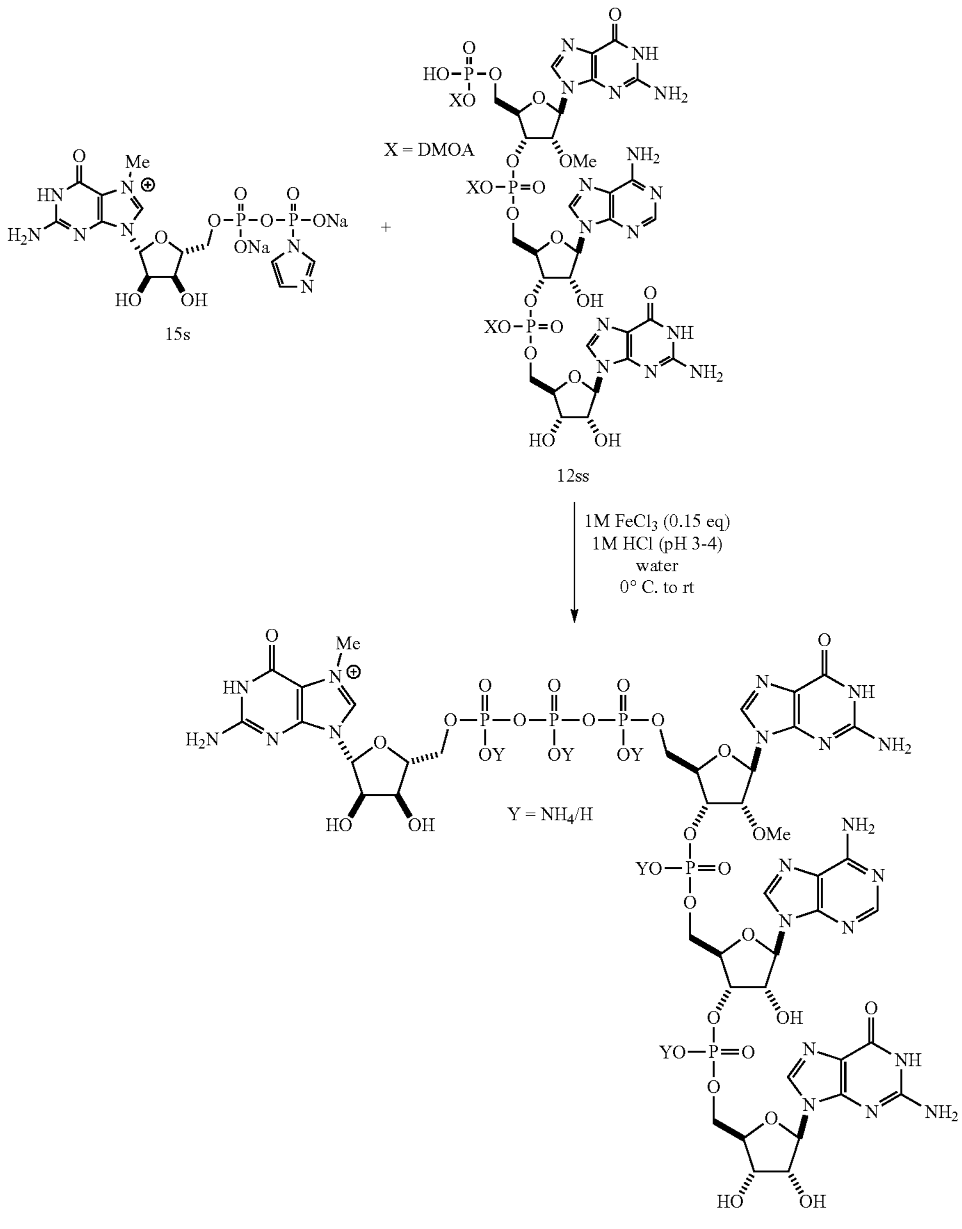

15s

12ss

16s 15 s (50.0 g, 90.5 mmol) was dissolved in 0.2 L Milli-Q water and filtered through a filter funnel. The yellow filtrate was transferred to a volumetric flask and the total volume was adjusted to 250 ml with Milli-Q water. 15s stock solution thus obtained (20% (w/v) in water, 0.36 mmol/ml) was stored in a refrigerator (5° C.) until use.

12ss (23.85 g, 15.65 mmol, 1 wt, 1 vols, 1 eq) was dissolved in Milli-Q water (72 ml, 3.0 vols). 15 s stock solution (138 ml, 5.8 vols, 50 mmol, 3.2 eq) was added, and the mixture was cooled to 5° C. (pH~8). 1M HCl was added dropwise to adjust the pH to 5 (39 ml, 1.6 vols, 39 mmol, 2.5 eq), and then 1 M $FeCl_3$ (2.35 ml, 0.1 vol, 2.35 mmol, 0.15 eq) was added dropwise. 1M HCl was added dropwise to adjust pH at 3 (40 ml, 1.7 vols, 40 mmol, 2.6 eq) and the mixture was allowed to warm up to 20° C. After 6 h, 15 s stock solution (17.3 ml, 0.73 vols, 6.2 mmol, 0.4 eq) was added, and the mixture was cooled to 0° C. (pH 4). 1 M HCl (5 ml, 0.2 vols, 5 mmol, 0.3 eq) was added to adjust the pH to 3. After overnight stirring (19 h, pH 4, 13° C.), the pH was re-adjusted to 3 with 1 M HCl (5 ml, 0.2 vols, 5 mmol, 0.3 eq). After 2 h, the mixture was filtered through a filter funnel and rinsed with Milli-Q water to give 570 g of a yellow solution, which was subjected to purification by a combination of tangential flow filtration (TFF) and anion-exchange chromatography (AEX) to give 16 s (net 12.2 g, 0.51 wt, 8.17 mmol, 52% yield) as an aqueous solution of ammonium ($NH_4$) salt form.

Alternatively, in a 3 L flask, 12ss (57.00 g, 37.4 mmol, 1 wt, 1 vol, 1 eq) was dissolved in Milli-Q water (171 ml, 3.0 vols). In a 500 ml flask, 15 s (82.65 g, 1.45 wt, 150 mmol, 4.0 eq) was dissolved in Milli-Q water (256 ml, 4.5 vols). The resultant suspension was filtered through a 20-micron polyethylene filter funnel and the filtrate was added to the main reactor. Extra Milli-Q water (28.5 ml, 0.5 vols) was used for complete rinse, filtration, and transfer. The combined mixture was cooled to ≤5° C. (pH~8) and the pH was adjusted down to 5 by dropwise addition of 1M HCl (112 ml+18.7 ml+9.4 ml=140.1 ml, 2.46 vols, 140 mmol, 3.75 eq) at 3-5° C. 1 M $FeCl_3$ (5.62 ml, 0.1 vol, 5.62 mmol, 0.15 eq) was added dropwise and the pH was adjusted down to 2-3 by dropwise addition of 1M HCl (74.8 ml+18.7 ml+8 ml=101.5 ml, 1.78 vols, 102 mmol, 2.71 eq) at 3-5° C. Upon complete addition, the mixture was allowed to warm up to 20° C. After 7 h, the mixture was cooled to <5° C., adjusted to pH 2 by dropwise addition of 1 M HCl (6.0 ml, 0.11 vols, 6 mmol, 0.16 eq), and then allowed to warm up to 20° C. After overnight stirring, the mixture was filtered through a 20-micron polyethylene filter funnel and rinsed with Milli-Q water (114 ml, 2 vols) to give 0.95 kg yellow solution, which was combined with small-scale 16 s crude filtrate obtained from similar processes (1.39 mmol scale; AE-405). The combined crude 16 s (corresponds to 38.8 mmol theoretically) was subjected to purification by a combination of tangential flow filtration (TFF; Sartorius Hydrosart® 2 kDa) and anion-exchange chromatography (AEX; TOSOH SuperQ, Cytiva ÄKTA™ pilot, $NH_4Cl$ buffer) to give 16 s (net 35.9 g, 24.06 mmol, 62% yield) as an aqueous solution of the ammonium ($NH_4^+$) salt form.

$^1$H-NMR (DMSO-$d_6$ with 10% v/v $D_2O$, 300 MHz) δ (ppm)=9.60 (s, 1H), 8.48 (s, 1H), 8.17 (s, 1H), 8.02 (s, 1H), 7.96 (s, 1H), 7.43 (br, 1H), 5.92 (d, J=7.2 Hz, 1H), 5.82 (s, 1H), 5.79 (m, 1H), 5.68 (d, J=5.6 Hz, 1H), 4.88 (m, 2H), 4.67 (m, 1H), 4.53-4.57 (m, 2H), 4.46 (m, 1H), 4.40 (m, 1H), 4.29-4.33 (m, 3H), 3.95 (s, 3H), 3.85-4.15 (m, 10H), 3.24 (s, 3H).

Example 2: One-Pot Trinucleotide Assembly (a)

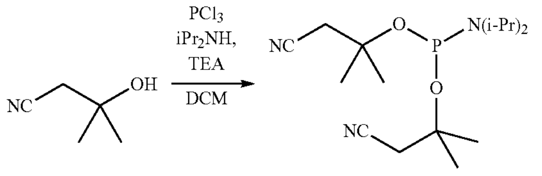

2s

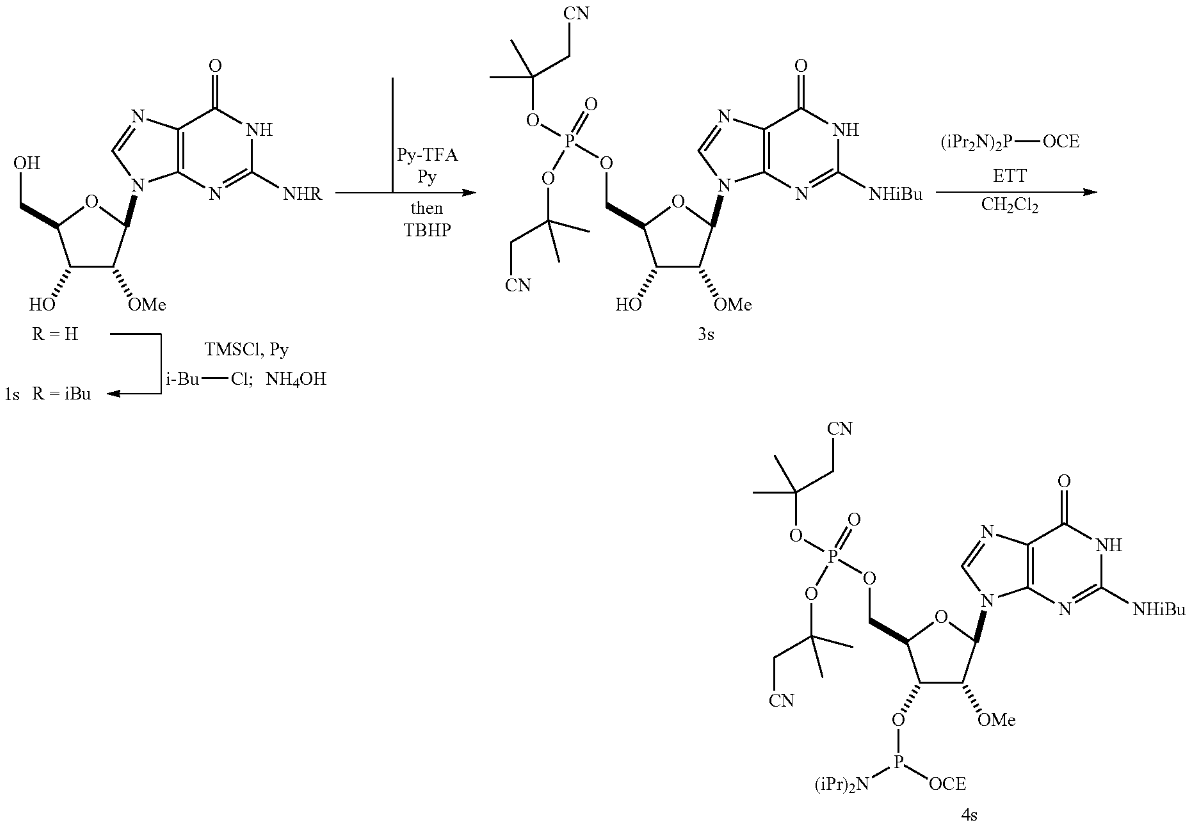

1s

3s

4s

-continued
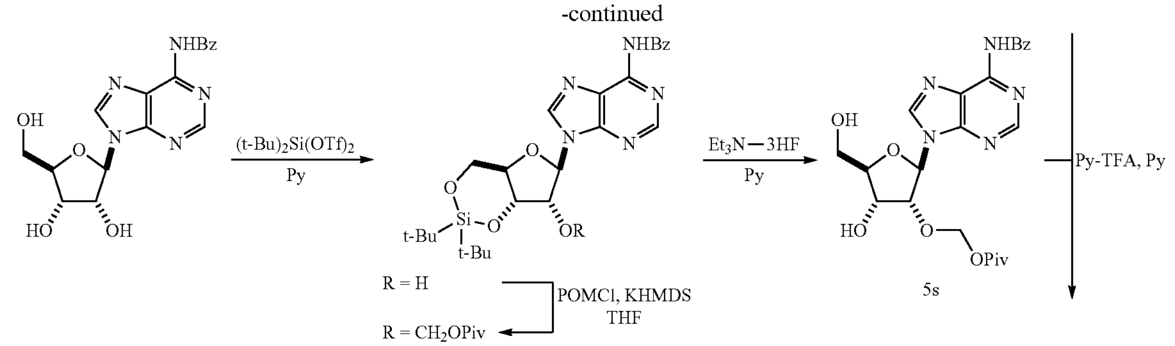
5s
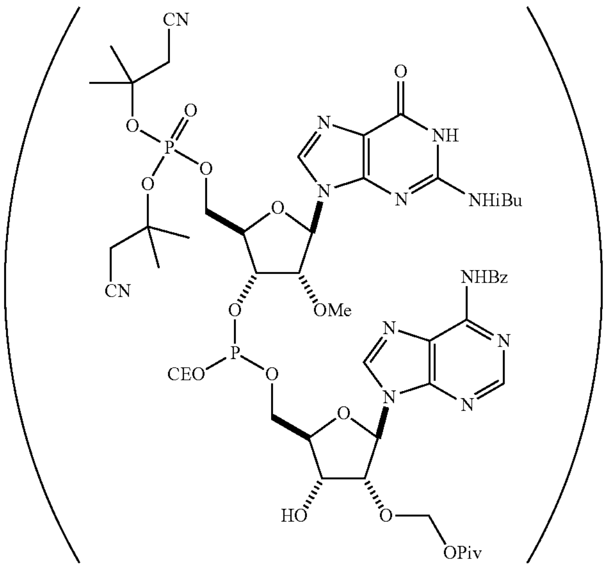
6s-P(III)P(V)
(b)
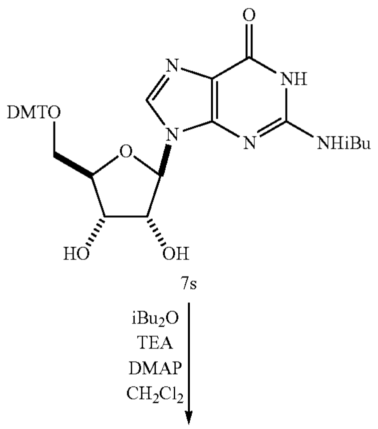
7s

-continued
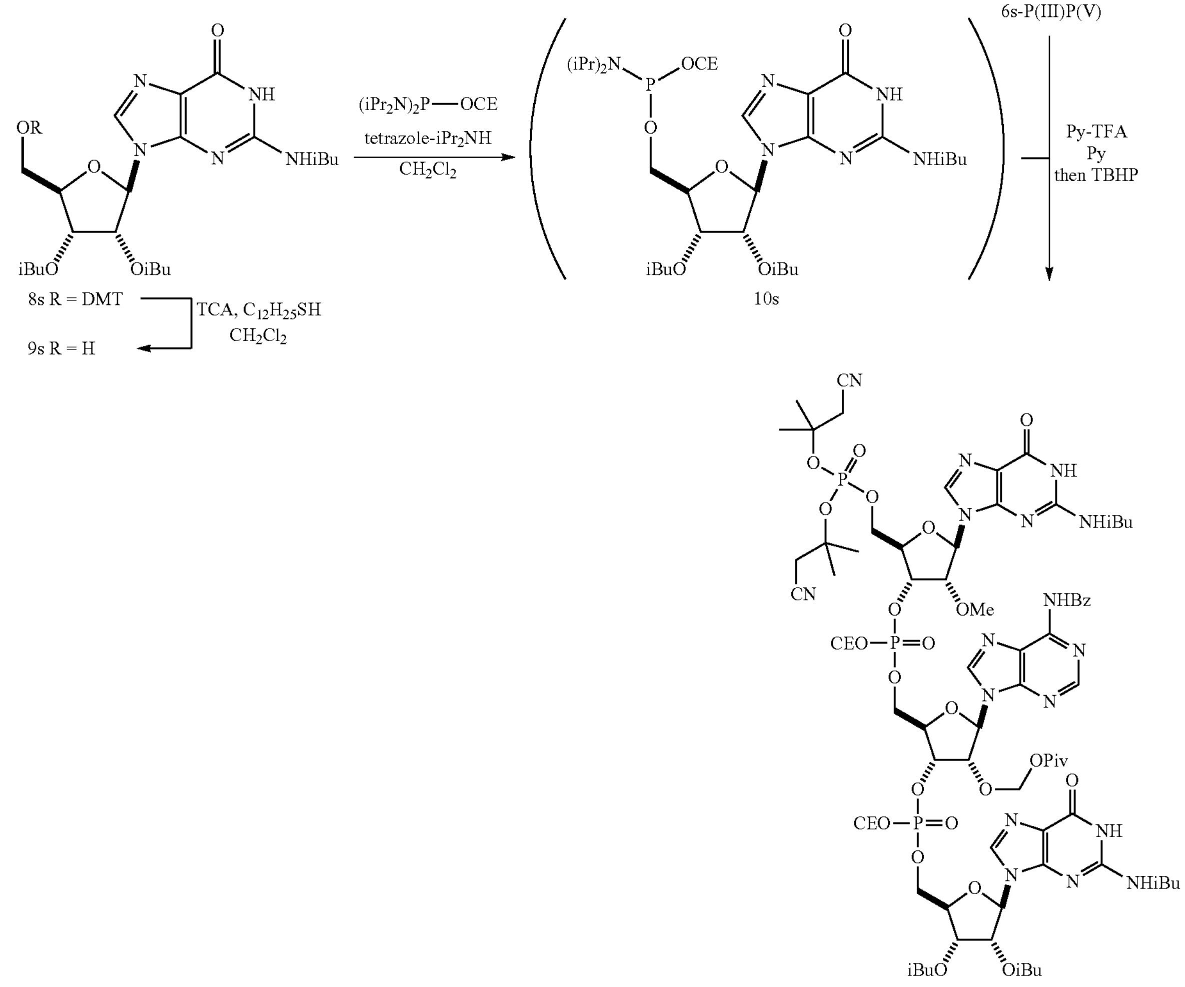
11s
(c)
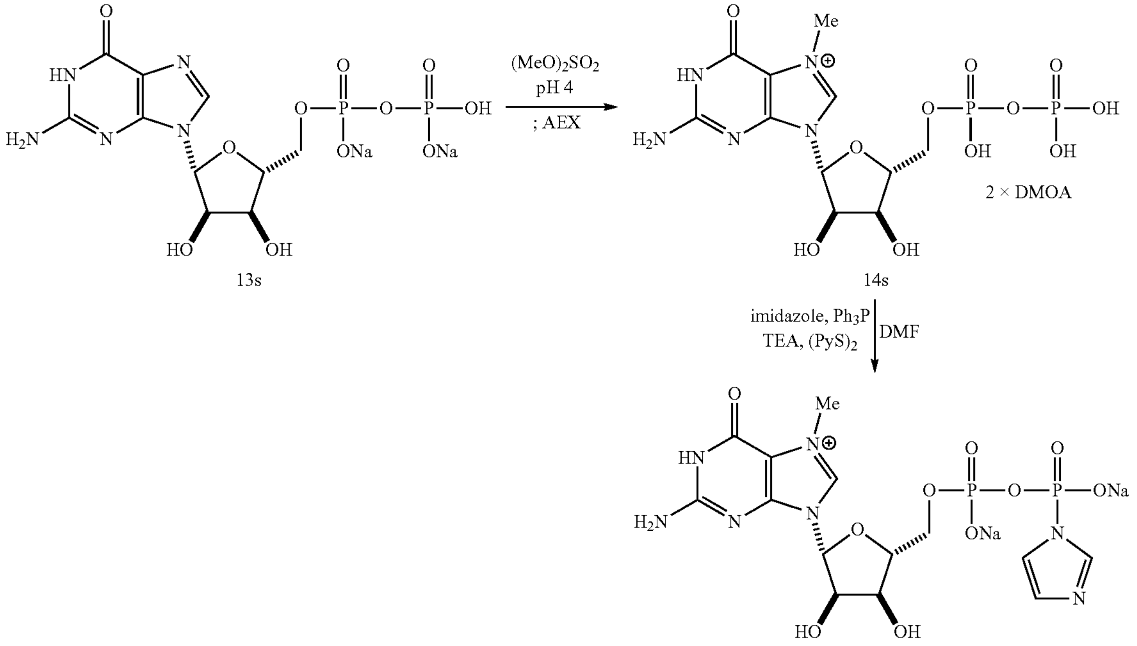
15s

-continued
(d)
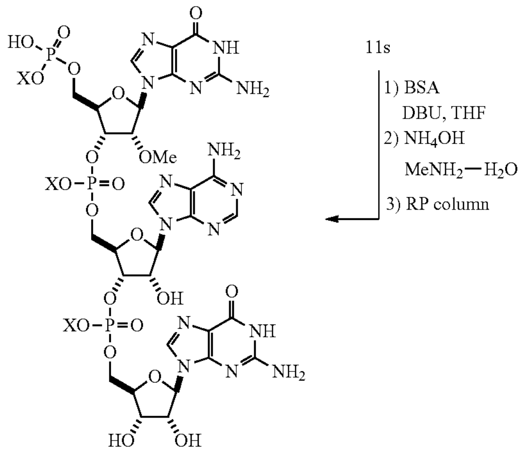
12ss (X = DMOA)
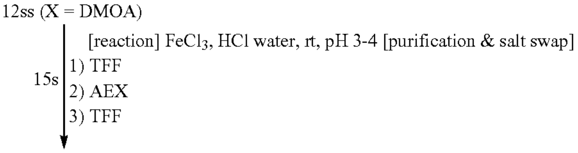
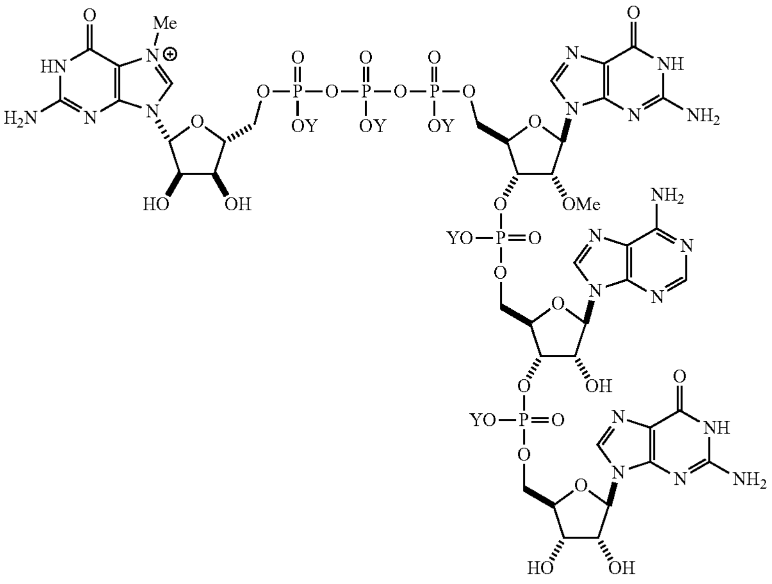
Y = $NH_4$
16s Steps not described below were performed as described in Example 1.

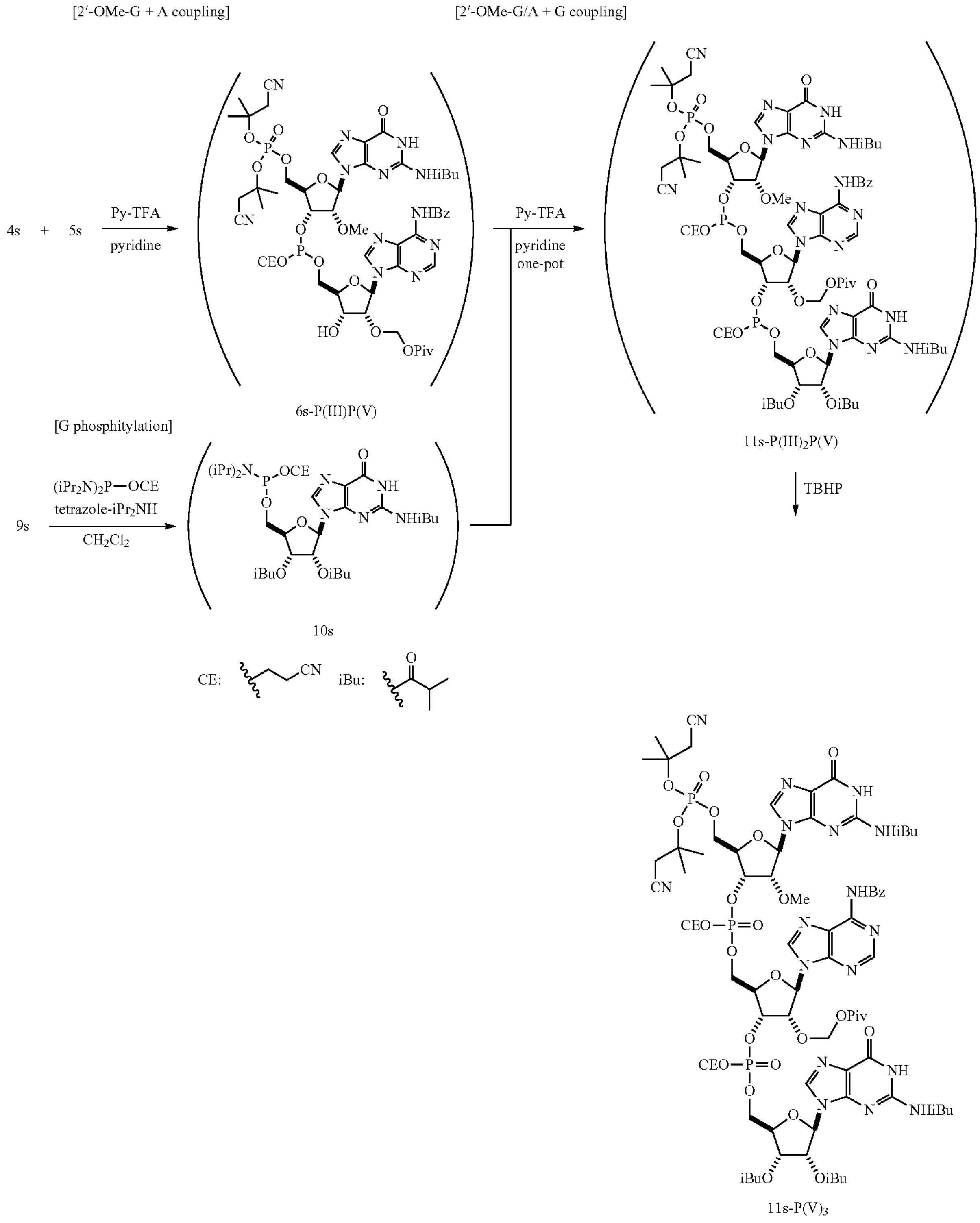

G-Phosphitylation:

9 s (325.2 g, 659 mmol, 1.6 equiv.) was azeotroped with acetonitrile (1 L×2, 5 vols×2) and suspended in $CH_2Cl_2$ (400 ml, 2 vols). 2-Cyanoethyl N,N,N',N'-tetraisopropylphosphorodiamidite (220 g, 730 mmol, 1.77 equiv.) was azeotroped with acetonitrile (1 L) and consolidated into 9 s with DCM (1 L). The resultant mixture was cooled to below −10° C. and diisopropylammonium tetrazolide (11.29 g, 65.9 mmol, 0.16 equiv.) was added. The reaction was allowed to warm up to ambient temperature and stirred overnight to give 10 s solution (theoretical 100/6 yield assumed, 659 mmol, 1.6 equiv.), which was used directly for 2'-OMe-G/A+G coupling.

2'OMe-G+A Coupling:

5 s (200 g, 412 mmol, 1 equiv., 1 wt, 1 vol) was azeotroped with pyridine (1 L×2, 5 vols×2) and diluted with pyridine (300 ml, 1.5 vols). Pyridine trifluoroacetate ("Py-TFA", 159 g, 825 mmol, 2.00 equiv.) was azeotroped with pyridine (1 L×2, 5 vols×2) and re-dissolved in pyridine (800 ml, 4 vols) to give Py-TFA solution-1.4 s (stock solution in acetonitrile, 0.449 mmol/g, 1285 g, 577 mmol, 1.40 eq) was concentrated, azeotroped with pyridine (1 L, 5 vols) to remove 900 ml (4.5 vols) pyridine and diluted with pyridine (300 ml, 1.5 vols). 5 s was transferred into a 12 L reactor and rinsed with pyridine (100 ml×2, 0.5 vol×2). 4 s was consolidated into 5 s and rinsed with pyridine (100 ml×2, 0.5 vol×2). The resultant mixture was cooled to <−10° C., and Py-TFA solution 1 was added. The mixture was let warm up, stirred at −3 to 2° C. for 2-3 hours, and cooled to <−5° C. to give 6 s, which proceeded directly to 2'OMe-G/A+G coupling.

2'OMe-G/A+G Coupling:

Pyridine trifluoroacetate (159 g, 825 mmol, 2.00 equiv.) was azeotroped with pyridine (1 L×2, 5 vols×2) and re-dissolved in pyridine (1 L, 5 vols) to give Py-TFA solution-2. The separately prepared 10 s solution (659 mmol, 1.6 equiv.) was added to 6 s (rinsed with 100 ml $CH_2Cl_2$, 0.5 vol) followed by Py-TFA solution-2. The resultant mixture was stirred at 0-14° C. for 3-4 hours then treated with TBHP (5-6 M solution in decane, 225 ml, 3 eq, 1.2 mol) overnight. The mixture was poured into pre-cooled (5° C.) biphasic mixture of toluene (4 L, 20 vols) and 10 wt % aqueous sodium sulfite ($Na_2SO_3$; 1.04 kg, 2.0 equiv.) (200 ml $CH_2Cl_2$ and 500 ml toluene were used for rinse and complete transfer). The mixture was diluted with water (1 L, 5 vols) and stirred for extraction. The top layer was separated and set aside. The bottom layer was extracted with $CH_2Cl_2$ (2 L×2, 10 vols×2). All the organic layers were combined, concentrated, and partitioned between 10 wt % aqueous potassium bicarbonate ($KHCO_3$; 1.65 kg, 4.0 equiv.) and $CH_2Cl_2$ (6 L, 30 vols). The organic layer was separated and set side. The aqueous layer was extracted with $CH_2C_{12}$ (1 L, 5 vols). All the organic layers were combined, washed with 10 wt % sodium chloride (NaCl; 1.20 kg, 6 wt), and phase separation was allowed overnight. The organic layer was collected, concentrated, and azeotroped with toluene (4 L, 20 vols). The crude mixture thus obtained was subjected to silica gel plug filtration (2 kg $SiO_2$×2, $CH_2Cl^2$/EtOH 0-40%) to give its as a mixture of products with and without partial loss of 2-cyanoethyl (CE) group (yellow dry foam, 782 g).

Example 3: Further Optimization of One-Pot Trinucleotide Assembly

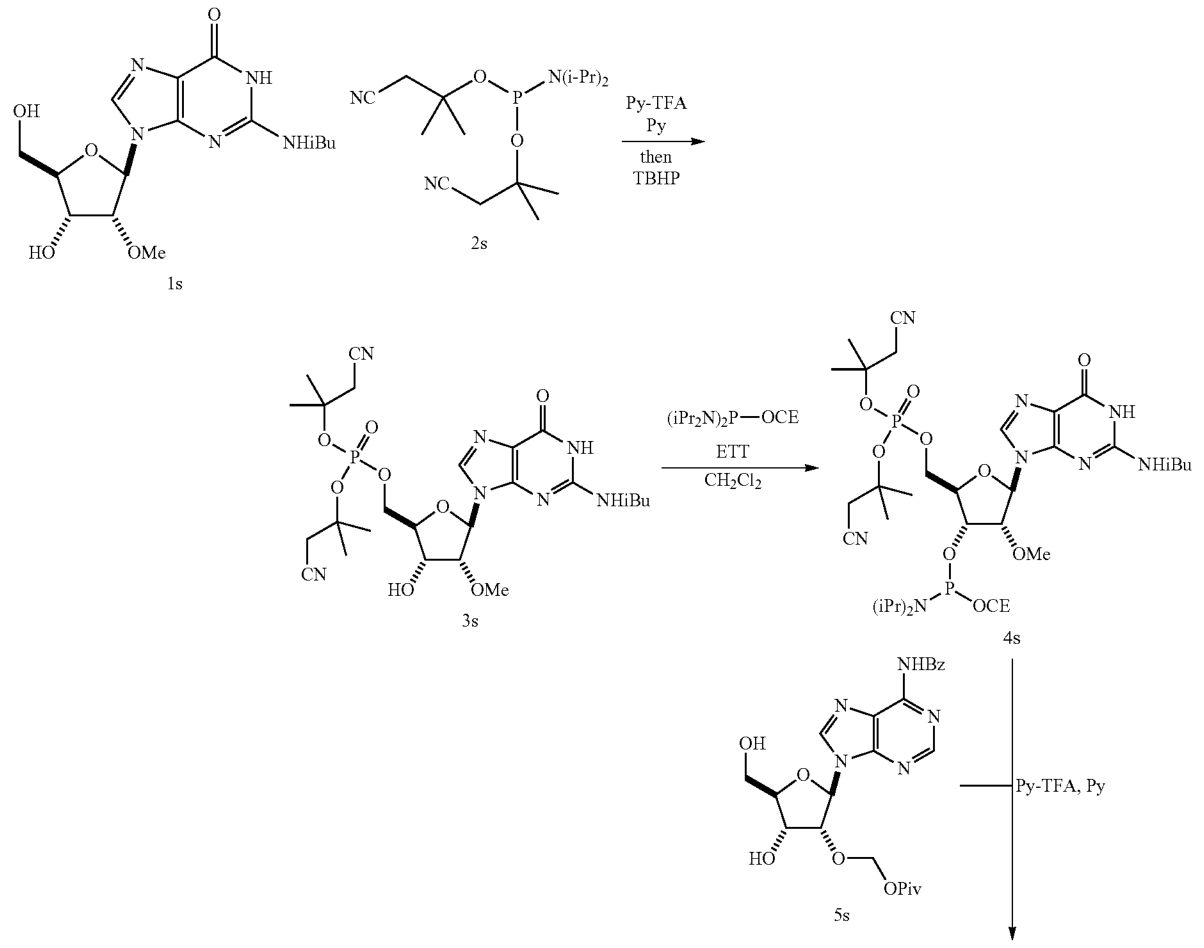

1s 2s 3s 4s 5s

-continued
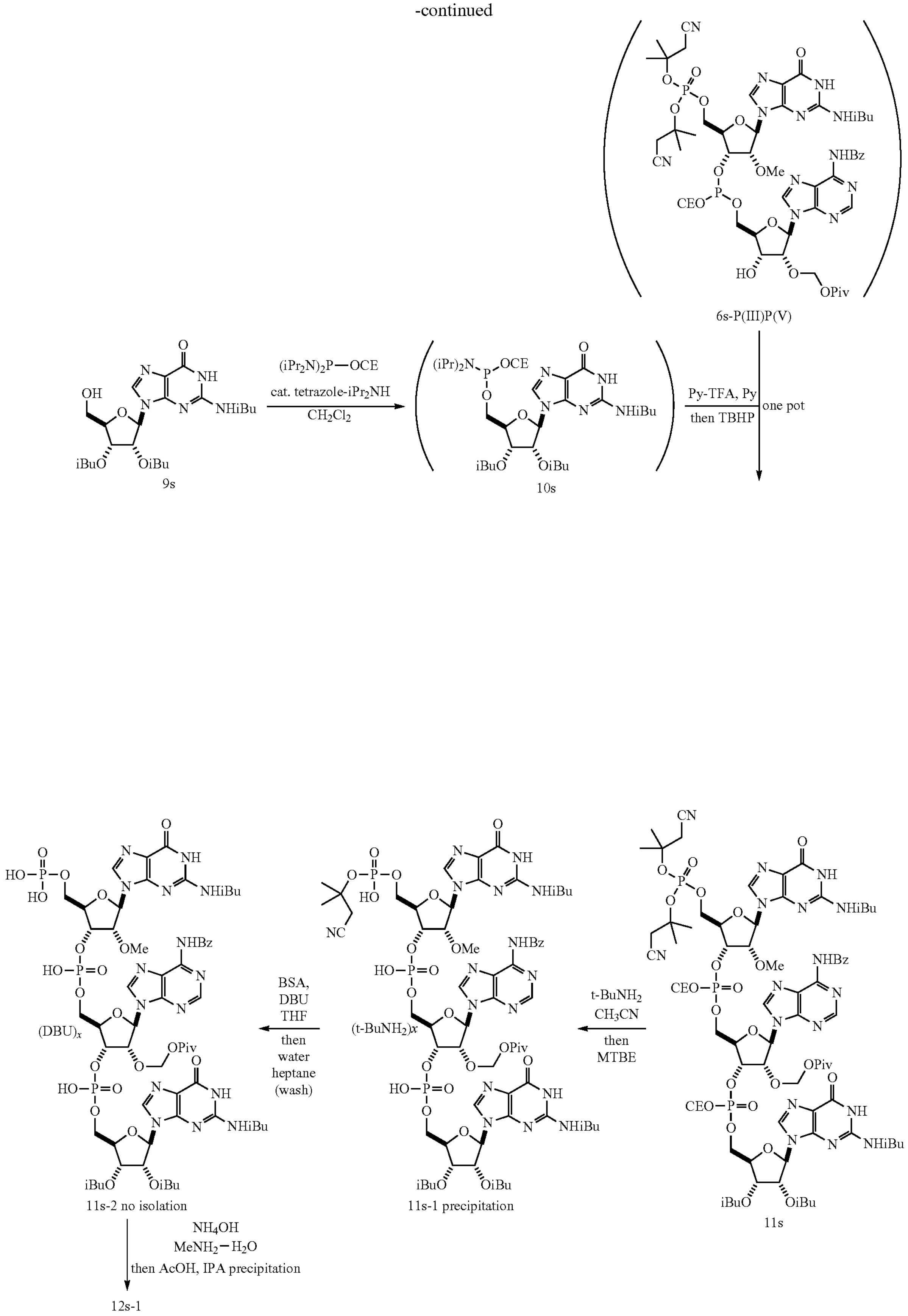
9s
10s
6s-P(III)P(V)
11s
11s-1 precipitation
11s-2 no isolation
12s-1

-continued
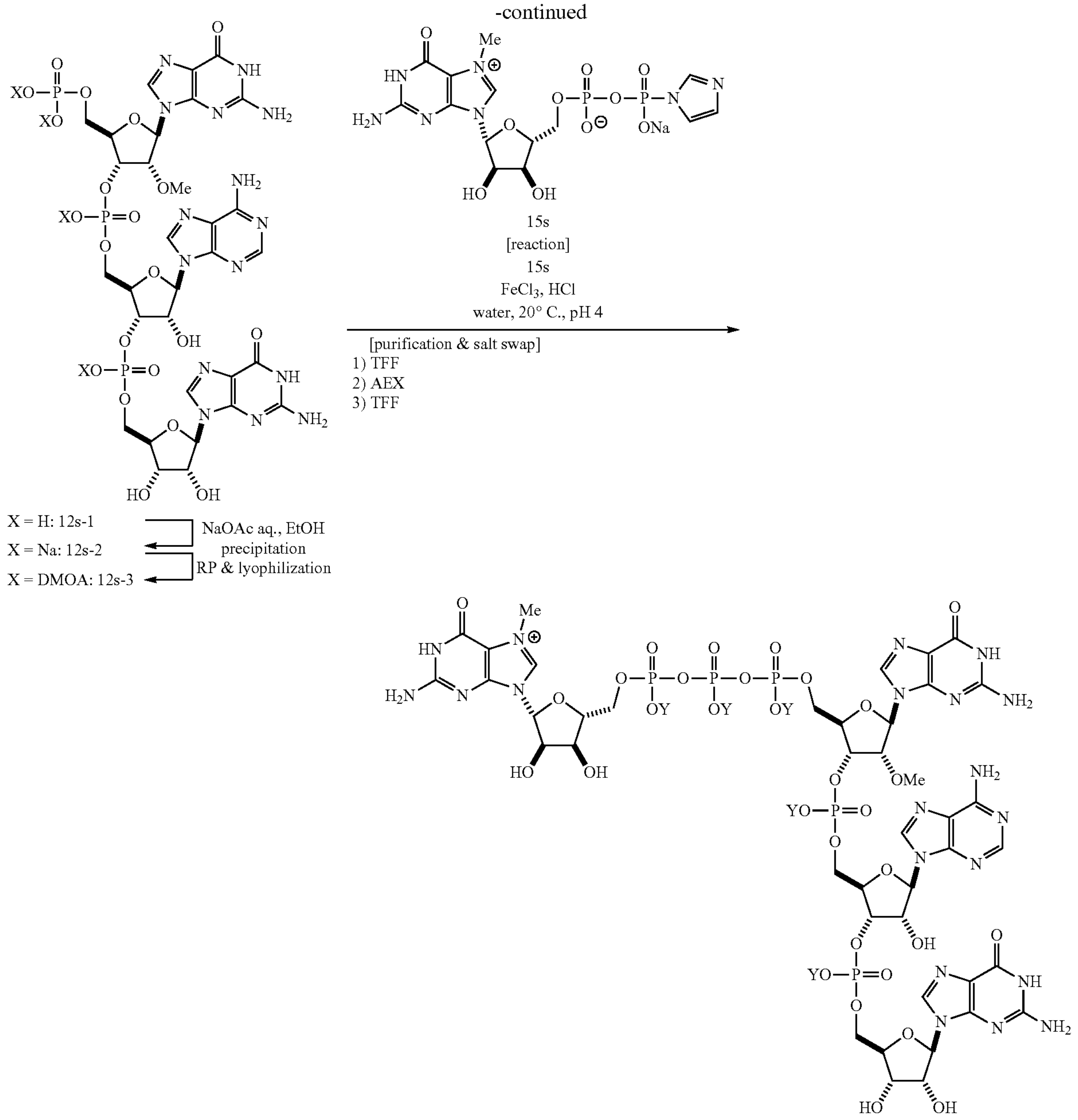
Y = $NH_4$
16s
Steps not described below were performed as in Examples 1 and 2.
Synthesis of Fully Protected Trinucleotide 11 s

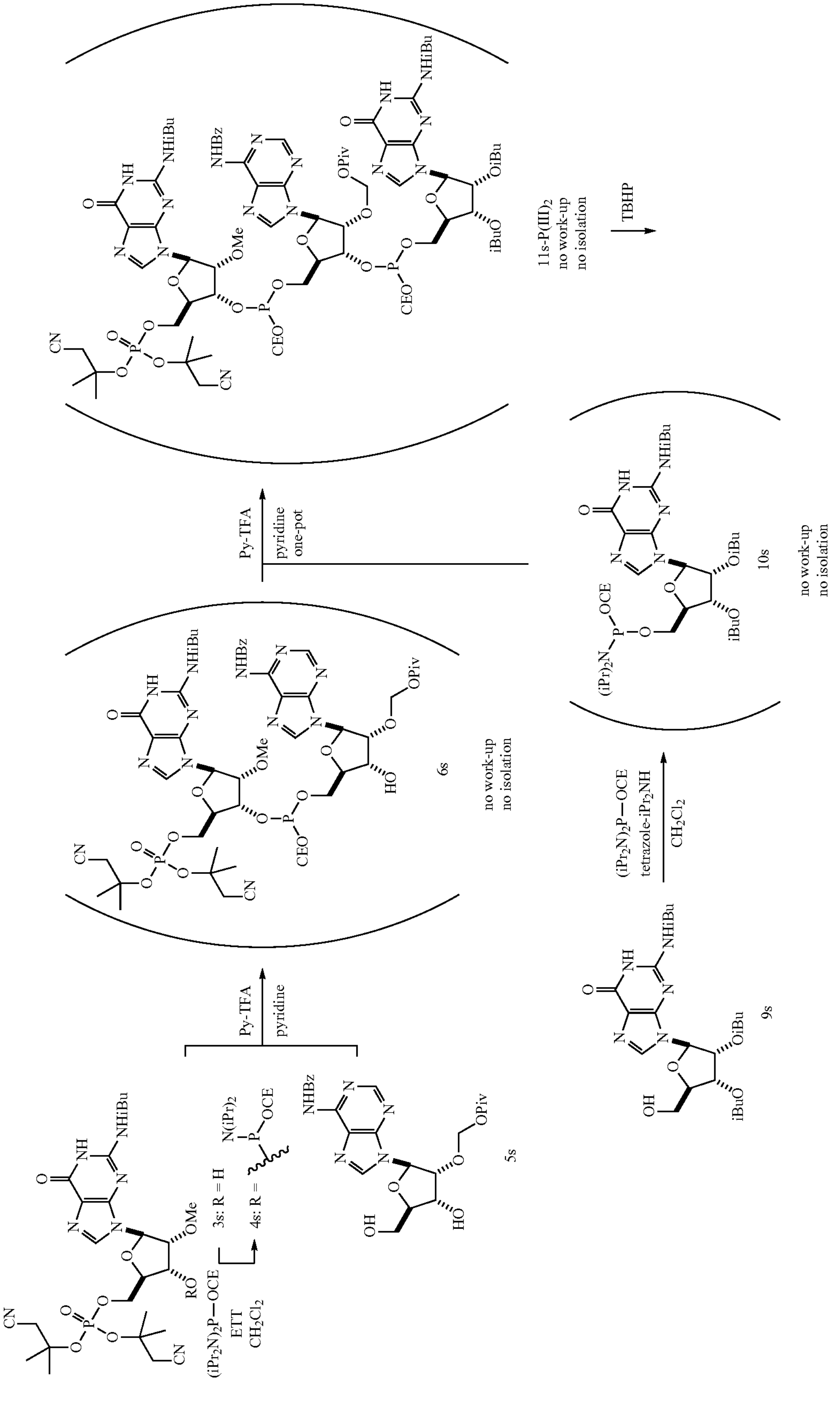
$(iPr_2N)_2P$—OCE
ETT
$CH_2Cl_2$
3s: R = H
4s: R =
5s
Py-TFA
pyridine
6s
no work-up
no isolation
Py-TFA
pyridine
one-pot
9s
$(iPr_2N)_2P$—OCE
tetrazole-$iPr_2NH$
$CH_2Cl_2$
10s
no work-up
no isolation
11s-P(III)$_2$
no work-up
no isolation
TBHP -continued
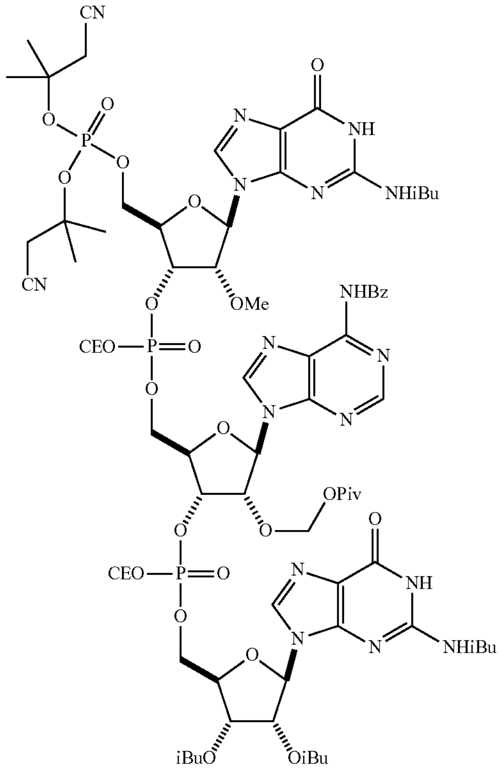
11s
(& partial loss of protecting groups)

Azeotropic Drying of Raw Materials 5 s (300 g, 1 wt, 1 vol, 618 mmol, 1 eq) was azeotroped with pyridine (1.5 L, 5 vols) to distill off 1.2 L pyridine. Azeotrope was repeated with pyridine (1.5 L, 5 vols) to distill off 1.45 L pyridine (0.35 L pyridine remains). The material was protected from air and moisture.

3 s (452 g, 1.51 wt, 741 mmol, 1.2 eq) was azeotroped with acetonitrile (1.5 L, 5 vols) to distill off 1.36 L acetonitrile. Azeotrope was repeated with acetonitrile (1.5 L, 5 Vols) to distill off 1.4 L acetonitrile. The material was protected from air and moisture.

9 s (427 g, 1.42 wt, 856 mmol, 1.4 eq) was suspended in acetonitrile (1.5 L, 5 vols) and azeotroped to distill off 1.3 L acetonitrile. Azeotrope was repeated with acetonitrile (1.5 L, 5 Vols) to distill off 1.5 L acetonitrile. The material was protected from air and moisture.

$(iPr_2N)_2P$—OCE (224 g, 0.75 wt, 742 mmol, 1.2 eq) was azeotroped with acetonitrile (900 mL, 3 vols) to distill off 830 mL acetonitrile. Azeotrope was repeated with acetonitrile (900 vols) to distill off 860 mL acetonitrile (0.1 L remains).→$(iPr_2N)_2P$—OCE-1

$(iPr_2N)_2P$—OCE (279 g, 0.93 wt, 927 mmol, 1.5 eq) was azeotroped with acetonitrile (900 mL, 3 vols) to distill off 820 mL acetonitrile. Azeotrope was repeated with acetonitrile (900 vols) to distill off 885 mL acetonitrile (0.1 L remains).→$(iPr_2N)_2P$—OCE-2

Py-TFA (239 g, 0.80 wt, 1.24 mol, 2.0 eq) was azeotroped with pyridine (1.2 L, 4 vols) to distill off 1.1 L pyridine. Azeotrope was repeated with pyridine (1.2 L, 4 vols) to distill off 1.2 L pyridine (100 mL left). The material was protected from air and moisture.→Py-TFA-1

Py-TFA (239 g, 0.80 wt, 1.24 mol, 2.0 eq) was azeotroped with pyridine (1.2 L, 4 vols) to distill off 1.1 L pyridine. Azeotrope was repeated with pyridine (1.2 L, 4 vols) to distill off 1.22 L pyridine (80 mL left). The material was protected from air and moisture.→Py-TFA-2

Synthesis of 10s

The previously azeotroped 3 s was diluted with DCM (1.5 L, 5 vols). The previously azeotroped $(iPr_2N)_2P$—OCE-1 (1.2 eq) was added by dilution with DCM (900 mL, 3 vols). The resultant mixture was cooled to −10° C. and treated with ETT (96.5 g, 0.32 wt, 741 mmol, 1.2 eq). The cooling bath was removed, and the mixture was allowed to warm up to ambient temperature. After overnight stirring, the reaction mixture was diluted with hexanes (1.2 L, 4 vols), stirred for 10 minutes, and filtered to remove insoluble solid (110.2 g of white solid collected). The reactor and filter cake were rinsed with DCM-hexanes 2:1 (v/v) (900 mL, 3 vols) and the collected filtrate was concentrated to give crude 4 s (814.71 g; theoretical yield: 600 g).

Dinucleotide Coupling—Synthesis of 6s 4 s was transferred into a 12 L reactor by dilution with pyridine (1.2 L, 4 vols). The previously azeotroped 5 s (300 g, 618 mmol, 1 eq) was consolidated into crude 4 s by dilution with pyridine (900 mL, 3 vols), and the resultant mixture was cooled to −10° C. The previously azeotroped Py-TFA-1 was diluted with pyridine (1.2 L, 4 vols) and added to the reactor (post-addition: −4.9° C.). Once T-internal dropped to <−10° C. (10 min), the cooling bath was removed, and the mixture was allowed to warm up. IPC samples were taken and analyzed at 1 h (6.8° C.) and 2 h (16.2° C.) timepoints to monitor consumption of 5 s and formation of 6 s.

One-Pot Trinucleotide Coupling—Synthesis of 11s

The reaction was cooled to −2.3° C. and 10 s solution was added (post-addition: 7.5° C.). After T-internal dropped to 3° C., the previously azeotroped Py-TFA-2 was diluted with pyridine (1.2 L, 4 vols) and added to the reactor (post-addition. 5.4° C.; 25 min: 0.6° C.). The mixture was allowed to warm up. IPC sample was taken at 5 h timepoint (18° C.) to monitor consumption of 6 s and formation of 11s-$P(III)_2$. The mixture was cooled down to −1.4° C. and TBHP (314 mL, 1.05 vols, 1.7 mol, 3 eq) was added over 0.3 h (post addition: 1.3° C.). The cooling bath was removed, and the mixture was allowed to warm up to ambient temperature for overnight reaction (14 h from TBHP addition).

Work-Up

The coupling reaction mixture was added to a pre-chilled (0° C.) mixture of toluene (6.0 L, 20 vols) and 10 wt % $Na_2SO_3$ aq. (776 g, 2.6 wts, 615 mmol, 1 eq) under stirring. Water (3.0 L, 10 vols) was added, and stirring was continued for 10 min. The mixture was allowed for phase separation (3 layers) and the bottom two layers (7.5 L) were collected (Aq-1). The top layer was separated and set aside (Org-1). The aqueous layers (Aq-1) were back-extracted with DCM (4.0 L, 13 vols) to separate organic layer (Org-2) and aqueous layer (Aq-2; no product). Org-1 and Org-2 were combined, concentrated and reconstituted in DCM (4.5 L, 15 vols). The mixture was washed with 5 wt % NaCl aq. (3.0 kg, 10 wts, 2.5 mol, 4 eq) and concentrated to give crude 11 s as thick orange syrup (1753 g).

Partial Deprotection of Phosphates

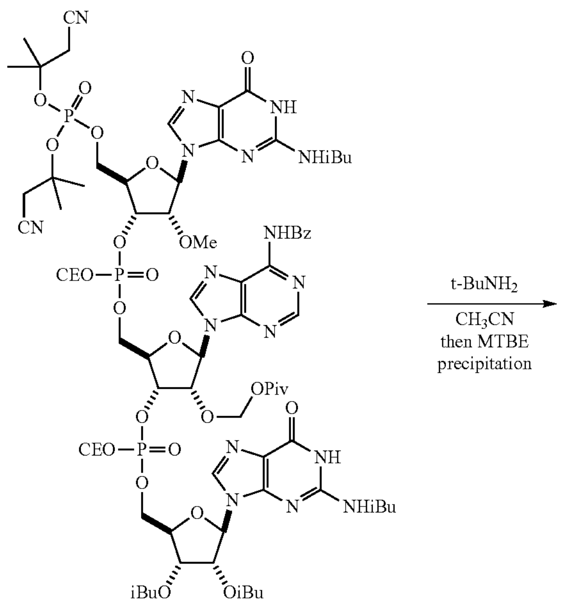

11s

-continued

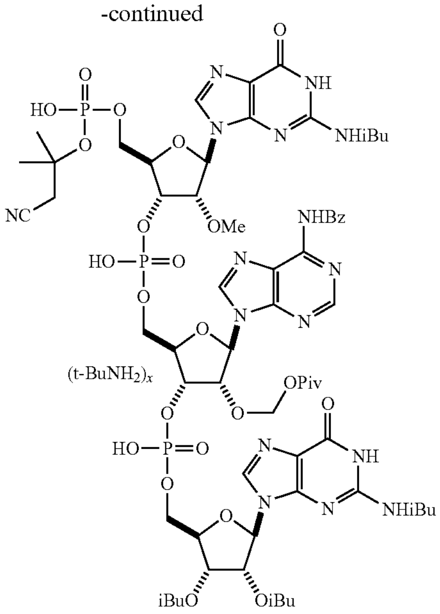

11s-1

11 s (1753 g; net 1122 g assumed, 617 mmol, 1 equiv.) was dissolved in acetonitrile (2.24 L, 2 vols) and treated with tert-Butylamine (1.12 L, 1 vol, 10.7 mol, 17 eq) at ambient temperature. The reaction was deemed complete in 15 min. A 20 L reactor was charged with MTBE (16.8 L, 15 vols) and cooled down. The reaction mixture was added to the pre-cooled MTBE under stirring (start: 7.8° C.; end 11° C.). The resultant light yellow suspension was stirred at 3° C. for 1 h and filtered through filter funnels. The supernatant was removed by peristaltic pump, and the wet solids on the filters were centrifuged. The packed solids were triturated with MTBE (5.6 L, 5 vols), centrifuged again, and dried in a vacuum oven (20° C.) for 3 days to give 11s-1 as an off-white solid (1221.7 g).

Stepwise Global Deprotection

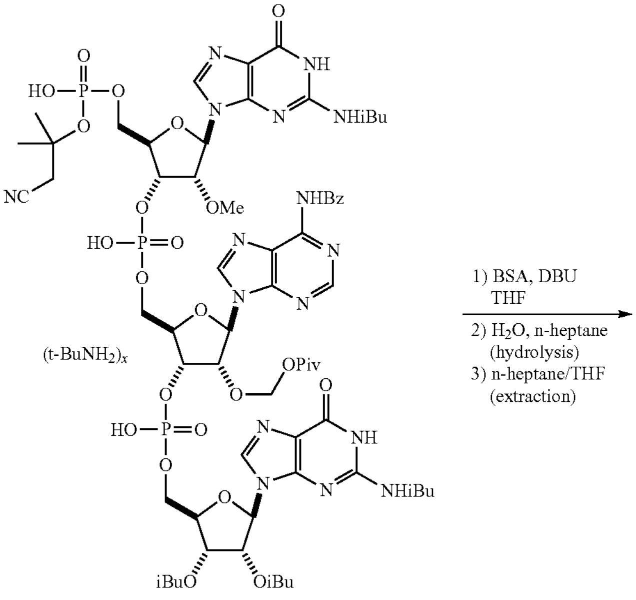

11s-1

-continued

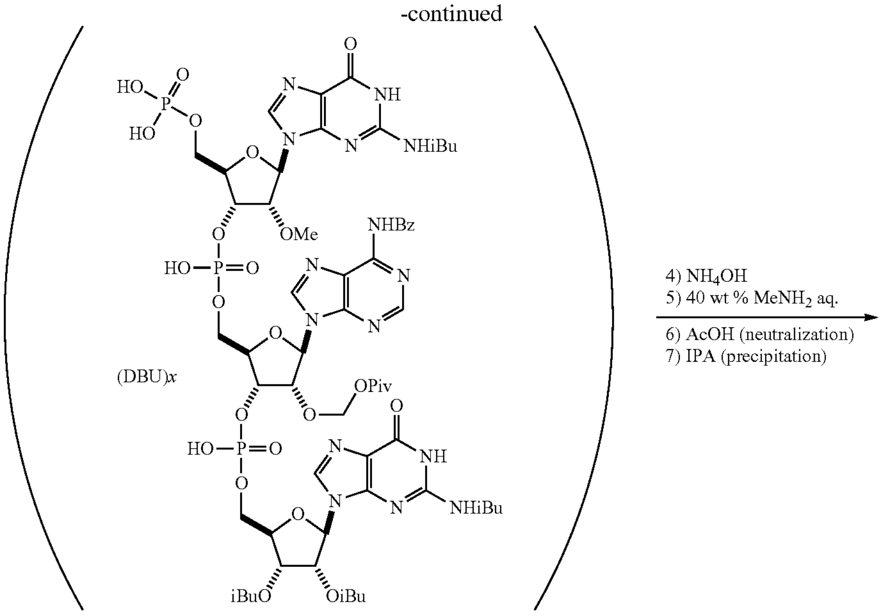

11s-2

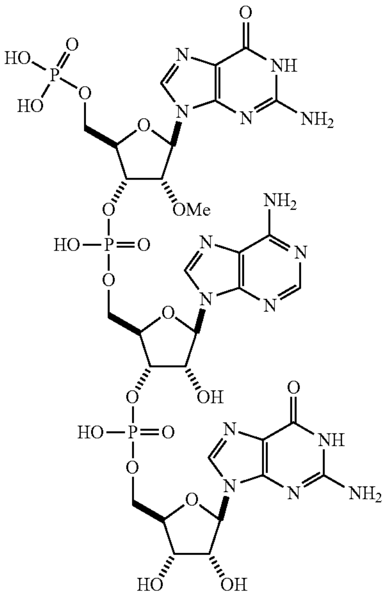

12s-1

11s-1 (405 g, 1 wt, 1 vol, 219 mmol, 1 eq) was dissolved in THF (1.62 L, 4 vols) and cooled down to below 0° C. BSA (867 mL, 2.14 vols, 3.55 mol, 16.2 eq) was added while maintaining T-internal below 0° C. (over 15 min). The mixture was allowed to warm up to 15° C. over 1 h and then cooled down to below 0° C. DBU (531 mL, 1.31 vols, 3.55 mol, 16.2 eq) was added dropwise while maintaining T-internal below 0° C. Upon complete addition, the mixture was allowed to warm up. IPC analysis (1 h, T-internal=12° C.) showed complete cleavage of the substituted cyanoethyl group. After an extra 0.5 h, the mixture (T-internal=17° C.) was cooled down to below 0° C. and diluted with n-heptane (3.24 L, 8 vols).

Under stirring, water (304 mL, 0.75 vols) was added while maintaining T-internal below 10° C. Stirring was continued, and the mixture was warmed up (18° C.). Stirring was stopped, and phase separation of the mixture was allowed. The upper solution was removed, and the thick aqueous mix of 11s-2 was washed twice with n-heptane-THF 2:1 (v/v) (2.43 L×2, 6 vols×2).

$NH_4OH$ (677 mL, 1.67 vols, 10 mol, 46 eq) was added, and the resultant mixture was stirred at ambient temperature overnight (16 h). 40% Methylamine (339 mL, 0.84 vol, 3.9 mol, 18 eq) was added, and stirring was continued. IPC samples were taken every 1-2 hours to monitor progress of the reaction. After 8 h (desired product:mono-iBu=93:7), the mixture was cooled down to below 0° C. and neutralized by dropwise addition of AcOH (1.065 L, 2.63 vols, 18.6 mol, 85 eq) while maintaining T-internal below 8° C.

After T-internal dropped back to below 0° C., IPA (6.48 L, 16 vols) was added to form a light yellow suspension. The mixture was transferred to 15× centrifuge bottles and subjected to centrifugation (3000 rpm, 4° C., 10 min). Supernatant was removed, and wet solids were stored in a refrigerator (5° C.) overnight. Trituration-centrifuge-decantation cycle was repeated with: (1) 70% EtOH-water and (2) EtOH, through which the solids were consolidated into fewer bottles. The wet solids in 4 bottles were dried in a vacuum oven overnight at 22° C. The solids were consolidated into 1 bottle (239 g solid) and dried further in a vacuum oven at 20° C. for 2 days to give 12s-1 as an off-white solid (184.2 g).

$Na^+$ Salt Formation, Reverse-Phase Purification, and Salt Exchange

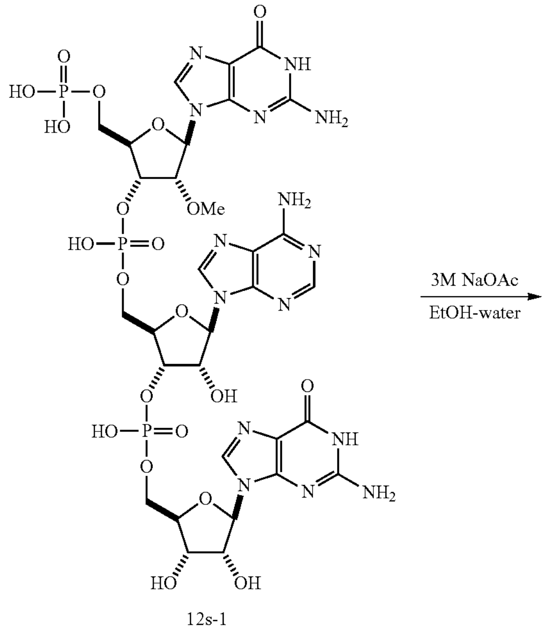

12s-1

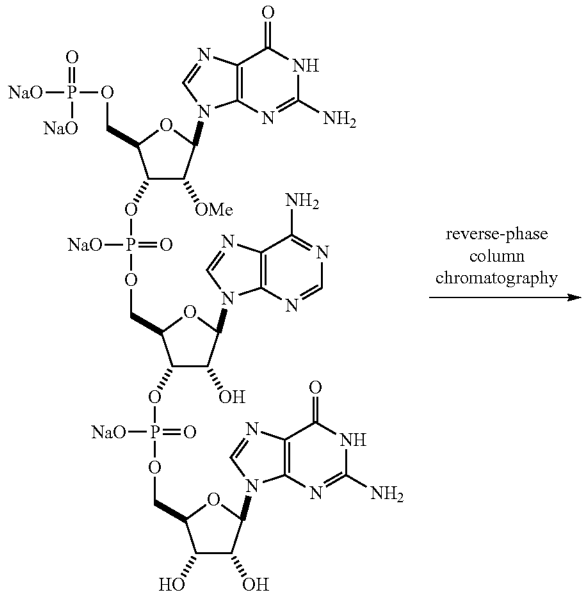

12s-2

-continued

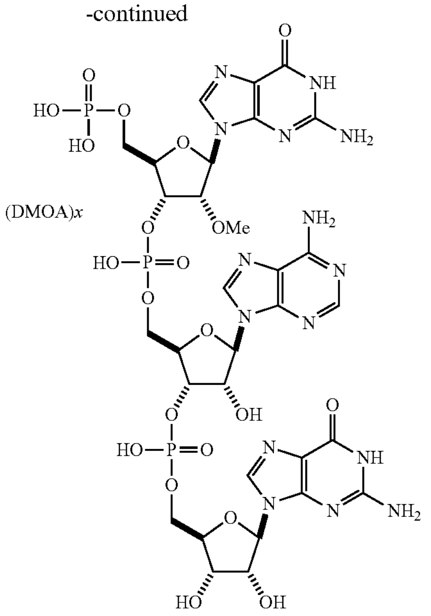

12s-3

12s-1 (368.4 g, 1 wt, 1 vol, 350 mmol, 1 eq; from two lots) was suspended in water (1.11 L, 3 vols), sonicated, and transferred into a 12-L RB flask. Water (368 mL, 1 vols) was used for complete rinse and transfer. 3M NaOAc aq. (0.70 L, 1.9 vols, 2.1 mol, 6 eq) was added under stirring (160 rpm). The mixture remained homogeneous. Absolute EtOH (6.63 L, 18 vols) was added. IPC analysis showed no product in yellow supernatant. The mixture was filtered through a Buchner glass funnel to collect off-white precipitates. The wet cake was rinsed with (1) EtOH—$H_2O$ 7:3 (v/v) (2.21 L, 6 vols) and (2) abs. EtOH (1.47 L, 4 vols) and dried in a vacuum oven at 22° C. for 3 days to give 12s-2 as an off-white solid (341 g, 0.92 wt, 299 mmol, 85% yield).

75 g of 12s-2 was purified by reverse phase chromatography using 2×800 g stacked PuriFlash Column, Atoll X 40μ 800 G polymer columns (CV=2243 mL: 16 CV were used, 36 L total solvent). The crude 12s-2 $Na^+$ salt was dissolved in 1.0 L water and 1.0 L of 400 mM Dimethyloctylammoniumbicarbonate (DMOAB) buffer solution. The resulting mixture was aged to allow for a full dissolution. The solution was filtered and loaded onto 2×800 g stacked PuriFlash Column, Atoll X 40p 800 G polymer columns. Mobile phase A: 10 mM DMOAB solution (prepared by mixing 125 mL of 400 mM stock solution of DMOAB in 5.0 L water), Mobile phase B: Acetonitrile. Mobile phase A (DMOAB buffer) was used to load the solution onto the column. The column was eluted with 0-25% B with a flow rate at 200 mL/min. Main peak fractions (~500 mL each) were collected and analyzed by UPLC/LCMS. Appropriate fractions were pooled and concentrated in vacuo to remove acetonitrile. The mixture was split into half (around 300 mL) into 2×500 mL bottles and lyophilized for 24-48 h to afford 12s-3 DMOA salt as white solid (39.3 g, 52% mass recovery, 95.6% pure).

Synthesis of 16 s
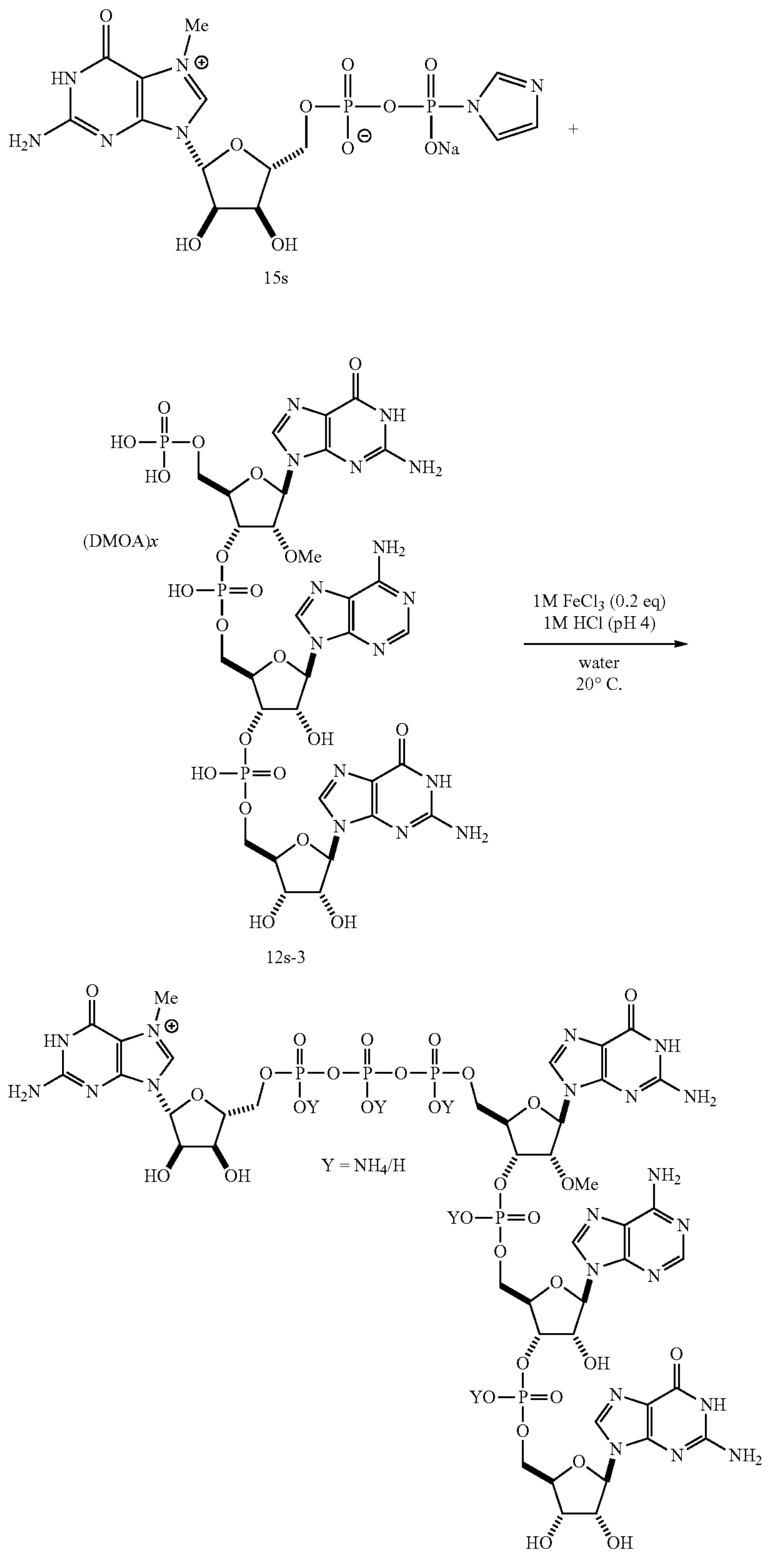
15s
12s-3
16s

A 2 L glass jacketed reactor was charged with 12s-3 DMOA salt (33.8 wt % DMOA, 96.8% pure; 102.01 g, 60 mmol) and water (0.30 kg). The mixture was stirred at 24-26° C. for complete dissolution, and then cooled down to 4° C. In a separate container, Im($m^7$GDP)Na* (15 s; 155.07 g) was dissolved in water (0.40 kg) and added to the reactor. Extra water (0.10 kg×2) was used for complete rinse and transfer. The mixture was cooled down to −1° C. (pH 7). 1N HCl (aqueous solution; 300 ml, 300 mmol) was added dropwise for adjustment to pH 5.0 (target 1±2° C.). 1M $FeCl_3$ (aqueous solution; 13 mL, 13 mmol) was added dropwise at 0° C. 1N HCl (aqueous solution; 50 ml, 50 mmol) was added dropwise for adjustment to pH 4.0 (target 1 t 2° C.). The mixture was warmed up to 20° C. and stirred for 16 h (95% conversion by HPLC). The mixture was cooled down (target 1 f 2° C.) and adjusted to pH 5.3 with 5 wt % $NH_4OH$ (12 mL). The mixture was collected from the reactor, polish-filtered, and purified by combination of anion-exchange chromatography ($NH_4Cl$ buffer) and tangential flow filtration (TFF) to give 16 s as a 20 mM aqueous solution of the ammonium ($NH_4$+) salt form (1.97 kg; net 55.5 g 16 s free phosphate, 62% adjusted yield). *Im ($m^7$GDP)Na: $P^2$-imidazolide 7-methylguanosine 5'-diphosphate, monosodium salt (CAS 531553-69-2).

Trinucleotide $Na^+$ Salt 12s-2 Alternate Preparation and Isolation

Preparation and Isolation 1: Trinucleotide DMOA salt 12s-3 (lyophilized solid; 3.00 g) was suspended in 6 mL water with gentle heating (45° C. bath). 3M NaOAc aq (6 ml) was added, and the resultant mixture was heated to 45° C. for complete dissolution. Abs. EtOH (30 ml) was added with heating/stirring. Upon complete addition, the mixture was stirred at 45° C. for 3 min, then cooled down to 17° C. Off-white precipitates were collected by filtration, rinsed with (1) EtOH-water 7:3 (v/v) 30 ml and (2) EtOH (24 mL), and dried under vacuum/air for 20 min, then in a vacuum oven (40° C.) for 1 h to give 12s-2 as white solid (2.397 g).

Preparation and Isolation 2: Trinucleotide DMOA salt 12s-3 (lyophilized solid; 27.4 g) was dissolved in 123 ml water (4.5 vols). Upon complete dissolution, 36 ml of 3M NaOAc was added (6 eq). The mixture remained homogeneous. The resultant mixture was filtered through a 20 um PE filter and added into 384 ml abs EtOH (14 vols) under 600 rpm stirring. 41 ml water (1.5 vols) was used for complete rinse and filtration. After stirring for 1 h at ambient temperature, the mixture was filtered through a 20-micron PE filter funnel to collect white precipitates, rinsed with: (1) 82 ml 70% EtOH (3 vols), (2) 82 ml 70% EtOH (3 vols), (3) 82 ml EtOH (3 vols), and (4) 82 ml EtOH (3 vols), dried under $N_2$/vacuum for 30 min, and transferred to an amber glass jar. Overnight drying in a vacuum oven at 35° C. gave 12s-2 as a white solid (21.52 g).

Preparation and Isolation 3: An aqueous solution of trinucleotide $Na^+$ salt 12s-2 (2372 g; est. net 25 g assumed, obtained from AEX and TFF purification of 12s-1) was concentrated down to 211 g, filtered through a filter funnel (20-micron PE frit), and added into 250 ml 2-propanol at ambient temperature to form a white slurry. 39 ml of water was used for complete rinse, filtration, and transfer. The mixture was diluted with an extra 250 ml 2-propanol, and white precipitates were collected by filtration, rinsed with (1) 100 ml 2-propanol and (2) 150 ml EtOH, and dried in a vacuum oven overnight (30° C.). 19.974 g white solid thus obtained was broken into fine powders by spatula and further dried in a vacuum oven at 30° C. 12s-2 was obtained as a white solid (19.045 g).

Preparation and Isolation 4: An aqueous solution of trinucleotide $Na^+$ salt 12s-2 (2340 g; net 25 g assumed, obtained from AEX and TFF purification of 12s-1) was concentrated down to 0.5 L and filtered through a filter funnel (20-micron PE frit). The collected filtrate was further concentrated down to 150 g and diluted with 350 ml 2-propanol in a 700 ml centrifuge bottle. 50 ml of water was used for complete rinse and transfer. The resultant white slurry was subjected to centrifuge-decantation-trituration cycle (3000 rpm, 10 min, 4° C.) with 150 ml 70% EtOH, followed by 150 mL EtOH. Wet white solid thus obtained was dried in a vacuum oven at 35° C. for 3 days to give 12s-2 as a white solid (16.88 g).

Trinucleotide 12 s $Li^+$ Salt Preparation

The crude trinucleotide 12s-1 (1 g, 1 vol) was dissolved in 2 ml of water (2 vols) and treated with 8 M LiCl (1 ml) at room temperature. After 3 min, 80% EtOH (v/v) was added, and off-white precipitates thus formed were collected by filtration, rinsed with (1) 80% EtOH (8 ml) and (2) absolute EtOH (8 ml), and then dried to give Trinucleotide 12 s $Li^+$ salt as an off-white solid (840 mg).

Trinucleotide 12 s $K^+$ Salt Preparation

Trinucleotide DMOA salt 12s-3 (42.38 g, 27.8 mmol, 1 equiv.) was dissolved in water (127 mL, 3 Vols). 3M KOAc (46.4 mL, 139 mmol, 5 equiv.) was added at ambient temperature, heated to 45° C., then cooled down. Absolute EtOH (0.51 L, 12 vols) was added, and the white suspension thus formed was transferred to a 2 L flask. Water (85 mL, 2 vols) and absolute EtOH (0.51 L, 12 Vols) were used for complete transfer and dilution. The next day, the white suspension was transferred to 2×700 ml centrifuge bottles and subjected to centrifuge-decantation-trituration cycles (3000 rpm for 10 min, 4° C.) with 70% EtOH (0.5 L/bottle) followed by abs. EtOH (0.5 L/bottle). The white wet cake thus obtained was dried in a vacuum oven (20° C.) for 3 days to give 12 s $K^+$ salt (27.3 g).

INCORPORATION BY REFERENCE

The present application refers to various issued patent, published patent applications, scientific journal articles, and other publications, all of which are incorporated herein by reference. The details of one or more embodiments of the invention are set forth herein. Other features, objects, and advantages of the invention will be apparent from the Detailed Description, the Figures, the Examples, and the Claims.

EQUIVALENTS AND SCOPE

In the articles such as "a," "an," and "the" may mean one or more than one unless indicated to the contrary or otherwise evident from the context. Embodiments or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the disclosure or aspects of the disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the embodiments. Because such embodiments are deemed to be known to one of ordinary skill in the art, they may be excluded even if the exclusion is not set forth explicitly herein. Any particular embodiment of the invention can be excluded from any embodiment, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended embodiments. Those of ordinary skill in the art will appreciate that various changes and modifications to this description may be made without departing from the spirit or scope of the present invention, as defined in the following claims.

Embodiments

Embodiments of the present disclosure include.

Embodiment 1. A method for synthesizing a trinucleotide comprising:

a) reacting a compound, or salt thereof, of formula (4) with a compound, or salt thereof, of formula (5):

(4)

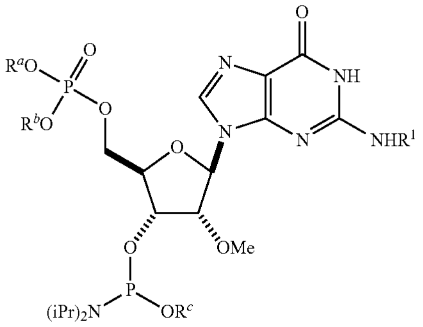

and (5)

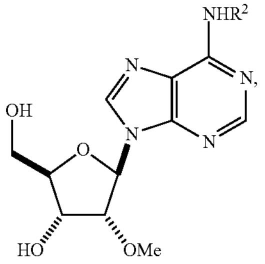

wherein each of $R^1$ and $R^2$ is independently a nitrogen protecting group; and $R^3$, $R^a$, $R^b$, and $R^c$ are each independently an oxygen protecting group;

to obtain a compound of formula (6):

(6)

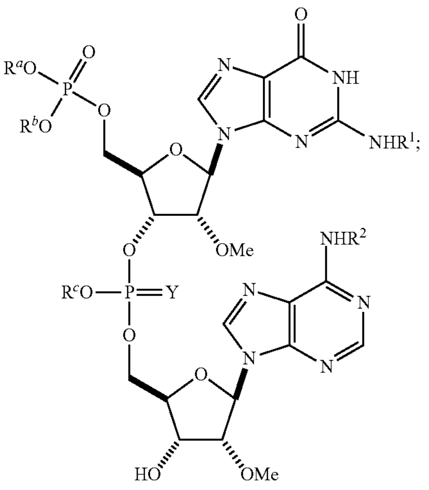

or a salt thereof;

wherein Y is O or is absent;

b) reacting the compound of formula (6) with a compound of formula (10):

(10)

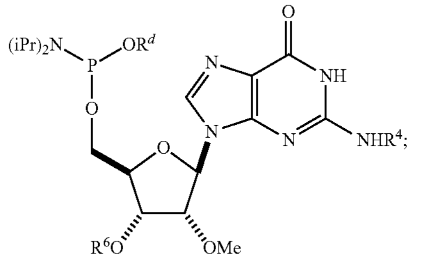

or a salt thereof;

wherein $R^4$ is a nitrogen protecting group; and $R^3$, $R^6$, and $R^d$ are each independently an oxygen protecting group;

to obtain a compound of formula (11):

(11)

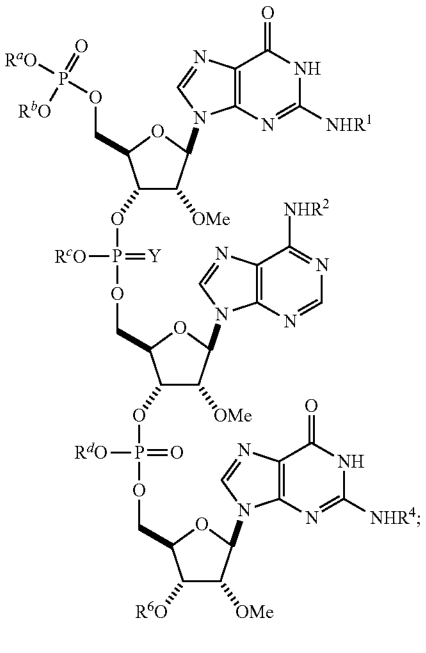

or a salt thereof.

Embodiment 2. The method of embodiment 1, wherein step a) and/or step b) further comprises adding an acid activator.

Embodiment 3. The method of embodiment 2, wherein the acid activator is a weak acid.

Embodiment 4. The method of embodiment 2 or 3, wherein the acid activator is selected from the group consisting of pyridine trifluoroacetate, 1H-tetrazole, diisopropylammonium tetrazolide, 5-(Ethylthio)-1H-tetrazole, and 4,5-dicyanoimidazole.

Embodiment 5. The method of embodiment 4, wherein the activator is pyridine trifluoroacetate.

Embodiment 6. The method of any one of embodiments 1-5, wherein step a) is carried out in the presence of a solvent selected from the group consisting of pyridine, acetonitrile, dichloromethane, tetrahydrofuran, and dimethylformamide.

Embodiment 7. The method of embodiment 6, wherein the solvent is pyridine.

Embodiment 8. The method of any one of embodiments 1-7, wherein step a) comprises a reaction time of approximately 2-3 hours.

Embodiment 9. The method of any one of embodiments 1-8, wherein step a) comprises a ratio of the compound of formula (5) to the compound of formula (4) of approximately 1:1.4.

Embodiment 10. The method of any one of embodiments 2-9, wherein step a) comprises a ratio of the compound of formula (5) to the acid activator of approximately 1:2.

Embodiment 11. The method of any one of embodiments 2-10, wherein step a) comprises a temperature of approximately −10° C. prior to adding the acid activator.

Embodiment 12. The method of any one of embodiments 2-11, wherein step a) comprises a temperature of approximately −3° C. to approximately 5° C. after adding the acid activator.

Embodiment 13. The method of any one of embodiments 1-12, wherein step a) does not comprise an oxidant, and wherein the compound of formula (6) is a compound of formula (6-a):

(6-a)

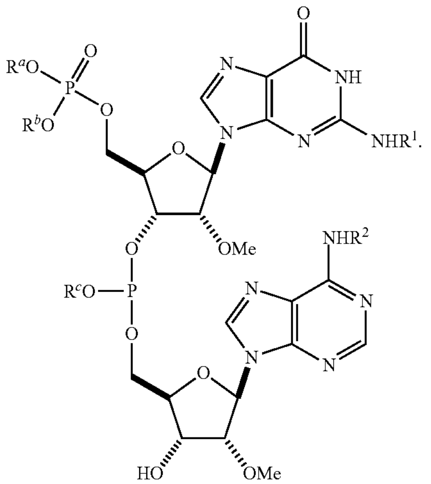

Embodiment 14. The method of embodiment 13, wherein the compound of formula (6-a) is not isolated prior to step b).

Embodiment 15. The method of any one of embodiments 1-12, wherein step a) comprises an oxidant, and wherein the compound of formula (6) is a compound of formula (6-b):

(6-b)

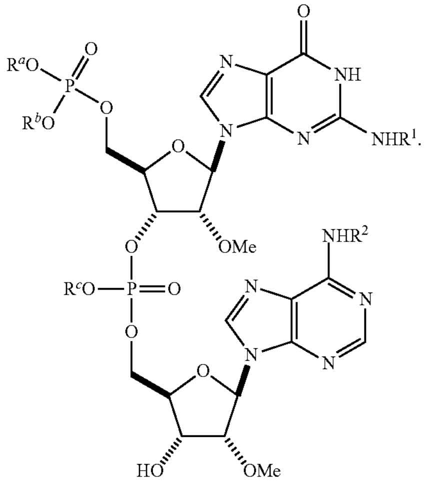

Embodiment 16. The method of embodiment 15, wherein the compound of formula (6-b) is isolated prior to step b).

Embodiment 17. The method of embodiment 13 or 14, wherein step b) comprises:

b.1) reacting the compound of formula (6-a) and the compound of formula (10) to obtain a compound of formula (11-a):

(11-a)

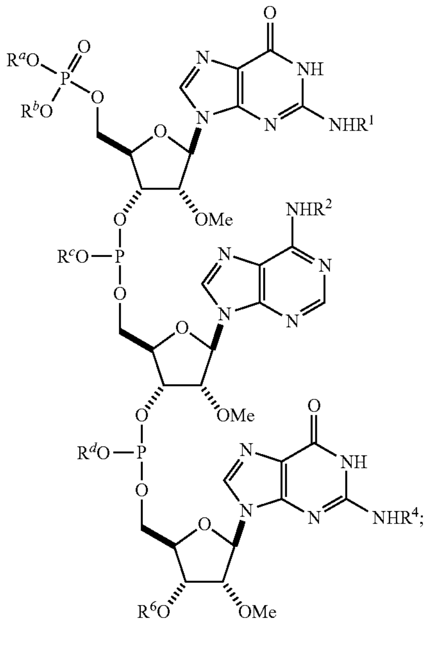

and b.2) oxidizing the compound of formula (11-a) to obtain the compound of formula (11).

Embodiment 18. The method of embodiment 17, wherein step b.1) comprises a reaction time of approximately 3 hours to approximately 4 hours.

Embodiment 19. The method of any one of embodiments 17-18, wherein step b.1) comprises a ratio of the compound of formula (6-a) to the compound of formula (10) of approximately 1:1.6.

Embodiment 20. The method of any one of embodiments 17-19, wherein step b.1) comprises a ratio of the compound of formula (6-a) to the acid activator of approximately 1:2.

Embodiment 21. The method of any one of embodiments 17-20, wherein step b.1) comprises a temperature of approximately 0° C. to approximately 14° C.

Embodiment 22. The method of embodiment 17, wherein step b.2) comprises an oxidant selected from the group consisting of a hydroperoxide, a peroxy acid, a diacyl peroxide, a dialkyl peroxide, hydrogen peroxide, oxygen gas, oxone, iodine and ozone.

Embodiment 23. The method of embodiment 22, wherein the oxidant is tert-butyl hydroperoxide.

Embodiment 24. The method of any one of embodiments 17-23, wherein step b.2) comprises a reaction time of approximately 12-24 hours.

Embodiment 25. The method of any one of embodiments 22-24, wherein step b.2) comprises a ratio of the compound of formula (6-a) to the oxidant of approximately 1:3.

Embodiment 26. The method of any one of embodiments 15-16, wherein step b) comprises reacting the compound of formula (6-b) and the compound of formula (10) to obtain a compound of formula (11).

Embodiment 27. The method of any one of embodiments 1-26, further comprising:

c) deprotecting the compound of formula (11) to form a compound of formula (12):

(12)

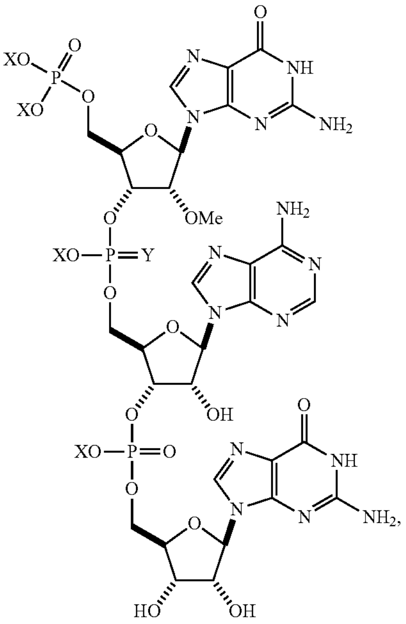

wherein X is absent H, Na, or DMOA;

or a salt thereof.

Embodiment 28. The method of embodiment 27, wherein step c) comprises;

c.1) deprotecting the phosphate moieties of the compound of formula (11) to obtain a compound of formula (12-a):

(12-a)

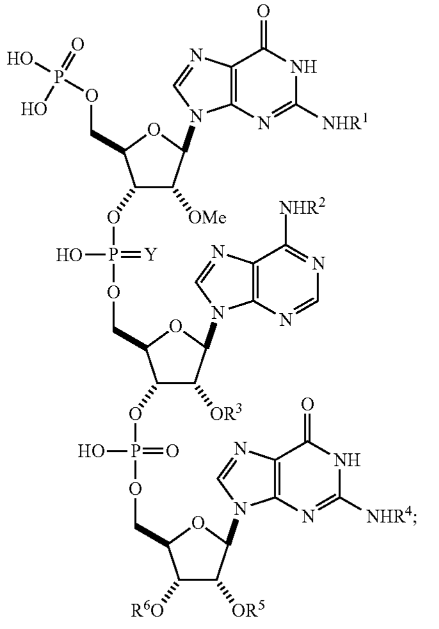

or a salt thereof; and c.2) global deprotection of the compound of formula (12-a) to obtain the compound of formula (12), or a salt thereof.

Embodiment 29. The method of embodiment 28, wherein step c.1) is carried out in the presence of N,O-Bis(trimethylsilyl)acetamide (BSA) and 1,8-diazabicyclo[5.4.0]undec-7-ene (DBU).

Embodiment 30. The method of embodiment 28 or 29, wherein step c.2) is carried out in the presence of ammonium hydroxide and methylamine.

Embodiment 31. The method of embodiment 27, wherein step c) comprises:

c.1) partially deprotecting the phosphate moieties of the compound of formula (11) to obtain a compound of formula (12-b):

(12-b)

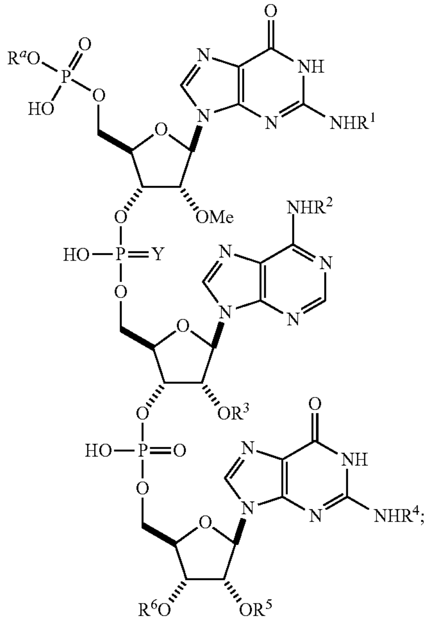

or a salt thereof;

c.2) deprotecting the remaining phosphate moiety of the compound of formula (12-b) to obtain a compound of formula (12-a).

(12-a)

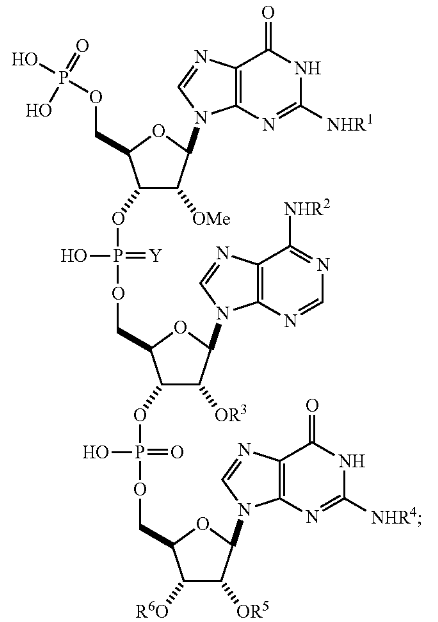

or a salt thereof; and c.3) global deprotection of the compound of formula (12-a) to obtain the compound of formula (12), or a salt thereof.

Embodiment 32. The method of embodiment 31, wherein step c.1) is carried out in the presence of t-$BuNH_2$.

Embodiment 33. The method of embodiment 31 or 32, wherein step c.2) is carried out in the presence of N,O-Bis (trimethylsilyl)acetamide (BSA) and 1,8-diazabicyclo [5.4.0]undec-7-ene (DBU).

Embodiment 34. The method of any one of embodiments 31-33, wherein step c.3) is carried out in the presence of ammonium hydroxide and methylamine.

Embodiment 35. The method of any one of embodiments 27-34, further comprising: d) reacting the compound of formula (12) with a compound of formula (15):

(15)

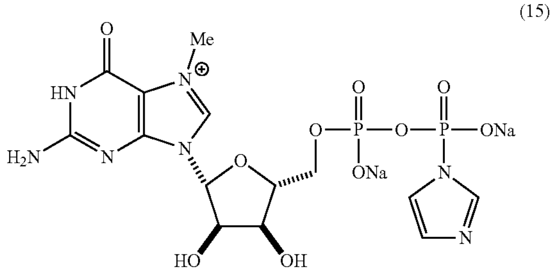

to obtain a compound of formula (16):

(16)

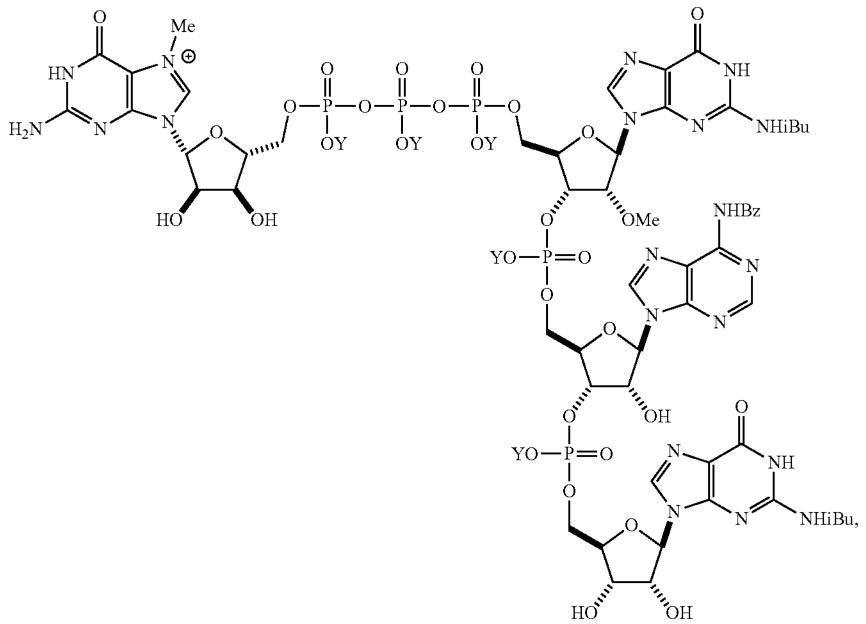

or a salt thereof;

wherein each instance of Y is independently $NH_4$ or absent.

Embodiment 36. The method of embodiment 35, further comprising, prior to reacting the compound of formula (12) with the compound of formula (15):

i) converting a compound of formula (12), wherein X is H, to a compound of formula (12), wherein X is Na, K, or Li; and ii) converting the compound of formula (12), wherein X is Na, K, or Li, to a compound of formula (12), wherein X is DMOA.

Embodiment 37. The method of embodiment 36, wherein the compound of formula (12), wherein X is DMOA, is used in the reaction with the compound of formula (15) to obtain a compound of formula (16).

Embodiment 38. The method of embodiment 35, wherein step d) comprises metal salt-mediated coupling of the compound of formula (12) and the compound of formula (15).

Embodiment 39. The method of embodiment 35 or 38, wherein step d) is carried out in the presence of HCl and a metal salt.

Embodiment 40. The method of any one of embodiments 35-39, wherein the compound of formula (16) is purified by tangential flow filtration (TFF).

Embodiment 41. The method of embodiment 40, wherein the compound of formula (16) is further purified by anion-exchange chromatography (AEX).

Embodiment 42. The method of any one of embodiments 1-41, wherein the compound of formula (4) is formed by:

e) phosphitylation of a compound of formula (3):

(3)

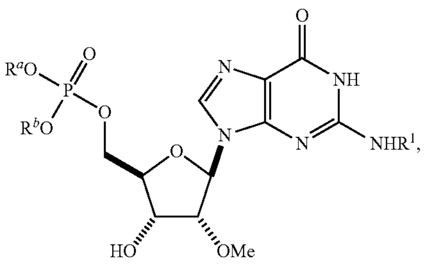

wherein $R^1$ is a nitrogen protecting group; and $R^a$ and $R^b$ are each independently an oxygen protecting group, to obtain the compound of formula (4).

Embodiment 43. The method of embodiment 42, wherein step e) is carried out in the presence of 2-cyanoethyl N,N,N',N'-tetraisopropylphosphorodiamidite and 5-(Ethylthio)-1H-tetrazole (ETT).

Embodiment 44. The method of embodiment 42, wherein the compound of formula (4) is not purified or worked up prior to reaction with the compound of formula (5).

Embodiment 45. The method of embodiment 42 or 43, wherein the compound of formula (3) is formed by:

f) reacting a compound of formula (1) with a compound of formula (2):

(1)

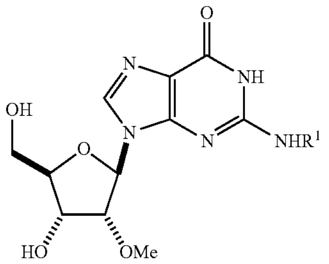

and (2)

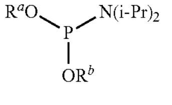

wherein $R^1$ is a nitrogen protecting group; and $R^a$ and $R^b$ are each independently an oxygen protecting group;

to obtain the compound of formula (3).

Embodiment 46. The method of embodiment 45, wherein step f) comprises:

f.1) reacting the compounds of formulae (1) and (2) in the presence of an acid activator; and f.2) oxidizing the product of step f.1).

Embodiment 47. The method of any one of embodiments 1-46, wherein each of $R^a$, $R^b$, $R^c$, and $R^d$ is independently of the formula:

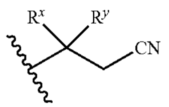

wherein each of $R^x$ and $R^y$ is independently H, optionally substituted cyclic or acyclic alkyl, optionally substituted cyclic or acyclic heteroalkyl, optionally substituted aryl, or optionally substituted heteroaryl; or wherein $R^x$ and $R^y$ are combined to form a 3-6 membered ring.

Embodiment 48. The method of embodiment 47, wherein each of $R^x$ and $R^y$ is independently H, or $C_1$-$C_6$ alkyl, or wherein $R^x$ and R are combined to form a 3-6 membered carbocycle.

Embodiment 49. The method of any one of embodiments 1-48, wherein $R^a$ and $R^b$ are of the formula:

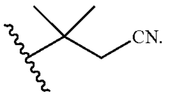 [SMILES: *C(C)(C)CC#N]

Embodiment 50. The method of any one of embodiments 1-49, wherein R is of the formula:

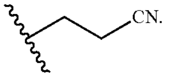 [SMILES: *CCC#N]

Embodiment 51. The method of any one of embodiments 1-50, wherein $R^{dd}$ is of the formula:

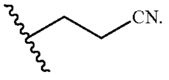 [SMILES: *CCC#N]

Embodiment 52. The method of embodiment 45, wherein the compound of formula (1) has the structure:

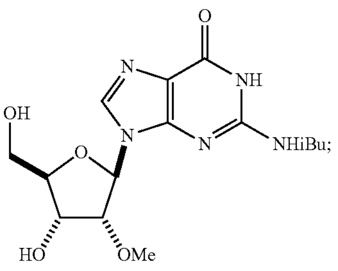

or a salt thereof.

Embodiment 53. The method of embodiment 45, wherein the compound of formula (2) has the structure:

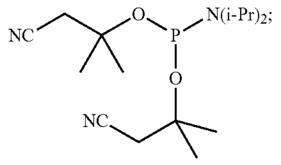

or a salt thereof.

Embodiment 54. The method of any one of embodiments 42-53, wherein the compound of formula (3) has the structure:

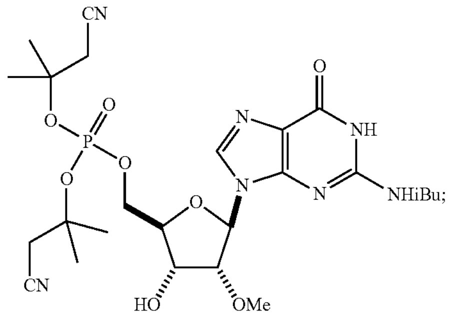

or a salt thereof.

Embodiment 55. The method of any one of embodiments 1-54, wherein the compound of formula (4) has the structure:

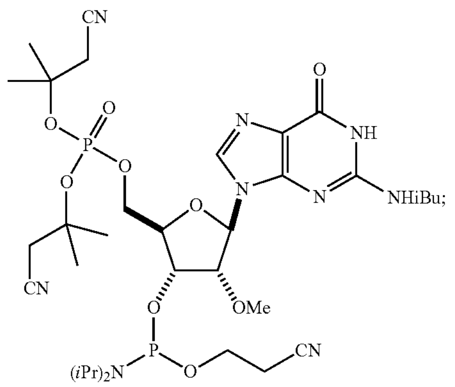

or a salt thereof.

Embodiment 56. The method of any one of embodiments 1-55, wherein the compound of formula (5) has the structure:

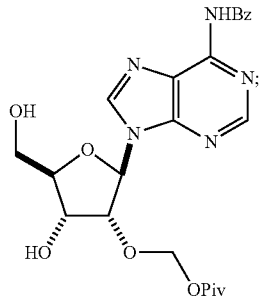

or a salt thereof.

Embodiment 57. The method of any one of embodiments 1-56, wherein the compound of formula (6) has the structure:

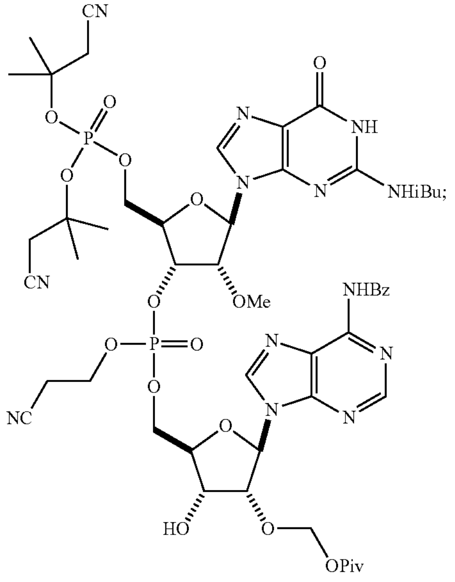

or a salt thereof.

Embodiment 58. The method of any one of embodiments 1-57, wherein the compound of formula (6) has the structure:

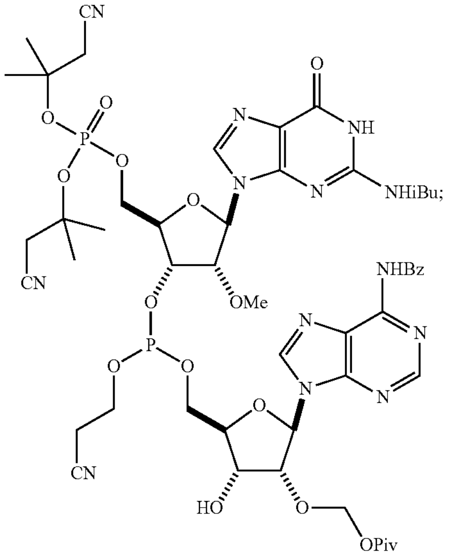

or a salt thereof.

Embodiment 59. The method of any one of embodiments 1-58, wherein the compound of formula (10) has the structure:

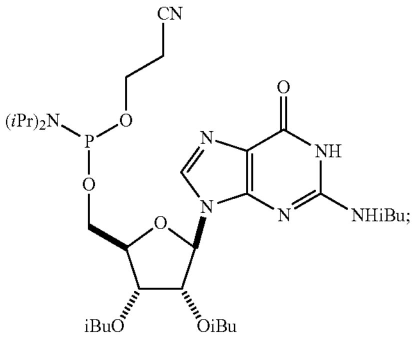

or a salt thereof.

Embodiment 60. The method of any one of embodiments 1-59, wherein the compound of formula (11) has the structure:

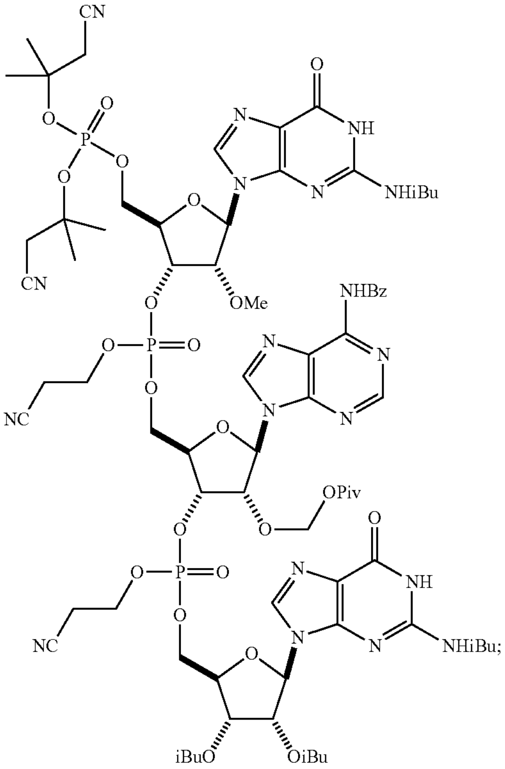

or a salt thereof.

Embodiment 61. The method of any one of embodiments 17-25, wherein the compound of formula (11-a) has the structure:

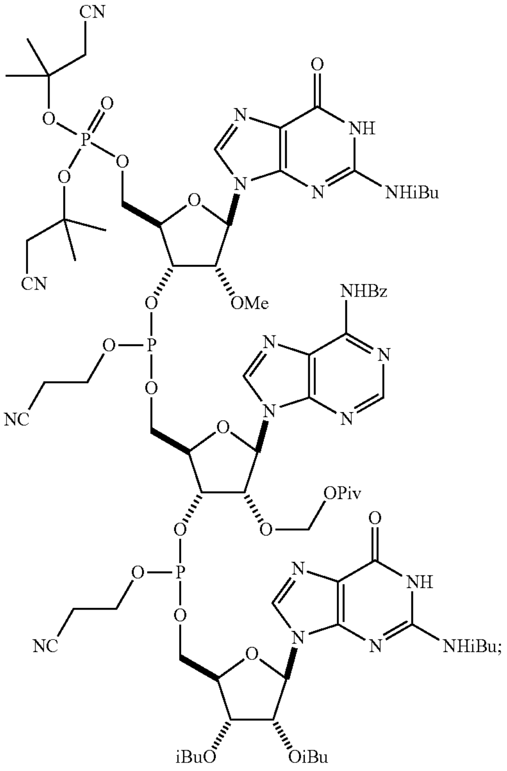
or a salt thereof.
Embodiment 62. The method of embodiment 31, wherein the compound of formula (12-a) has the structure:
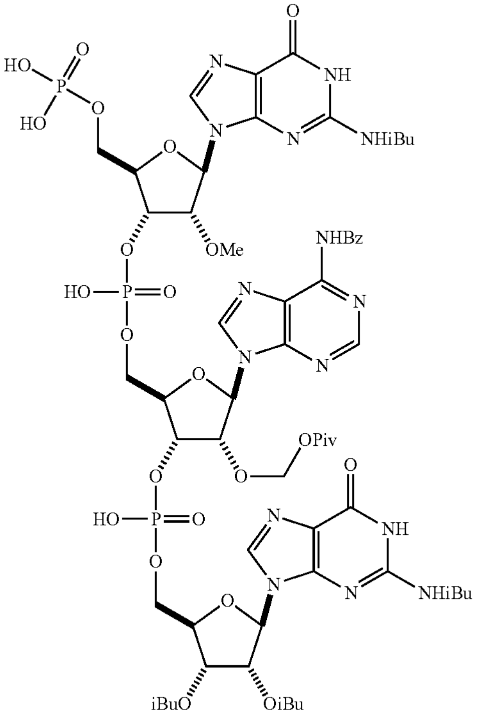
,
or a salt thereof.
Embodiment 63. The method of embodiment 31, wherein the compound of formula (12-b) has the structure:
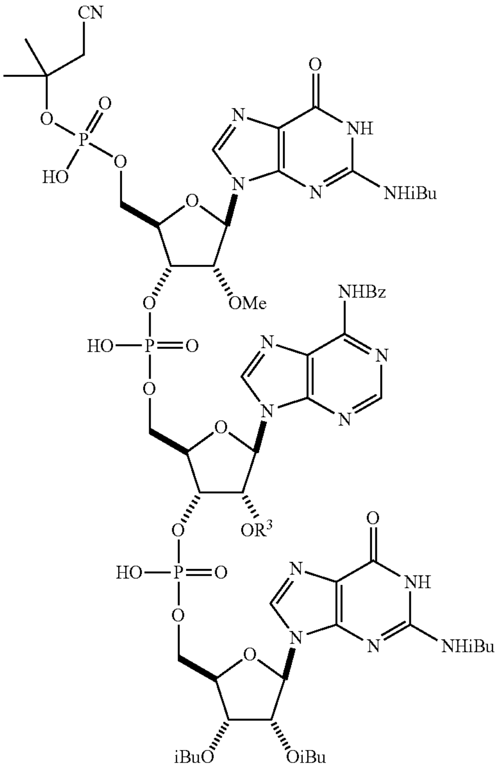
,
or a salt thereof.
Embodiment 64. A method for synthesizing a trinucleotide comprising:
a) reacting a compound of formula (4) with a compound of formula (5):
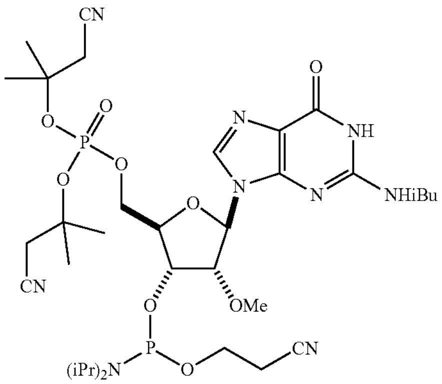
and -continued
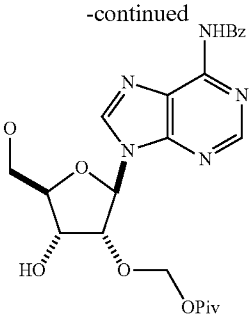
,
in the presence of pyridine trifluoroacetate and pyridine to obtain a compound of formula (6):
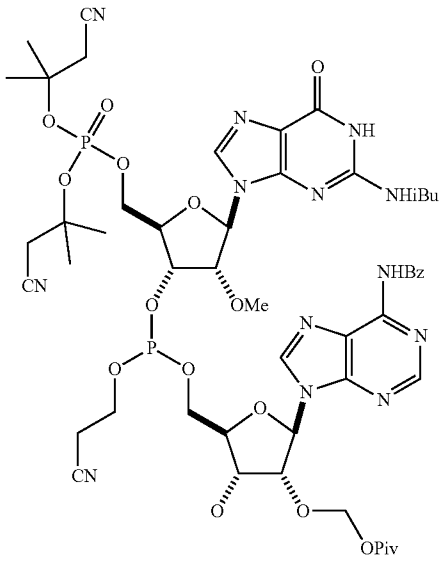
;
b.1) reacting the compound of formula (6) with a compound of formula (10):
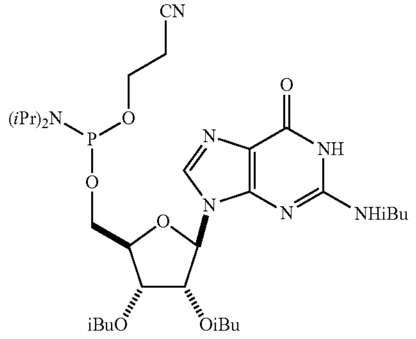
,
in the presence of pyridine trifluoroacetate and pyridine; to obtain a compound of formula (11-a):
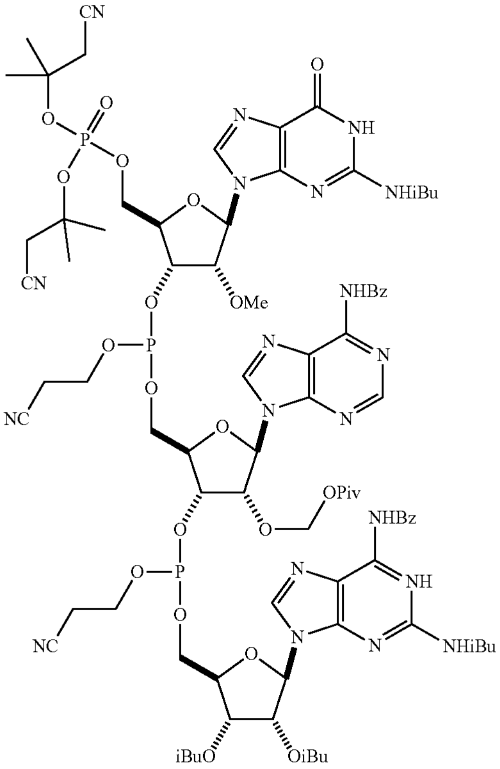
;

b.2) reacting the compound of formula (11-a) with tert-butyl hydroperoxide to obtain a compound of formula (11):
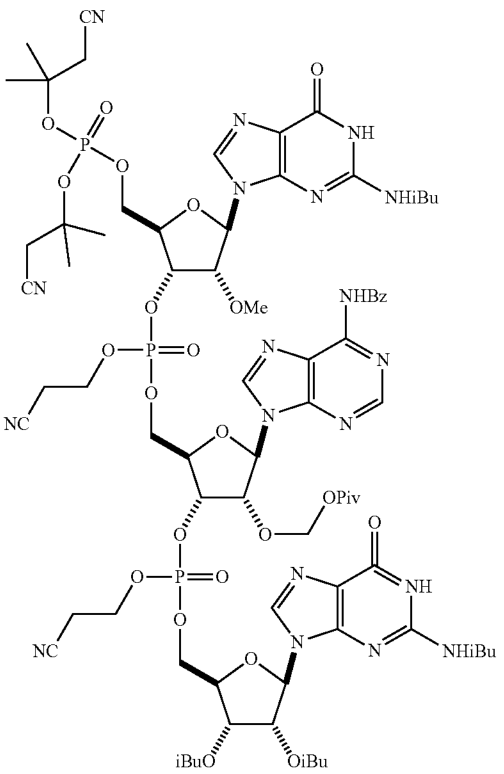
.
Embodiment 65. The method of embodiment 64, further comprising:
c.1) partially deprotecting the phosphate moieties of the compound of formula (11) in the presence of t-Bu$NH_2$ to obtain a compound of formula (12-b):
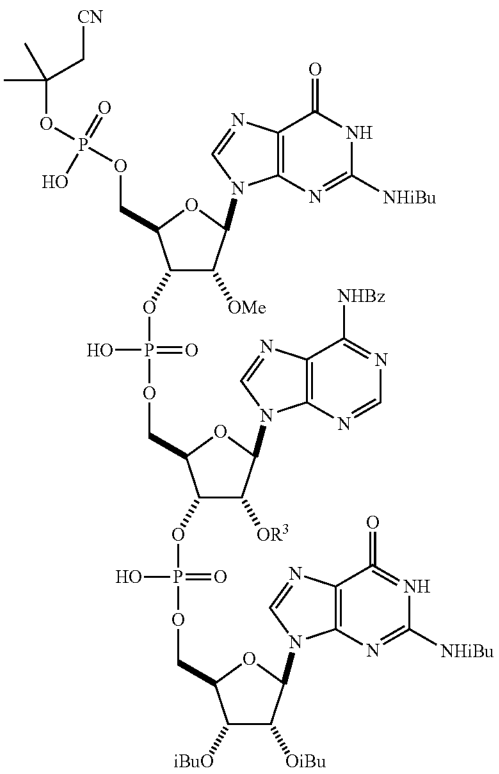
;

c.2) deprotecting the remaining phosphate moiety of the compound of formula (12-b) in the presence of N,O-Bis(trimethylsilyl)acetamide (BSA) and 1,8-diazabicyclo[5.4.0]undec-7-ene (DBU) to obtain a compound of formula (12-a):

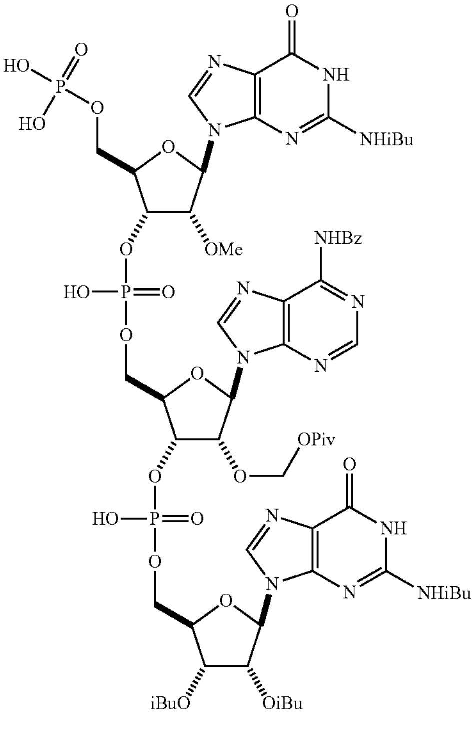

; and c.3) global deprotection of the compound of formula (12-a) in the presence of ammonium hydroxide and methylamine to obtain the compound of formula (12):

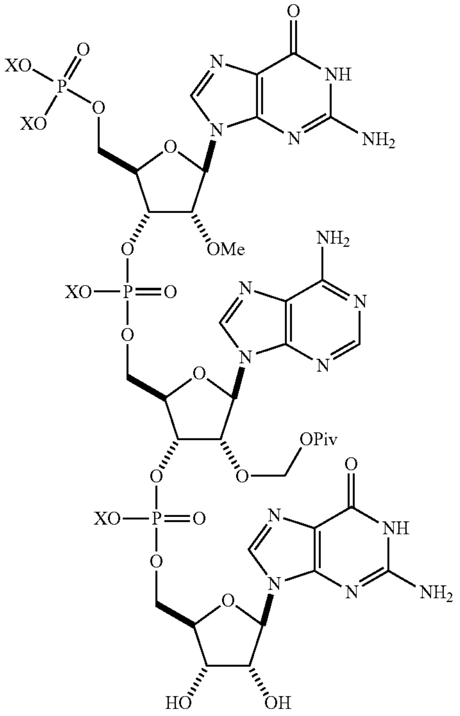

, wherein X is DMOA.

Embodiment 66. The method of embodiment 65, further comprising:

d) reacting the compound of formula (12) with a compound of formula (15):

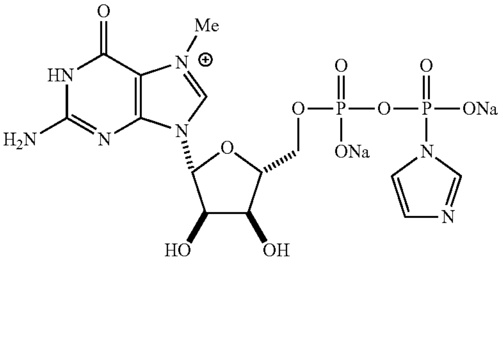

in the presence of HCl and a metal salt to obtain a compound of formula (16):

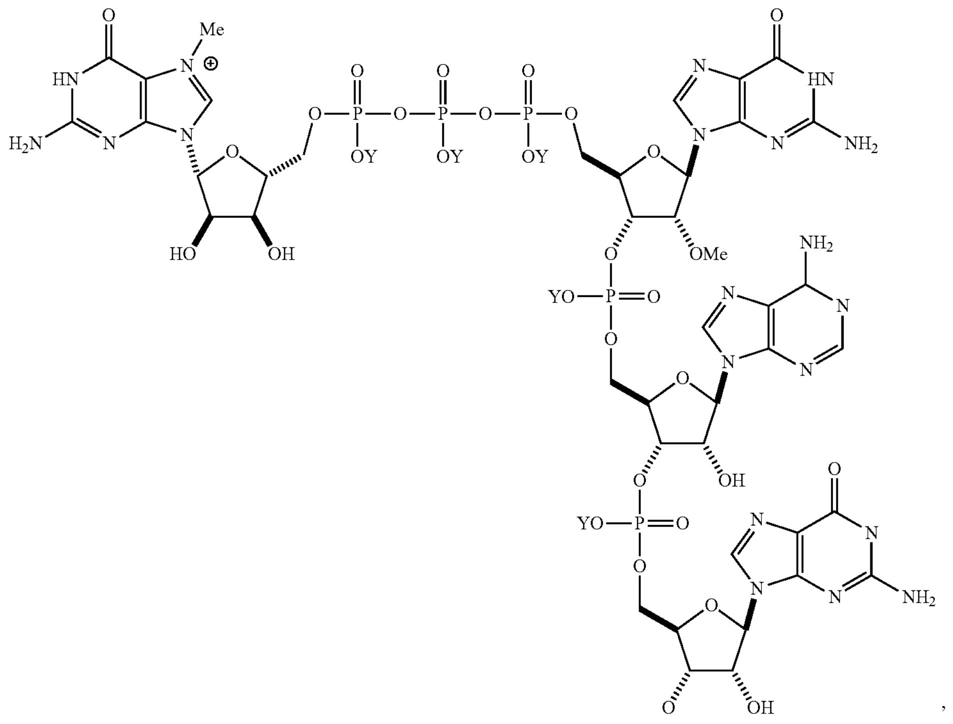

, wherein each instance of Y is independently $NH_4$ or absent.

Embodiment 67. The method of any one of embodiments 64-66, wherein the compound of formula (4) is formed by:

e) phosphitylation of a compound of formula (3):

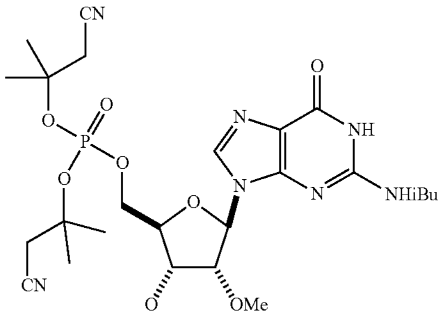

in the presence of 2-cyanoethyl N,N,N',N'-tetraisopropylphosphorodiamidite and 5-(Ethylthio)-1H-tetrazole (ETT) to obtain the compound of formula (4).

Embodiment 68. The method of embodiment 67, wherein the compound of formula (3) is formed by:

f.1) reacting a compound of formula (1) with a compound of formula (2) in the presence of pyridine trifluoroacetate and pyridine:

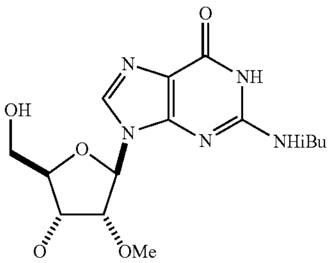

and

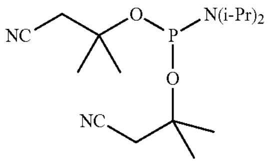

;

and f.2) oxidizing the product of step (f.1) in the presence of tert-butyl hydrogen peroxide to obtain the compound of formula (3).

Embodiment 69. A compound of formula (1) having the structure:

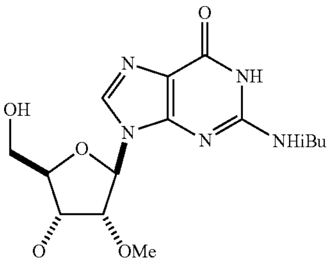

;

or a salt thereof.

Embodiment 70. A compound of formula (2) having the structure:

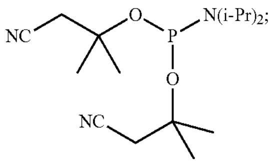

or a salt thereof.

Embodiment 71. A compound of formula (3) having the structure:

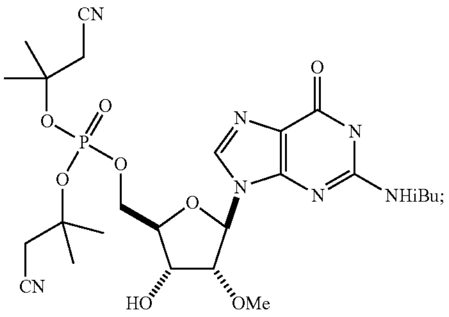

or a salt thereof.

Embodiment 72. A compound of formula (4) having the structure:

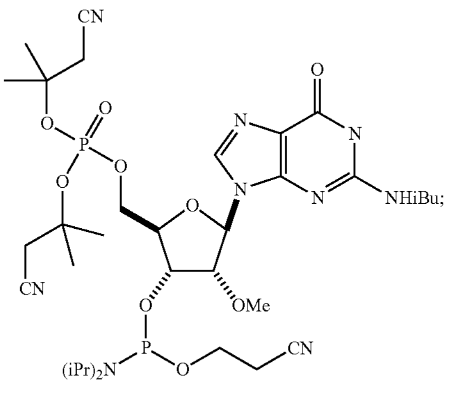

or a salt thereof.

Embodiment 73. A compound of formula (5) having the structure:

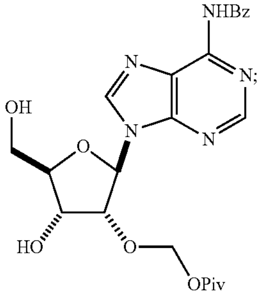

or a salt thereof.

Embodiment 74. A compound of formula (6) having the structure:

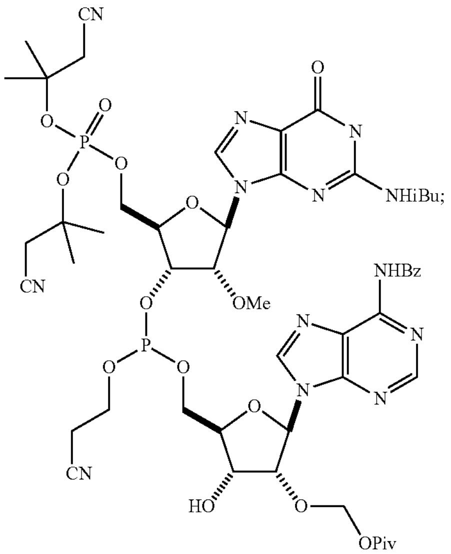

or a salt thereof.

Embodiment 75. A compound of formula (7) having the structure:

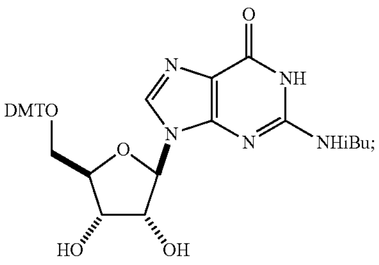

or a salt thereof.

Embodiment 76. A compound of formula (8) having the structure:

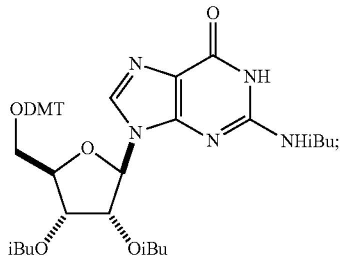

or a salt thereof.

Embodiment 77. A compound of formula (9) having the structure:

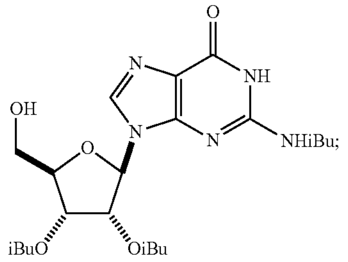

or a salt thereof.

Embodiment 78. A compound of formula (10) having the structure:

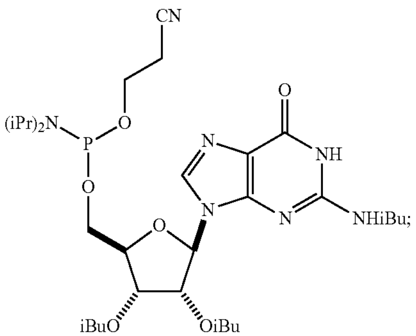

or a salt thereof.

Embodiment 79. A compound of formula (11) having the structure:

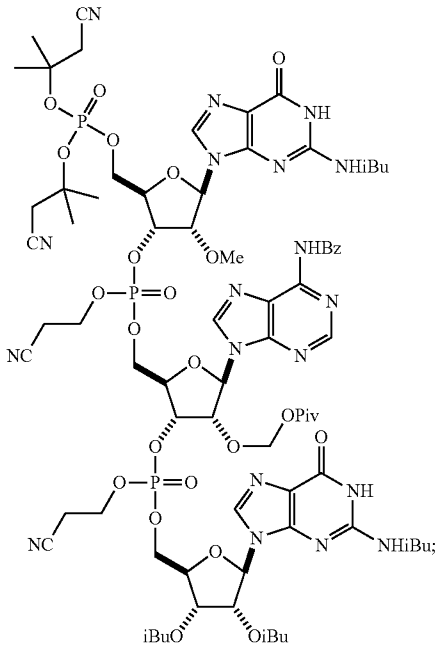

or a salt thereof.

Embodiment 79. A compound of formula (11-a) having the structure:

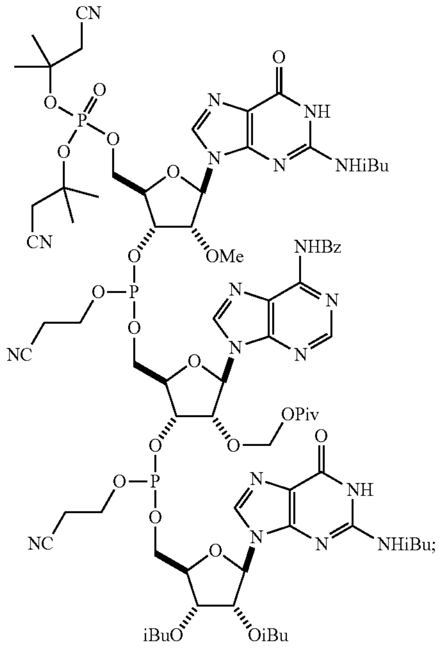

or a salt thereof.

Embodiment 81. A compound of formula (12-a) having the structure:
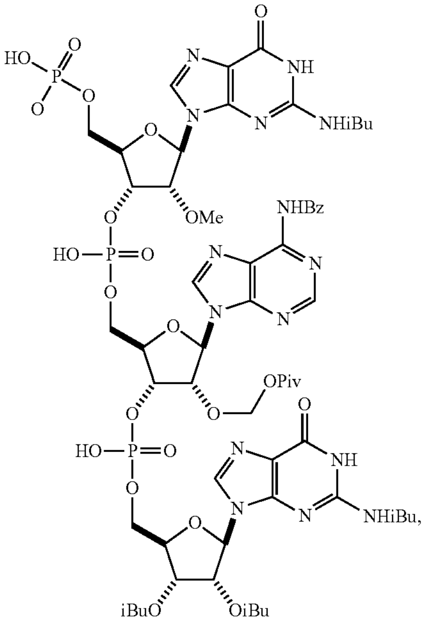
or a salt thereof.
Embodiment 82. A compound of formula (12-b) having the structure:
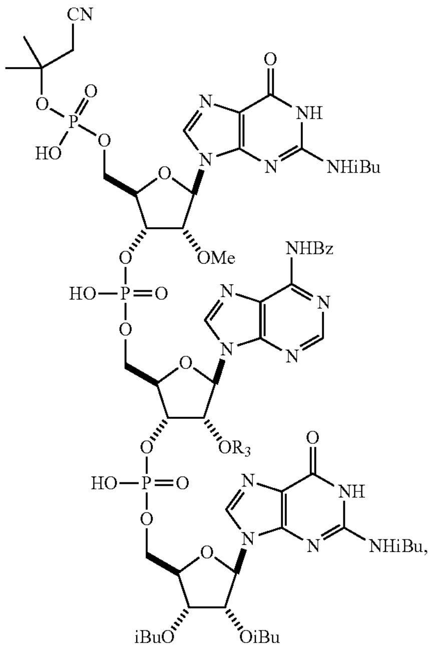
or a salt thereof.
Embodiment 83. A compound of formula (15) having the structure:
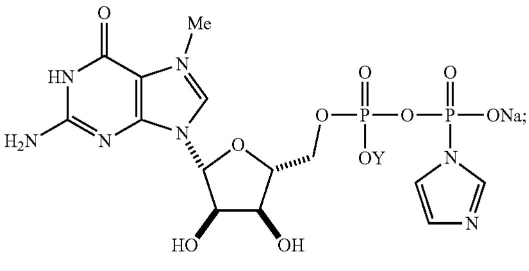
or a salt thereof.

Embodiment 84. A compound of formula (16) having the structure:

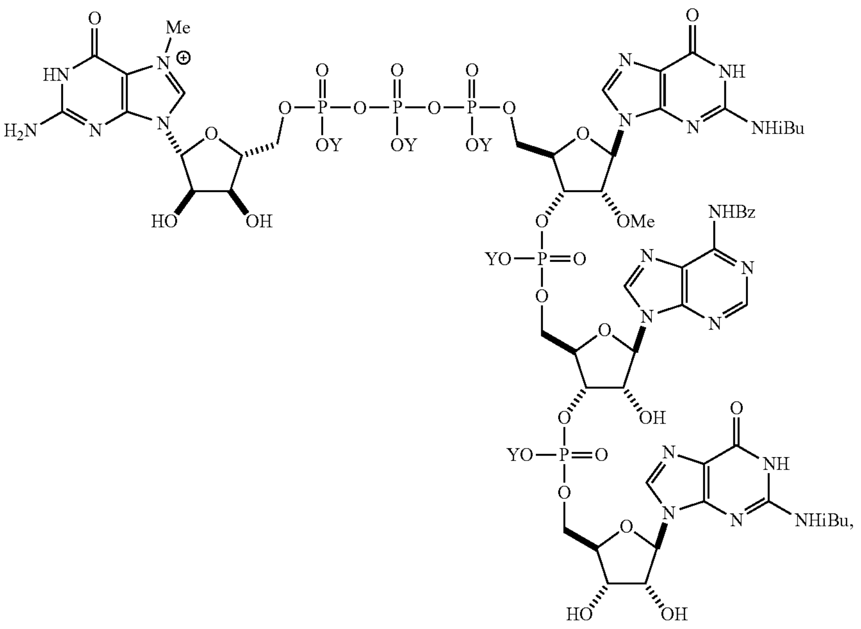

wherein each instance of Y is independently NH or absent;

or a salt thereof.

What is claimed is:

1. A method for synthesizing a trinucleotide comprising:

a) reacting a compound, or salt thereof, of formula (4) with a compound, or salt thereof, of formula (4)

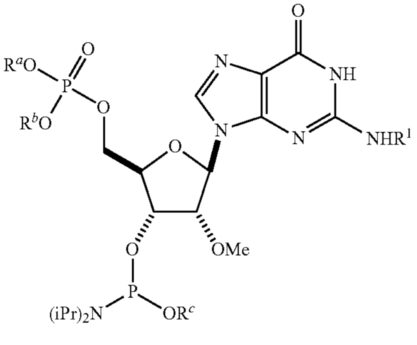

and (5)

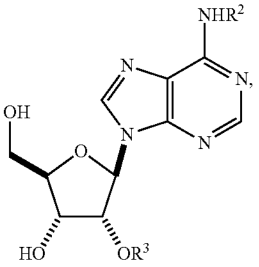

wherein each of $R^1$ and $R^2$ is independently a nitrogen protecting group; and $R^3$, $R^a$, $R^b$, and $R^c$ are each independently an oxygen protecting group;

to obtain a compound of formula (6):

(6)

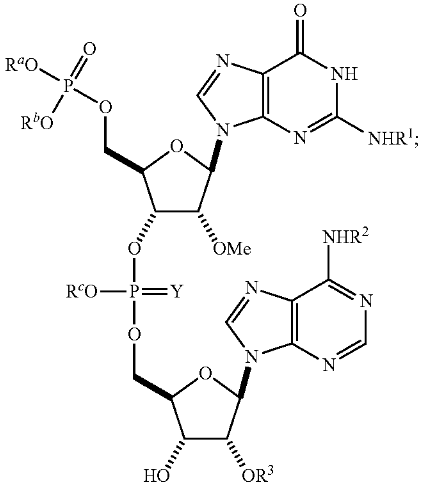

or a salt thereof;

wherein Y is O or is absent;

b) reacting the compound of formula (6) with a compound of formula (10):

(10)

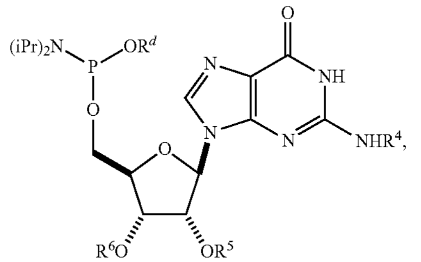

or a salt thereof;

wherein $R^4$ is a nitrogen protecting group; and $R^5$, $R^6$, and Rd are each independently an oxygen protecting group;

to obtain a compound of formula (11):

(11)

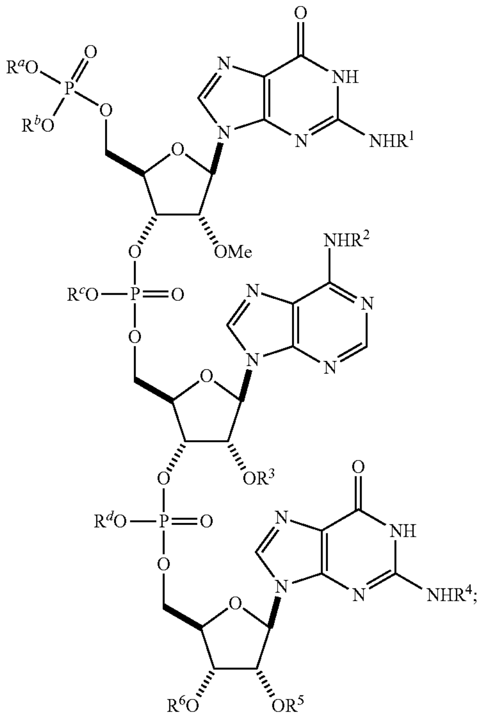

or a salt thereof.

2. The method of claim 1, wherein step a) and/or step b) further comprises adding an acid activator.

3. The method of claim 2, wherein the acid activator is selected from the group consisting of pyridine trifluoroacetate, 1H-tetrazole, diisopropylammonium tetrazolide, 5-(Ethylthio)-1H-tetrazole, and 4,5-dicyanoimidazole.

4. The method of claim 1, wherein step a) is carried out in the presence of a solvent selected from the group consisting of pyridine, acetonitrile, dichloromethane, tetrahydrofuran, and dimethylformamide.

5. The method of claim 1, wherein step a) does not comprise an oxidant, and wherein the compound of formula (6) is a compound of formula (6-a):

(6-a)

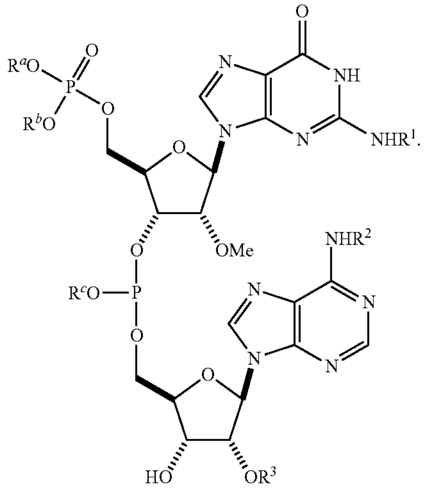

6. The method of claim 5, wherein the compound of formula (6-a) is not isolated prior to step b).

7. The method of claim 1, wherein step a) comprises an oxidant, and wherein the compound of formula (6) is a compound of formula (6-b):

(6-b)

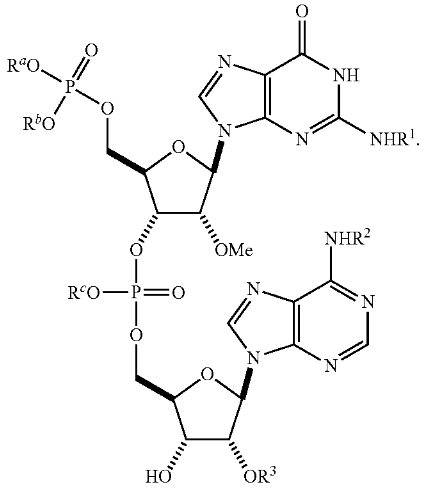

8. The method of claim 7, wherein the compound of formula (6-b) is isolated prior to step b).

9. The method of claim 5, wherein step b) comprises:

b.1) reacting the compound of formula (6-a) and the compound of formula (10) to obtain a compound of formula (11-a):

(11-a)

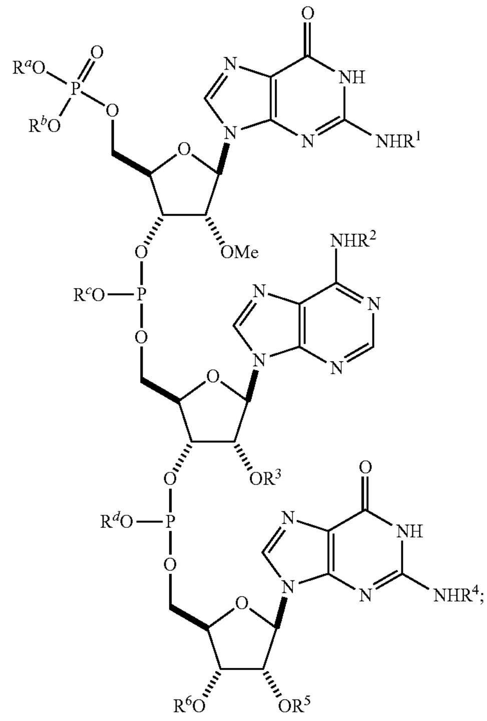

and b.2) oxidizing the compound of formula (11-a) to obtain the compound of formula (11).

10. The method of claim 9, wherein step b.2) comprises an oxidant selected from the group consisting of a hydroperoxide, a peroxy acid, a diacyl peroxide, a dialkyl peroxide, hydrogen peroxide, oxygen gas, oxone, iodine, and ozone.

11. The method of claim 7, wherein step b) comprises reacting the compound of formula (6-b) and the compound of formula (10) to obtain a compound of formula (11).

12. The method of claim 1, further comprising:

c) deprotecting the compound of formula (11) to form a compound of formula (12):

(12)

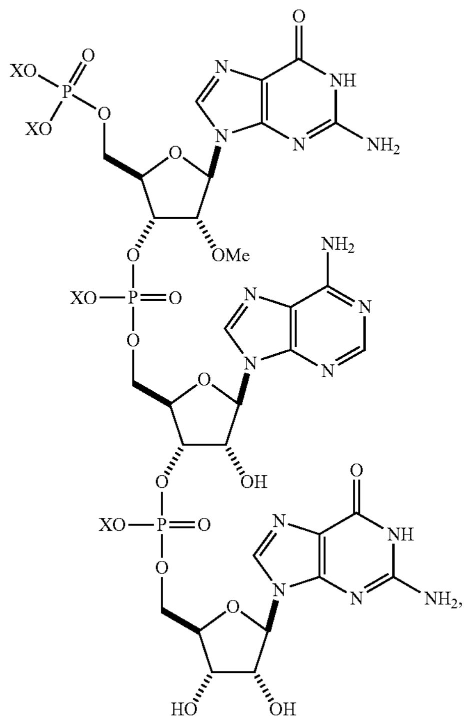

wherein X is absent, H, $Li^+$, $Na^+$, $K^+$, or DMOA; or a salt thereof.

13. The method of claim 12, wherein step c) comprises:

c.1) deprotecting the phosphate moieties of the compound of formula (11) to obtain a compound of formula (12-a):

(12-a)

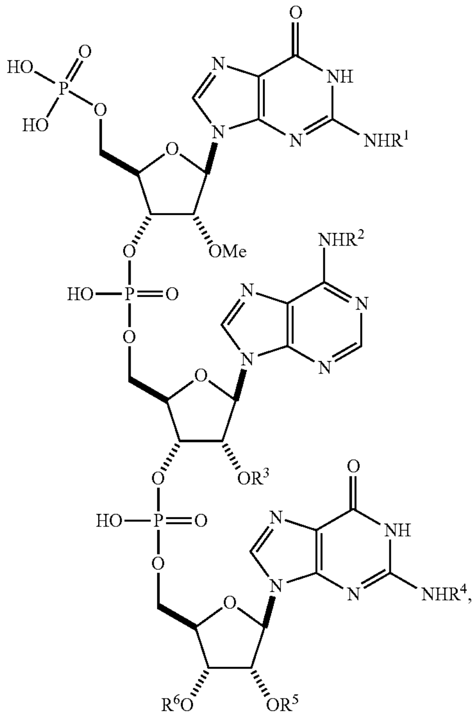

or a salt thereof; and c.2) global deprotection of the compound of formula (12-a) to obtain the compound of formula (12), or a salt thereof.

14. The method of claim 12, wherein step c) comprises:

c.1) partially deprotecting the phosphate moieties of the compound of formula (11) to obtain a compound of formula (12-b):

(12-b)

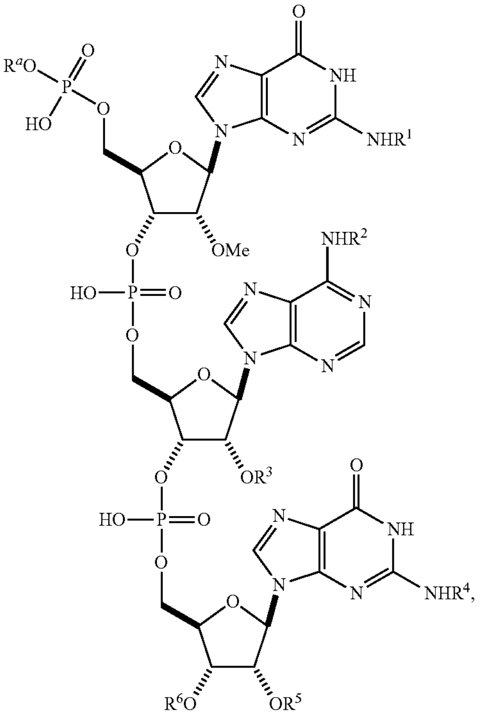

or a salt thereof;

c.2) deprotecting the remaining phosphate moiety of the compound of formula (12-b) to obtain a compound of formula (12-a):

(12-a)

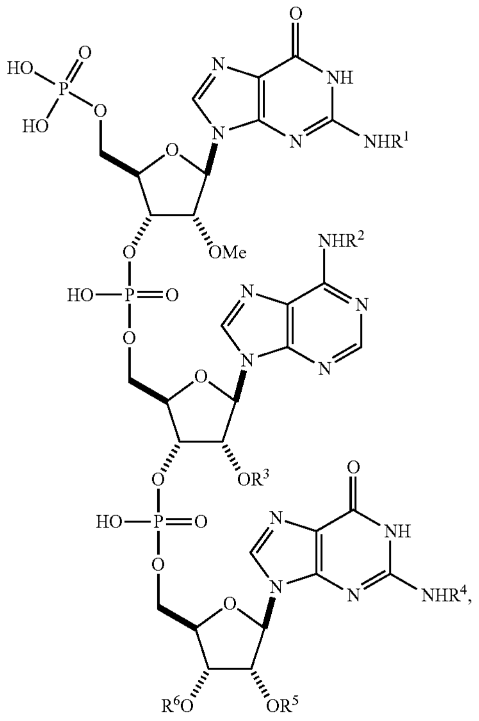

or a salt thereof; and c.3) global deprotection of the compound of formula (12-a) to obtain the compound of formula (12), or a salt thereof.

15. The method of claim 12, further comprising:

d) reacting the compound of formula (12) with a compound of formula (15):

(15)

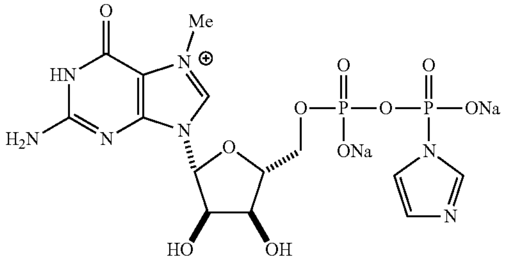

to obtain a compound of formula (16):

(16)

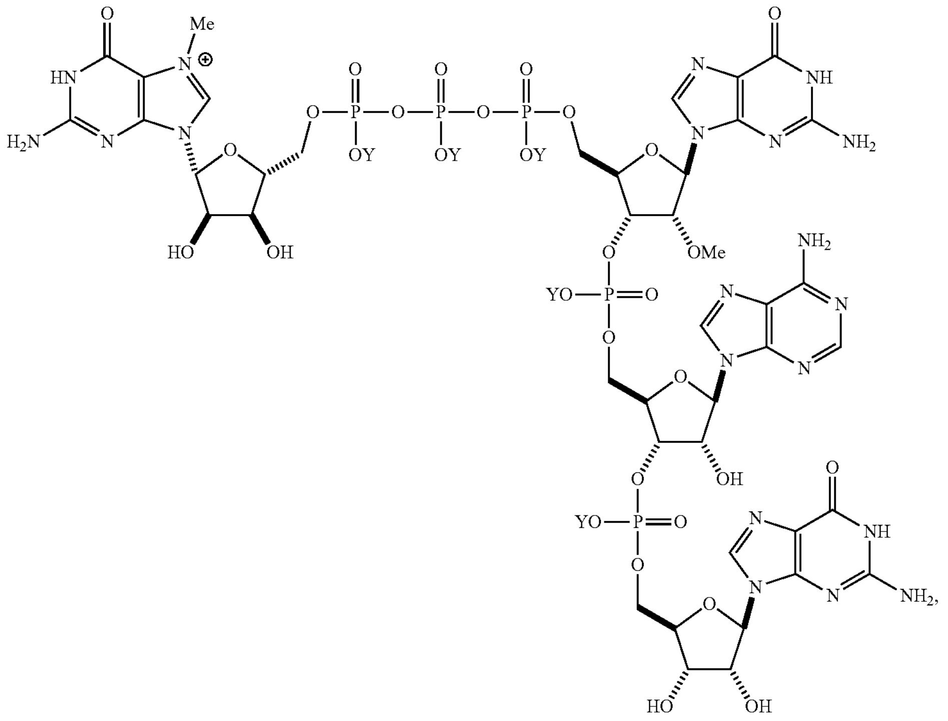

or a salt thereof;

wherein each instance of Y is independently $NH_4^+$ or absent.

16. The method of claim 1, wherein the compound of formula (4) is formed by:

e) phosphitylation of a compound of formula (3):

(3)

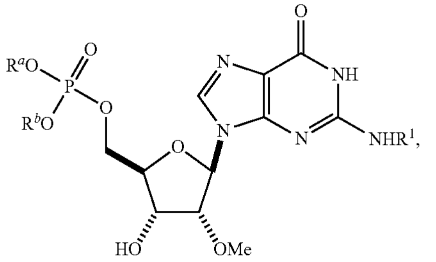

wherein $R^1$ is a nitrogen protecting group; and $R^a$ and $R^b$ are each independently an oxygen protecting group;

to obtain the compound of formula (4).

17. The method of claim 16, wherein the compound of formula (3) is formed by:

f) reacting a compound of formula (1) with a compound of formula (2):

(1)

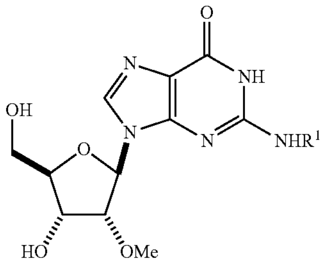

and (2)

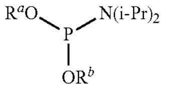

wherein $R^1$ is a nitrogen protecting group; and $R^a$ and $R^b$ are each independently an oxygen protecting group;

to obtain the compound of formula (3).

18. The method of claim 1, wherein each of $R^a$, $R^b$, $R^c$, and Rd is independently of the formula:

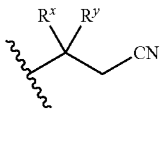

wherein each of $R^x$ and $R^y$ is independently H, optionally substituted cyclic or acyclic alkyl, optionally substituted cyclic or acyclic heteroalkyl, optionally substituted aryl, or optionally substituted heteroaryl; or wherein $R^x$ and $R^y$ are combined to form a 3-6 membered ring.

19. A method for synthesizing a trinucleotide comprising:

a) reacting a compound of formula (4) with a compound of formula (5):

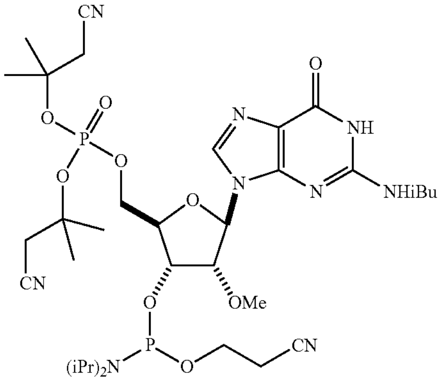

and

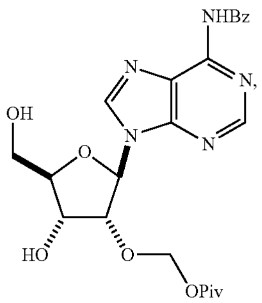

in the presence of pyridine trifluoroacetate and pyridine to obtain a compound of formula (6):

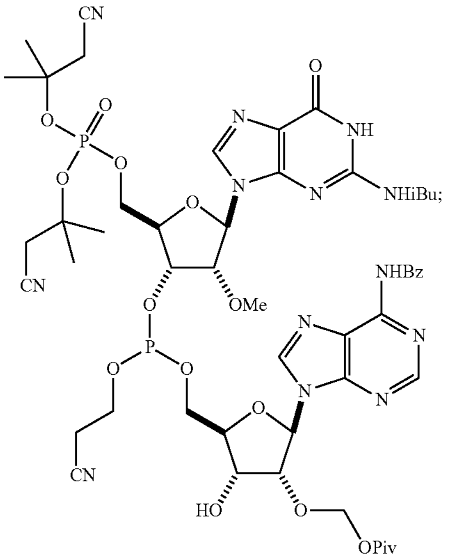

b.1) reacting the compound of formula (6) with a compound of formula (10):
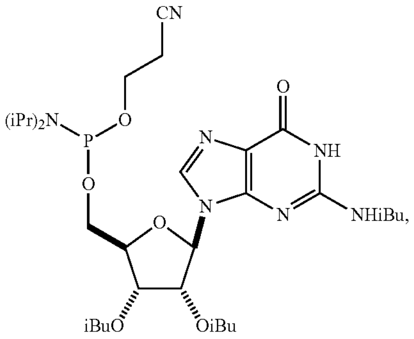
in the presence of pyridine trifluoroacetate and pyridine; to obtain a compound of formula (11-a):
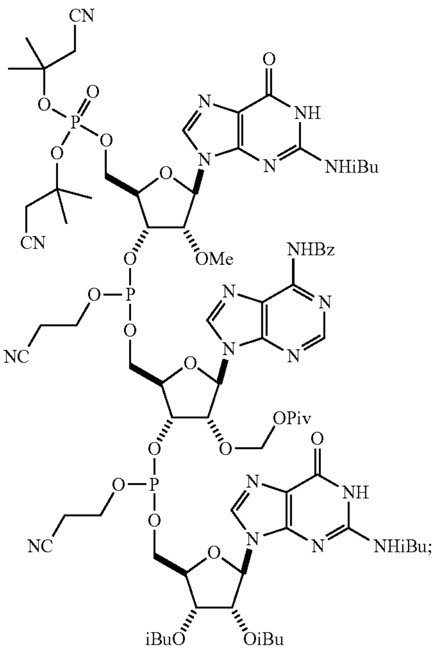
and
b.2) reacting the compound of formula (11-a) with tert-butyl hydroperoxide to obtain a compound of formula (11):
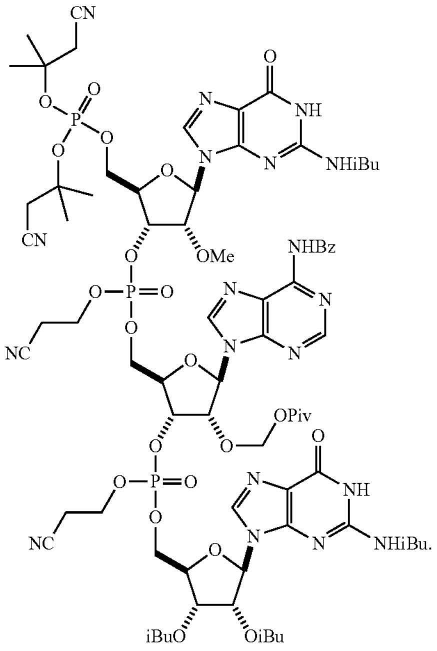
20. A compound having the structure:
formula (1);
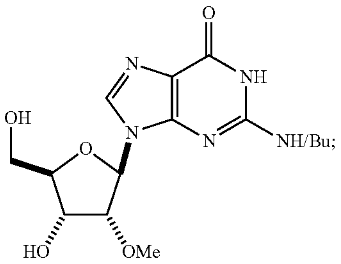
formula (3)
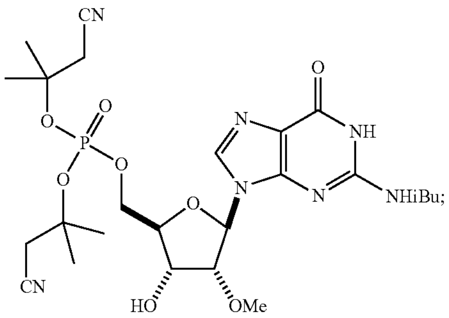

formula (4)
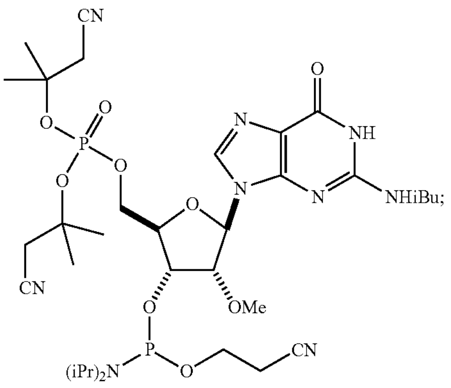
formula (5)
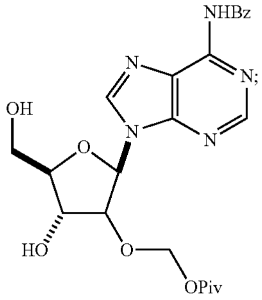
formula (6)
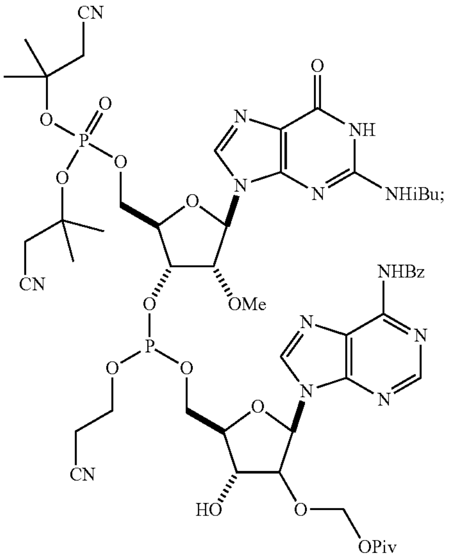
formula (7)
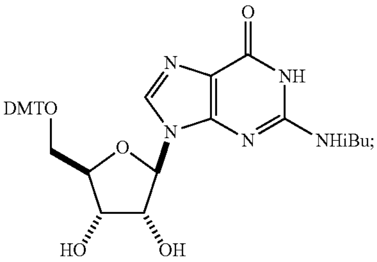
formula (8)
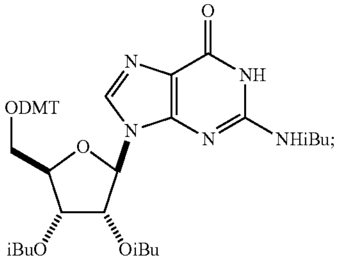
formula (9)
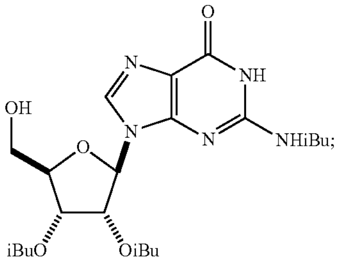
formula (10)
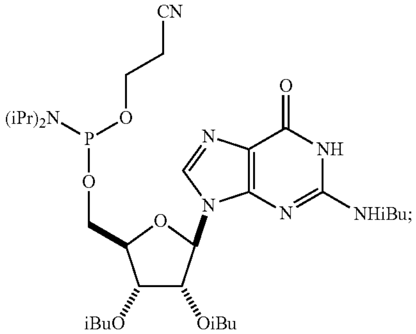

formula (11)
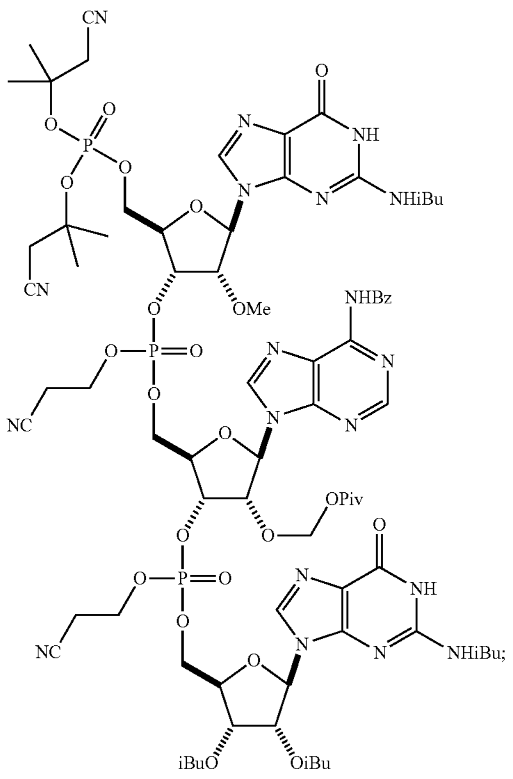
formula (11-a)
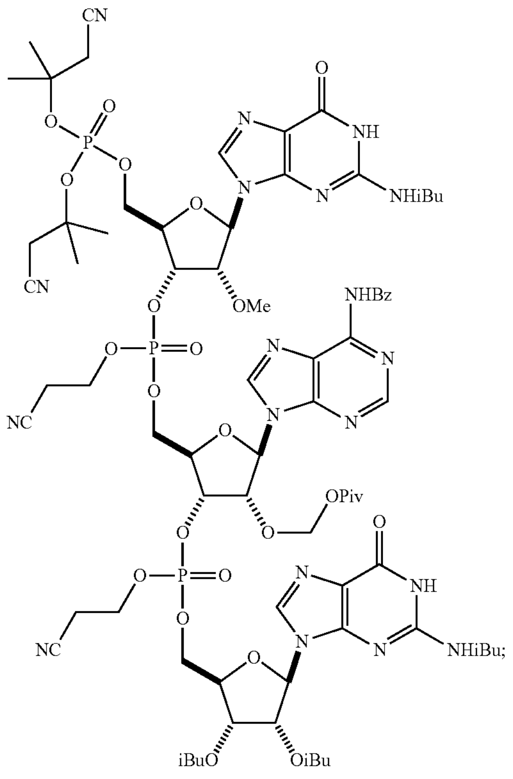
formula (12-a)
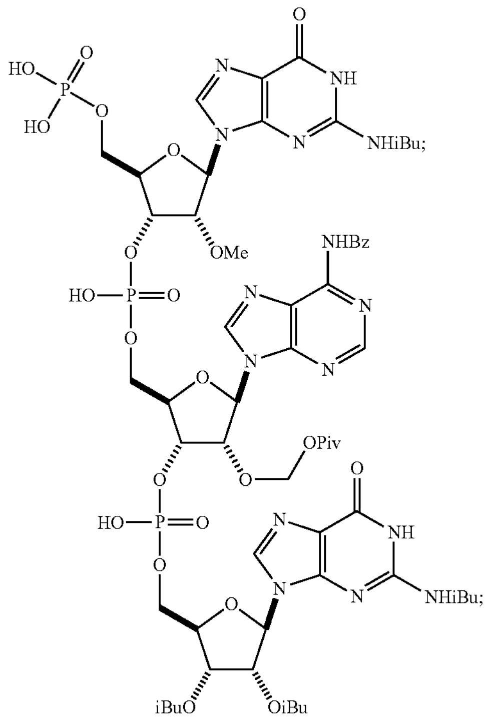
formula (12-b)
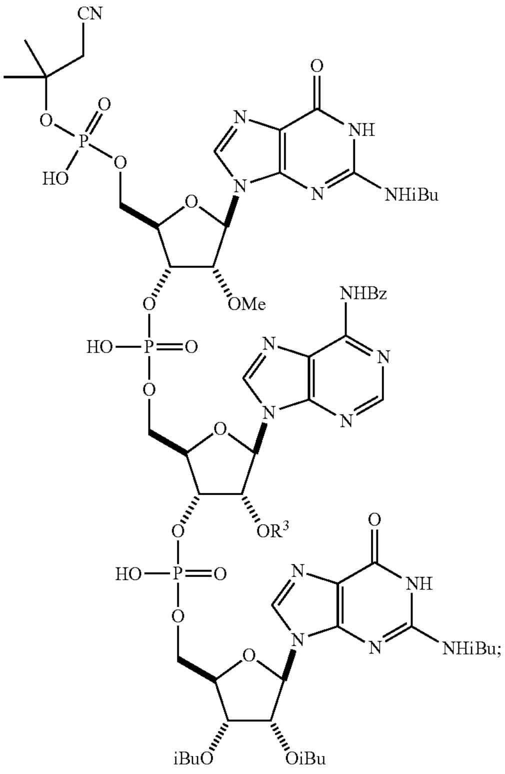

formula (12)
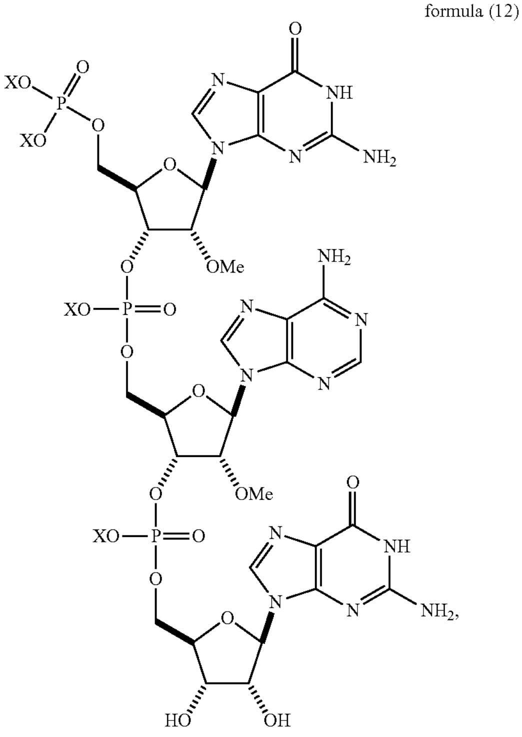
wherein the X is absent H, $Na^+$, or DMOA;
formula (15)
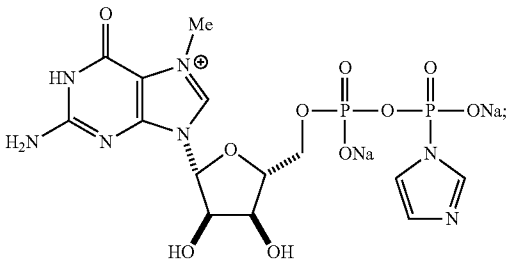
or
formula (16)
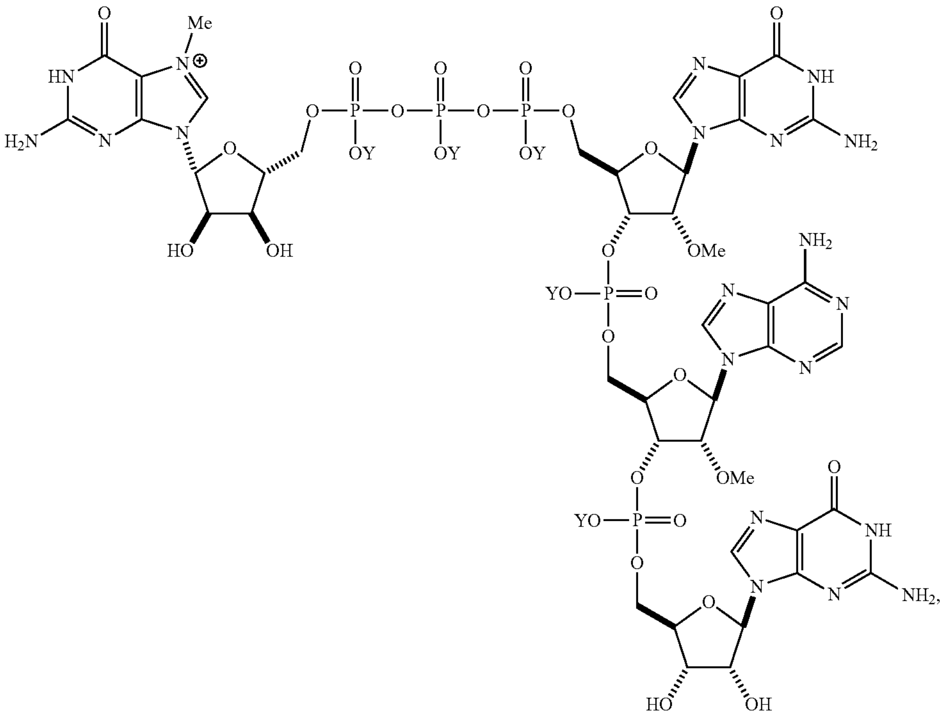
wherein each instance of Y is independently $NH_4^+$ or absent;
or a salt thereof.
* * * * *